(12) United States Patent
Araki et al.

(10) Patent No.: US 7,718,377 B2
(45) Date of Patent: May 18, 2010

(54) INSULIN RESISTANCE CURATIVE AND METHOD OF SCREENING THE SAME

(75) Inventors: Kazushi Araki, Tokyo (JP); Jun Ohsumi, Tokyo (JP); Makoto Yachi, Tokyo (JP)

(73) Assignee: Kyoto Pharmaceutical Industries, Ltd., Kyoto (JP)

( * ) Notice: Subject to any disclaimer, the term of this patent is extended or adjusted under 35 U.S.C. 154(b) by 1143 days.

(21) Appl. No.: 10/558,554

(22) PCT Filed: May 28, 2004

(86) PCT No.: PCT/JP2004/007787

§ 371 (c)(1),
(2), (4) Date: Jan. 18, 2006

(87) PCT Pub. No.: WO2004/106542

PCT Pub. Date: Dec. 9, 2004

(65) Prior Publication Data

US 2007/0059762 A1    Mar. 15, 2007

(30) Foreign Application Priority Data

May 29, 2003    (JP)    ............................. 2003-152544

(51) Int. Cl.
    *G01N 33/53*    (2006.01)
    *A61K 31/47*    (2006.01)
(52) U.S. Cl. .................... 435/7.1; 514/310; 546/146
(58) Field of Classification Search ............... None
    See application file for complete search history.

(56) References Cited

U.S. PATENT DOCUMENTS

| 4,687,777 | A | 8/1987 | Meguro et al. |
| 5,002,953 | A | 3/1991 | Hindley |
| 6,586,189 | B2 * | 7/2003 | Forman .................... 435/7.1 |

FOREIGN PATENT DOCUMENTS

| WO | 99/58521 | 11/1999 |
| WO | 99/61435 | 12/1999 |
| WO | 00/71540 | 11/2000 |
| WO | 01/70754 | 9/2001 |
| WO | 02/18363 | 3/2002 |
| WO | 02/064094 | 8/2002 |
| WO | 02/096880 | 12/2002 |

OTHER PUBLICATIONS

N. Hashimoto et al., "Insulin receptor and epidermal growth factor receptor dephosphorylation by three major rat liver protein-tyrosine phosphatases expressed in a recombinant bacterial system", Biochemical Journal, vol. 284, pp. 569-576, 1992.
M. Elchebly et al., "Increased Insulin Sensitivity and Obesity Resistance in Mice Lacking the Protein Tyrosine Phosphatase-1B Gene", Science, vol. 283, pp. 1544-1548, Mar. 5, 1999.
P. Tontonoz et al., "Stimulation of Adipogenesis in Fibroblasts by PPARγ2, a Lipid-Activated Transcription Factor", Cell, vol. 79, No. 7, pp. 1147-1156, Dec. 30, 1994.
R. P. Brun et al., "Differential activation of adipogenesis by multiple PPAR isoforms", Genes & Development, vol. 10, No. 8, pp. 974-984, Apr. 17, 1996.
A. Hiragun et al., "Preadipocyte Differentiation In Vitro: Identification of a Highly Active Adipogenic Agent", Journal of Cellular Physiology, vol. 134, No. 1, pp. 124-130, Jan. 1988.
J. Ohsumi et al., "Troglitazone Prevents the Inhibitory Effects of Inflammatory Cytokines on Insulin-Induced Adipocyte Differentiation in 3T3-L1 Cells", Endocrinology, vol. 135, No. 5, pp. 2279-2282, Nov. 1994.
J. M. Lehmann et al., "An Antidiabetic Thiazolidinedione is a High Affinity Ligand for Peroxisome Proliferator-activated Receptor γ (PPARγ)", The Journal of Biological Chemistry, vol. 270, No. 22, pp. 12953-12956, Jun. 2, 1995.
L. Nagy et al., "Oxidized LDL Regulates Macrophage Gene Expression through Ligand Activation of PPARγ", Cell, vol. 93, No. 2, pp. 229-240, Apr. 17, 1998.
F. Picard et al., "PPARγ and Glucose Homeostasis", Annu. Rev. Nutr., vol. 22, pp. 167-197, 2002.
B. M. Forman et al., "15-Deoxy-$\Delta^{12,14}$-Prostaglandin $J_2$ is a Ligand for the Adipocyte Determination Factor PPARγ", Cell, vol. 83, No. 5, pp. 803-812, Dec. 1, 1995.
G. Krey et al., "Fatty Acids, Eicosanoids, and Hypolipidemic Agents Identified as Ligands of Peroxisome Proliferator-Activated Receptors by Coactivator-Dependent Receptor Ligand Assay", Molecular Endocrinology, vol. 11, No. 6, pp. 779-791, Jun. 1997.
C. Yuan et al., "The TRAP220 component of a thyroid hormone receptor-associated protein (TRAP) coactivator complex interacts directly with nuclear receptors in a ligand-dependent fashion", Proc. Natl. Acad. Sci., USA, vol. 95, No. 14, pp. 7939-7944, Jul. 1998.
M. A. Iannone et al., "Multiplexed Molecular Interactions of Nuclear Receptors using Fluorescent Microspheres", Cytometry, vol. 44, No. 4, pp. 326-337, Aug. 1, 2001.
C. Qi et al., "Peroxisome Proliferator-Activated Receptors Coactivators, and Downstream Targets", Cell Biochemistry and Biophysics, vol. 32, pp. 187-204, 2000.
R. L. Nelson et al., "Identification, Purification, and Characterization of Phosphotyrosine-Specific Protein Phosphatases from Cultured Chicken Embryo Fibroblasts", Molecular and Cellular Biology, vol. 4, No. 6, pp. 1003-1012, Jun. 1984.
N. K. Tonks et al., "Purification of the Major Protein-tyrosine-phosphatases of Human Placenta", The Journal of Biological Chemistry, vol. 263, No. 14, pp. 6722-6730, May 15, 1988.

(Continued)

*Primary Examiner*—Zinna N Davis
(74) *Attorney, Agent, or Firm*—Wenderoth, Lind & Ponack, L.L.P.

(57) ABSTRACT

The present invention provides a screening method for a compound which is highly safe and has a prophylactic or therapeutic effect on diabetes, and a highly safe pharmaceutical composition for the prophylaxis or treatment of diabetes. Specifically, a drug for the prophylaxis or treatment of diabetes, which contains, as an active ingredient, a compound having PPARγ activation activity and PTP inhibitory activity, and a method of screening for the drug are provided.

4 Claims, 3 Drawing Sheets

OTHER PUBLICATIONS

E. Hoppe et al., "Expression, purification and crystallization of human phosphotyrosine phosphatase 1B", Eur. J. Biochem., vol. 223, No. 3, pp. 1069-1077, 1994.

Y. A. Puius et al., "Identification of a second aryl phosphate-binding site in protein-tyrosine phosphatase 1B: A paradigm for inhibitor design", Proc. Natl. Acad. Sci., USA, vol. 94, No. 25, pp. 13420-13425, Dec. 9, 1997.

H. Cho et al., "Purification and Characterization of a Soluble Catalytic Fragment of the Human Transmembrane Leukocyte Antigen Related (LAR) Protein Tyrosine Phosphatase from an *Escherichia coli* Expression System", Biochemistry, vol. 30, No. 25, pp. 6210-6216, Jun. 25, 1991.

M. J. King et al., "Assay of phosphotyrosyl protein phosphatase using synthetic peptide 1142-1153 of the insulin receptor", FEBS Letters, vol. 237, No. 1, 2, pp. 137-140, Sep. 12, 1988.

Q. Wang et al., "Fluorescein monophosphates as fluorogenic substrates for protein tyrosine phosphatases", Biochimica et Biophysica Acta, vol. 1431, No. 1, pp. 14-23, Apr. 12, 1999.

J. Roome et al., "Protein phosphotyrosine phosphatase purified from the particulate fraction of human placenta dephosphorylates insulin and growth-factor receptors", Biochem. J., vol. 256, No. 2, pp. 493-500, Dec. 1, 1988.

M. F. Cicirelli et al., "Microinjection of a protein-tyrosine-phosphatase inhibits insulin action in *Xenopus oocytes*", Proc. Natl. Acad. Sci. USA, vol. 87, No. 14, pp. 5514-5518, Jul. 1990.

M. R. Calera et al., "Dynamics of Protein-tyrosine Phosphatases in Rat Adipocytes", The Journal of Biological Chemistry, vol. 275, No. 9, pp. 6308-6312, Mar. 3, 2000.

S. Tamura et al., "Insulin-like effect of vanadate on adipocyte glycogen synthase and on phosphorylation of 95,000 dalton subunit of insulin receptor", Biochemical and Biophysical Research Communications, vol. 113, No. 1, pp. 80-86, May 31, 1983.

T. Suzuki et al., "Potentiation of Insulin-related Signal Transduction by a Novel Protein-tyrosine Phosphatase Inhibitor, Et-3,4-dephostatin, on Cultured 3T3-L1 Adipocytes", The Journal of Biological Chemistry, vol. 276, No. 29, pp. 27511-27518, Jul. 20, 2001.

J. Wrobel et al., "PTP1B Inhibition and Antihyperglycemic Activity in the ob/ob Mouse Model of Novel 11-Arylbenzo[*b*]naphtho[2,3-*d*]furans and 11-Arylbenzo[*b*]naphtho[2,3-*d*]thiophenes", Journal of Medicinal Chemistry, vol. 42, No. 17, pp. 3199-3202, 1999.

M. Sarmiento et al., "Structure-Based Discovery of Small Molecule Inhibitors Targeted to Protein Tyrosine Phosphatase 1B", Journal of Medicinal Chemistry, vol. 43, No. 2, pp. 146-155, 2000.

H. S. Andersen et al., "2-(Oxalylamino)-Benzoic Acid is a General, Competitive Inhibitor of Protein-Tyrosine Phosphatases", The Journal of Biological Chemistry, vol. 275, No. 10, pp. 7101-7108, Mar. 10, 2000.

L. F. Iversen et al., "Structure-based Design of a Low Molecular Weight, Nonphosphorus, Nonpeptide, and Highly Selective Inhibitor of Protein-Tyrosine Phosphatase 1B", The Journal of Biological Chemistry, vol. 275, No. 14, pp. 10300-10307, Apr. 7, 2000.

M. S. Malamas et al., "New Azolidinediones as Inhibitors of Protein Tyrosine Phosphatase 1B with Antihyperglycemic Properties", Journal of Medicinal Chemistry, vol. 43, No. 5, pp. 995-1010, 2000.

M. S. Malamas et al., "Novel Benzofuran and Benzothiophene Biphenyls as Inhibitors of Protein Tyrosine Phosphatase 1B with Antihyperglycemic Properties", Journal of Medicinal Chemistry, vol. 43, No. 7, pp. 1293-1310, 2000.

Y. A. Puius et al., "Identification of a second aryl phosphate-binding site in protein-tyrosine phosphatase 1B: A paradigm for inhibitor design", Proc. Natl. Acad. Sci. USA, vol. 94, pp. 13420-13425, Dec. 1997.

A. Ullrich et al., "Human insulin receptor and its relationship to the tyrosine kinase family of oncogenes", Nature, vol. 313, pp. 756-761, Feb. 28, 1985.

\* cited by examiner

INSULIN RESISTANCE CURATIVE AND METHOD OF SCREENING THE SAME

This application is a U.S. national stage of International Application No. PCT/JP2004/007787 filed May 28, 2004.

TECHNICAL FIELD

The present invention relates to a highly safe drug for the prophylaxis or treatment of diabetes, which comprises, as an active ingredient, a compound having high efficacy and preventing side effects (e.g., edema, cardiac enlargement, body fluid retention, hydrothorax etc.) caused by PPAR (peroxisome proliferator-activated receptor)γ activation activity, because the compound has PPARγ activation activity and PTP (Protein tyrosine phosphatase) inhibitory activity, and a method of screening for said drug.

BACKGROUND ART

PPARγ is one of the nuclear receptors that express mainly in adipocytes. Activation of PPARγ is considered to not only promote differentiation or maturation of adipocytes, but also be involved in the improvement of insulin resistance in diabetes, macrophage's transformation into foam cells in arteriosclerosis, and the like. For example, it is considered that, by the activation of PPARγ and promotion of differentiation of adipocyte, insulin resistance caused by TNF-α, free fatty acid and the like is eliminated and a blood glucose lowering effect and the like are exhibited on type 2 diabetes. Therefore, a compound having a superior PPARγ activation activity is known to be useful as an anti-hyperglycemia, anti-hyperlipidemia, insulin sensitizer, therapeutic agent for diabetes, therapeutic agent for diabetic complications, impaired glucose tolerance improving agent, anti-arteriosclerosis, anti-obesity, anti-inflammatory agent, an agent for the prophylaxis or treatment of PPAR-mediated diseases and an agent for the prophylaxis or treatment of syndrome X. However, PPARγ activators may express adverse events as side effects in clinical use, such as heart weight gain, cardiac enlargement, edema, hydrothorax and the like. These side effects are considered to be the events associated with accumulation of body fluid caused by activation of PPARγ.

PTP is an enzyme that catalyzes dephosphorylation of phosphotyrosine in protein, and PTP-1B, LAR (leukocyte antigen-related) PTP, LRP and the like are known. In addition, PTP is considered to be a phosphatase that dephosphorylates, for example, insulin receptor and the like. It is known that PTP is involved in the regulated inhibition of insulin receptors through dephosphorylation of insulin receptors. Therefore, a pharmaceutical agent that selectively inhibits PTP (preferably PTP-1B) enhances signaling after binding of insulin to its receptor, by the activity and has a known potential of becoming a drug for the prophylaxis or treatment of, for example, diabetes, hyperglycemia, impaired glucose tolerance, obesity, hyperlipidemia, diabetes complication, gestational diabetes, polycystic ovary syndrome, malignant tumor, autoimmune disease, allergic disease, immunodeficiency, inflammatory disease, neuropathy, neurodegenerative disease, infectious disease and the like (particularly a drug for the prophylaxis or treatment of diabetes) (see Biochemical Journal, 1992, vol. 284, p. 569 and Science, 1999, vol. 283, p. 1544).

At present, vanadium derivatives, phosphotyrosine derivatives and the like are known as PTP-1B inhibitors. Due to the problems in the specificity of inhibitory activity, permeability into cells, toxicity and the like, however, they have not been put to practical use as yet.

While WO02/096880 discloses compounds having PPARγ activation activity, it is not known at all that the compounds have PTP inhibitory activity.

DISCLOSURE OF THE INVENTION

The present inventors have conducted intensive studies in an attempt to develop a highly safe PPARγ activator which maintains superior efficacy based on PPARγ activation activity, and which prevents side effects (e.g., edema etc.), and found that a compound having PPARγ activation activity and PTP-1B inhibitory activity is useful as a highly safe, superior antidiabetic, because it remarkably prevents side effects despite its potent PPARγ activation activity, which resulted in the completion of the present invention.

Accordingly, the present invention provides a screening method for a compound having PPARγ activation activity and PTP-1B inhibitory activity and a drug for the prophylaxis or treatment of diabetes.

Specifically, the present invention relates to (1) a method of screening for an insulin sensitizer, which comprises the following steps 1) and 2):

step 1) a step of measuring PTP-1B inhibitory activity of a test substance having PPARγ activation activity; and step 2) a step of selecting a test substance having PTP-1B inhibitory activity, based on the PTP-1B inhibitory activity measured in the above-mentioned step 1), (2) a method of screening for an insulin sensitizer, which comprises the following steps 1) to 4):

step 1) a step of measuring PPARγ activation activity of a test substance;

step 2) a step of selecting a substance having PPARγ activation activity, based on the PPARγ activation activity measured in the above-mentioned step 1);

step 3) a step of measuring PTP-1B inhibitory activity of the substance having PPARγ activation activity selected in the above-mentioned step 2); and step 4) a step of selecting a test substance having PTP-1B inhibitory activity, based on the PTP-1B inhibitory activity measured in the above-mentioned step 3), (3) a method of screening for an insulin sensitizer, which comprises the following steps 1) and 2):

step 1) a step of measuring PPARγ activation activity of a test substance having PTP-1B inhibitory activity; and step 2) a step of selecting a test substance having PPARγ activation activity, based on the PPARγ activation activity measured in the above-mentioned step 1), (4) a method of screening for an insulin sensitizer, which comprises the following steps 1) to 4):

step 1) a step of measuring PTP-1B inhibitory activity of a test substance;

step 2) a step of selecting a test substance having PTP-1B inhibitory activity, based on the PTP-1B inhibitory activity measured in the above-mentioned step 1);

step 3) a step of measuring the PPARγ activation activity of the substance having PTP-1B inhibitory activity selected in the above-mentioned step 2); and step 4) a step of selecting a test substance having PPARγ activation activity, based on the PPARγ activation activity measured in the above-mentioned step 3), (5) an insulin sensitizer comprising a substance obtained by the screening method described in any of the above-mentioned (1) to (4), (6) a method for the prophylaxis or treatment of diabetes, which comprises administering a substance obtained by the screening method described in any of the above-mentioned (1) to (4), (7) use of a substance obtained by the screening method described in any of the above-mentioned (1) to (4), for the production of an insulin sensitizer, (8) a method of selecting a PPARγ activator that prevents occurrence of side effects, which comprises the following steps 1) and 2):

step 1) a step of measuring PTP-1B inhibitory activity of a test substance having PPARγ activation activity; and step 2) a step of selecting a test substance having PTP-1B inhibitory activity, based on the PTP-1B inhibitory activity measured in the above-mentioned step 1), (9) a method of selecting a PPARγ activator that prevents occurrence of edema, cardiac enlargement, body fluid retention or hydrothorax, which comprises the following steps 1) and 2):

step 1) a step of measuring PTP-1B inhibitory activity of a test substance having PPARγ activation activity; and step 2) a step of selecting a test substance having PTP-1B inhibitory activity, based on the PTP-1B inhibitory activity measured in the above-mentioned step 1),

(10) a method of selecting a PPARγ activator that prevents occurrence of side effects, which comprises the following steps 1) and 2):

step 1) a step of measuring PPARγ activation activity of a test substance having PTP-1B inhibitory activity; and step 2) a step of selecting a test substance having PPARγ activation activity, based on the PPARγ activation activity measured in the above-mentioned step 1),

(11) a method of selecting a PPARγ activator that prevents occurrence of edema, cardiac enlargement, body fluid retention or hydrothorax, which comprises the following steps 1) and 2):

step 1) a step of measuring PPARγ activation activity of a test substance having PTP-1B inhibitory activity; and step 2) a step of selecting a test substance having PPARγ activation activity, based on the PPARγ activation activity measured in the above-mentioned step 1),

(12) a PPARγ activator comprising a substance obtained by the selection method described in any of the above-mentioned (8) to (11),

(13) use of a compound having PPARγ activation activity and PTP-1B inhibitory activity, for the production of an insulin sensitizer,

(14) an insulin sensitizer that prevents occurrence of side effects, which comprises a compound having PPARγ activation activity and PTP-1B inhibitory activity,

(15) an insulin sensitizer that prevents occurrence of edema, cardiac enlargement, body fluid retention or hydrothorax, which comprises a compound having PPARγ activation activity and PTP-1B inhibitory activity,

(16) a PPARγ activator that prevents occurrence of side effects caused by the activation of PPARγ, which comprises a compound having PPARγ activation activity and PTP-1B inhibitory activity,

(17) a PTP-1B inhibitor comprising a compound having an insulin resistance improving effect enhanced by PPARγ activation activity and PTP-1B inhibitory activity of the compound,

(18) a highly safe drug for the prophylaxis or treatment of diabetes, which comprises a compound having PPARγ activation activity and PTP-1B inhibitory activity,

(19) a PTP-1B inhibitor comprising a heterocyclic compound represented by the following formula (I)

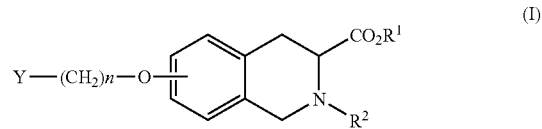

wherein $R^1$ is a hydrogen atom or $C_{1-6}$ alkyl, $R^2$ is a hydrogen atom,

—CO—$R^3$ wherein $R^3$ is $C_{2-6}$ alkyl optionally substituted by halogen(s),

—CO—C($R^4$)=C($R^4$)—$R^5$ wherein both $R^4$ are the same or different and each is a hydrogen atom or $C_{1-4}$ alkyl, and $R^5$ is $C_{1-8}$ alkyl, $C_{2-8}$ alkenyl, aryl or aromatic heterocycle,

—CO—C≡C—$R^6$ wherein $R^6$ is $C_{1-8}$ alkyl,

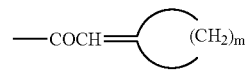

wherein m is an integer of 2-7, aryl, optionally substituted aryl-$C_{1-3}$ alkyl, $C_{1-6}$ alkyl optionally substituted by halogen(s), $C_{2-6}$ alkenyl, $C_{3-8}$ cycloalkyl or $C_{3-8}$ cycloalkyl-$C_{1-3}$ alkyl, Y is

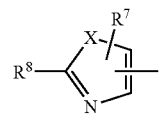

wherein $R^7$ is a hydrogen atom or $C_{1-4}$ alkyl, $R^8$ is $C_{5-8}$ alkyl, $C_{4-8}$ cycloalkyl, $C_{1-4}$ alkylthio-$C_{1-6}$ alkyl, $R^{10}$—C($R^9$)=C($R^9$)— wherein both $R^9$ are the same or different and each is a hydrogen atom or $C_{1-4}$ alkyl, and $R^{10}$ is $C_{1-6}$ alkyl optionally substituted by halogen(s), $C_{2-8}$ alkenyl, aryl, aromatic heterocycle, $C_{3-8}$ cycloalkyl, $C_{3-8}$ cycloalkyl-$C_{1-3}$ alkyl, $C_{1-4}$ alkoxy-$C_{1-6}$ alkyl, $C_{1-4}$ alkylthio-$C_{1-6}$ alkyl or $C_{1-6}$ alkyl substituted by ($R^9$)$_2$N—wherein both $R^9$ are the same or different and each is a hydrogen atom or $C_{1-4}$ alkyl, $R^{12}$—CO—N($R^{11}$)— wherein $R^{11}$ is a hydrogen atom or $C_{1-4}$ alkyl, and $R^{12}$ is $C_{1-6}$ alkyl or aryl, $R^{13}$—Z— wherein R$^{13}$ is C$_{1-8}$ alkyl or aryl, and Z is an oxygen atom or a sulfur atom, or

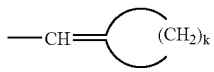

wherein k is an integer of 2-7, and
X is an oxygen atom or a sulfur atom, or
R$^{15}$—C(R$^{14}$)=N—O—
wherein R$^{14}$ is a hydrogen atom or C$_{1-4}$ alkyl, and
R$^{15}$ is aryl or aromatic heterocycle,
Y—(CH$_2$)$_n$—O— is bonded to the 6- or 7-position of the tetrahydroisoquinoline skeleton, and
n is an integer of 1-4, or a pharmaceutically acceptable salt thereof,
(20) the PTP-1B inhibitor of the above-mentioned (19), which comprises a heterocyclic compound of the formula (I), wherein
R$^2$ is
  a hydrogen atom,
  —CO—R$^3$
    wherein R$^3$ is C$_{2-6}$ alkyl optionally substituted by halogen(s),
  —COC(R$^4$)=C(R$^4$)—R$^5$
    wherein both R$^4$ are the same or different and each is a hydrogen atom or C$_{1-4}$ alkyl, and R$^5$ is C$_{1-8}$ alkyl, C$_{2-8}$ alkenyl, aryl or aromatic heterocycle, or
  —CO—C≡C—R$^6$
    wherein R$^6$ is C$_{1-8}$ alkyl or aryl, or a pharmaceutically acceptable salt thereof,
(21) the PTP-1B inhibitor of the above-mentioned (19) or (20), which comprises a heterocyclic compound of the formula (I), wherein
R$^2$ is —CO—C(R$^4$)=C(R$^4$)—R$^5$
  wherein each R$^4$ is a hydrogen atom, and R$^5$ is C$_{1-8}$ alkyl or C$_{2-8}$ alkenyl, or a pharmaceutically acceptable salt thereof,
(22) the PTP-1B inhibitor described in any of the above-mentioned (19) to (21), which comprises a heterocyclic compound of the formula (I), wherein
Y is

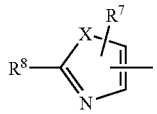

wherein
R$^7$ is a hydrogen atom or C$_{1-4}$ alkyl,
R$^8$ is
  C$_{5-8}$ alkyl, C$_{4-8}$ cycloalkyl,
  R$^{10}$—C(R$^9$)=C(R$^9$)—
    wherein both R$^9$ are the same or different and each is a hydrogen atom or C$_{1-4}$ alkyl, and R$^{10}$ is C$_{1-6}$ alkyl, C$_{2-8}$ alkenyl, aryl or aromatic heterocycle,
  R$^{12}$—CO—N(R$^{11}$)—
    wherein R$^{11}$ is a hydrogen atom or C$_{1-4}$ alkyl, and R$^{12}$ is C$_{1-6}$ alkyl or aryl, or
  R$^{13}$—Z—
    wherein R$^{13}$ is C$_{1-8}$ alkyl or aryl, and Z is an oxygen atom or a sulfur atom, and
X is an oxygen atom or a sulfur atom, or
R$^{15}$—C(R$^4$)=N—O— wherein R$^{14}$ is a hydrogen atom or C$_{1-4}$ alkyl, and
R$^{15}$ is aryl or aromatic heterocycle, or a pharmaceutically acceptable salt thereof,
(23) the PTP-1B inhibitor described in any of the above-mentioned (19) to (22), which comprises a heterocyclic compound of the formula (I), wherein Y—(CH$_2$)$_n$—O— is bonded to the 7-position of the tetrahydroisoquinoline skeleton, and
n is 2, or a pharmaceutically acceptable salt thereof,
(24) the PTP-1B inhibitor described in any of the above-mentioned (19) to (23), which comprises a heterocyclic compound of the formula (I), wherein
Y is

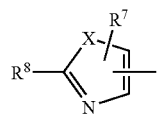

wherein
R$^7$ is a hydrogen atom or C$_{1-4}$ alkyl, and
R$^8$ is R$^{10}$—C(R$^9$)=C(R$^9$)—
  wherein both R$^9$ are the same or different and each is a hydrogen atom or C$_{1-4}$ alkyl, and R$^{10}$ is C$_{1-6}$ alkyl, C$_{2-8}$ alkenyl or aryl, or a pharmaceutically acceptable salt thereof,
(25) the PTP-1B inhibitor described in any of the above-mentioned (19) to (23), which comprises a heterocyclic compound of the formula (I), wherein
Y is

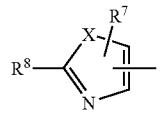

wherein
R$^7$ is a hydrogen atom or C$_{1-4}$ alkyl, and
R$^8$ is C$_{5-8}$ alkyl or C$_{4-8}$ cycloalkyl, or a pharmaceutically acceptable salt thereof,
(26) the PTP-1B inhibitor described in any of the above-mentioned (19) to (23), which comprises a heterocyclic compound of the formula (I), wherein
Y is

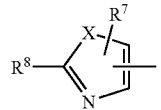

wherein
R$^7$ is C$_{1-4}$ alkyl,
R$^8$ is R$^{10}$—C(R$^9$)=C(R$^9$)—
  wherein both R$^9$ are the same or different and each is a hydrogen atom or a C$_{1-4}$ alkyl, and R$^{10}$ is C$_{1-6}$ alkyl, and
X is an oxygen atom, or a pharmaceutically acceptable salt thereof,

(27) the PTP-1B inhibitor described in any of the above-mentioned (19) to (21), which comprises a heterocyclic compound of the formula (I), wherein Y is any selected from the following formulas (a)-(n):

(a)
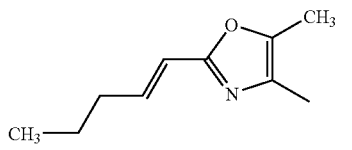

(b)
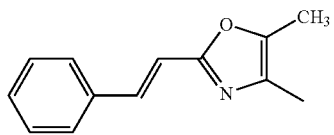

(c)
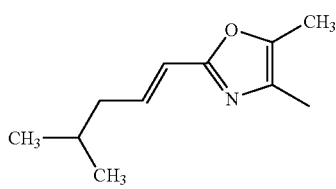

(d)
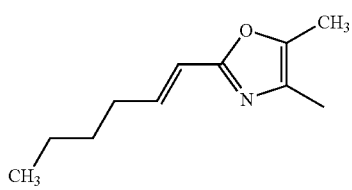

(e)
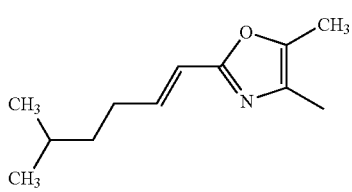

(f)
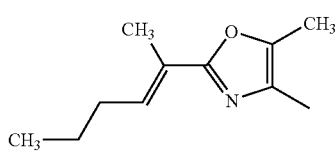

(g)
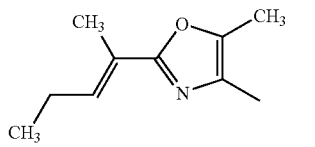

(h)
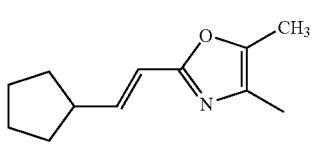

(i)
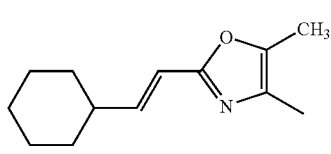

-continued

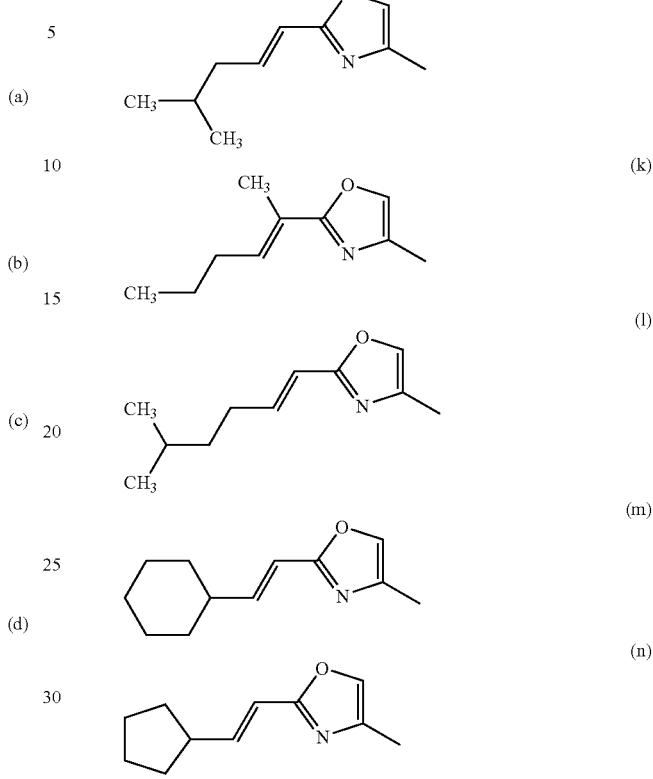

or a pharmaceutically acceptable salt thereof,

(28) a PTP-1B inhibitor comprising 2-(2,4-hexadienoyl)-7-[2-(5-methyl-2-(trans-1-penten-1-yl)oxazol-4-yl)ethoxy]-1,2,3,4-tetrahydroisoquinoline-(3S)-carboxylic acid, 2-(2,4-hexadienoyl)-7-{2-[5-methyl-2-(4-methyl-trans-1-penten-1-yl)oxazol-4-yl]ethoxy}-1,2,3,4-tetrahydroisoquinoline-(3S)-carboxylic acid, 2-(2-heptenoyl)-7-{2-[5-methyl-2-(4-methyl-trans-1-penten-1-yl)oxazol-4-yl]ethoxy}-1,2,3,4-tetrahydroisoquinoline-(3S)-carboxylic acid, 2-(2,4-hexadienoyl)-7-{2-[2-(trans-1-hexen-1-yl)-5-methyloxazol-4-yl]ethoxy}-1,2,3,4-tetrahydroisoquinoline-(3S)-carboxylic acid, 2-(2,4-hexadienoyl)-7-{2-[5-methyl-2-(5-methyl-trans-1-hexen-1-yl)oxazol-4-yl]ethoxy}-1,2,3,4-tetrahydroisoquinoline-(3S)-carboxylic acid, 2-(2,4-hexadienoyl)-7-{2-[5-methyl-2-(1-methyl-trans-1-penten-1-yl)oxazol-4-yl]ethoxy}-1,2,3,4-tetrahydroisoquinoline-(3S)-carboxylic acid, 2-(2,4-hexadienoyl)-7-{2-[5-methyl-2-(1-methyl-trans-1-buten-1-yl)oxazol}-4-yl]ethoxy)-1,2,3,4-tetrahydroisoquinoline-(3S)-carboxylic acid, 2-(2-hexenoyl)-7-{2-[5-methyl-2-(4-methyl-trans-1-penten-1-yl)oxazol-4-yl]ethoxy}-1,2,3,4-tetrahydroisoquinoline-(3S)-carboxylic acid, 2-(3-butenyl)-7-{2-[5-methyl-2-(4-methyl-trans-1-penten-1-yl)oxazol-4-yl]ethoxy}-1,2,3,4-tetrahydroisoquinoline-(3S)-carboxylic acid, 7-{2-[5-methyl-2-(4-methyl-trans-1-penten-1-yl)oxazol-4-yl]ethoxy}-2-(4-pentenyl)-1,2,3,4-tetrahydroisoquinoline-(3S)-carboxylic acid or a pharmaceutically acceptable salt thereof, and

(29) a PTP-1B inhibitor comprising 7-{2-[2-(trans-2-cyclohexylvinyl)-5-methyloxazol-4-yl]ethoxy}-2-(2,4-hexadienoyl)-1,2,3,4-tetrahydroisoquinoline-(3S)-carboxylic acid, 7-{2-[2-(trans-2-cyclopentylvinyl)-5-methyloxazol-4-yl]ethoxy}-2-(2,4-hexadienoyl)-1,2,3,4-tetrahydroisoquinoline-(3S)-carboxylic acid, 7-{2-[2-(5-fluoro-trans-1-penten-1-yl)-5-methyloxazol-4-yl]ethoxy}-2-(2,4-hexadienoyl)-1,2,3,4-tetrahydroisoquinoline-(3S)-carboxylic acid, 2-(2,4-hexadienoyl)-7-{2-[2-(1-methyl-trans-1-penten-1-yl)oxazol-4-yl]ethoxy}-1,2,3,4-tetrahydroisoquinoline-(3S)-carboxylic acid or a pharmaceutically acceptable salt thereof.

DETAILED DESCRIPTION OF THE INVENTION

Figure 1:
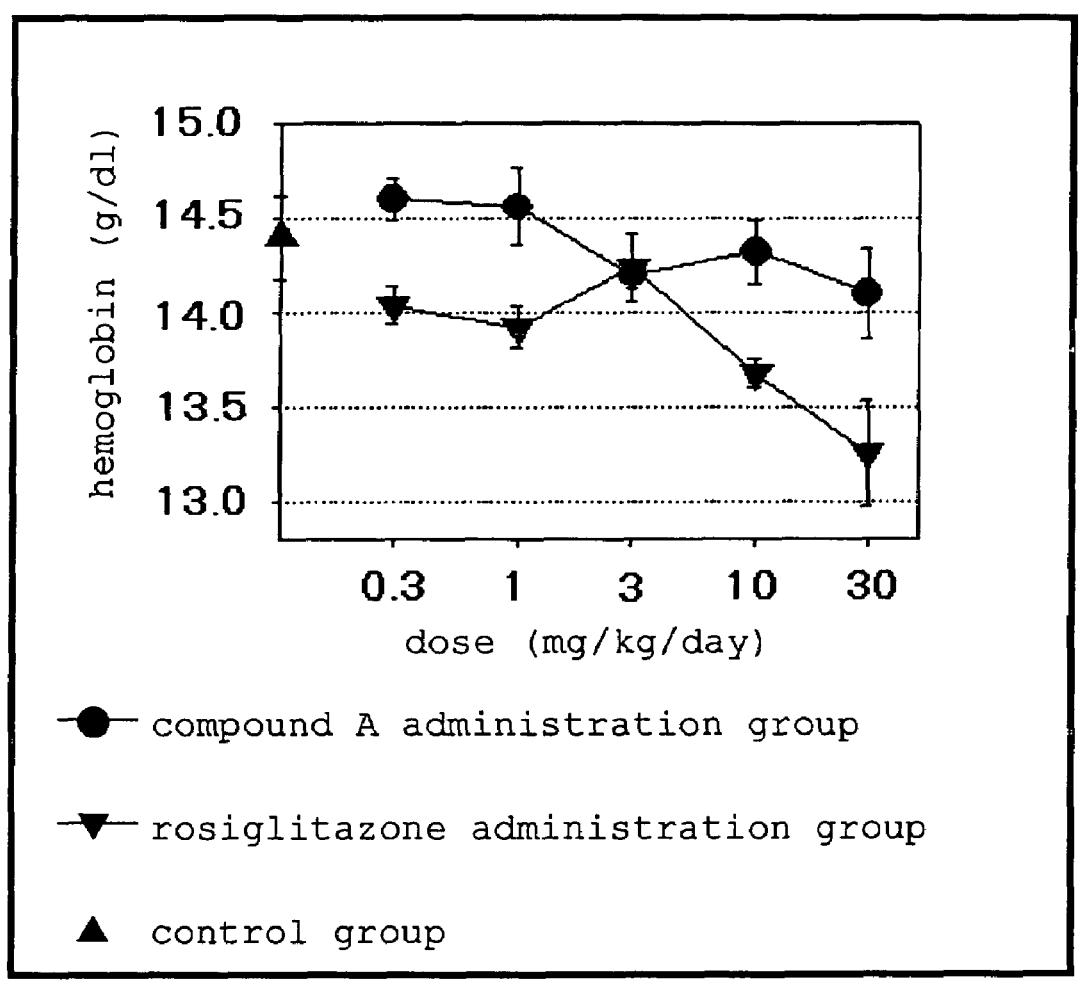
FIG. 1 shows a graph plotting a hemoglobin concentration on the vertical axis, and a dose of the test compound on the transverse axis.

In the present invention, the "a compound having PPARγ activation activity and PTP-1B inhibitory activity" is not particularly limited as long as it means a compound having both the "PPARγ activation activity" and "PTP-1B inhibitory activity" and is, for example, a compound selected by a screening method selected from the following (1)-(6).
(1) A method of screening for an insulin sensitizer, which comprises the following steps 1) and 2):
step 1) a step of measuring PTP-1B inhibitory activity of a test substance having PPARγ activation activity; and
step 2) a step of selecting a test substance having PTP-1B inhibitory activity, based on the PTP-1B inhibitory activity measured in the above-mentioned step
(2) A method of screening for an insulin sensitizer, which comprises the following steps 1) to 4):
step 1) a step of measuring PPARγ activation activity of a test substance;
step 2) a step of selecting a test substance having PPARγ activation activity, based on the PPARγ activation activity measured in the above-mentioned step 1);
step 3) a step of measuring the PTP-1B inhibitory activity of the substance having PPARγ activation activity selected by the above-mentioned step 2); and
step 4) a step of selecting a substance having PTP-1B inhibitory activity, based on the PTP-1B inhibitory activity measured in the above-mentioned step 3).
(3) A method of screening for an insulin sensitizer, which comprises the following steps 1) and 2):
step 1) a step of measuring PPARγ activation activity of a test substance having PTP-1B inhibitory activity; and
step 2) a step of selecting a test substance having PPARγ activation activity, based on the PPARγ activation activity measured in the above-mentioned step 1).
(4) A method of screening for an insulin sensitizer, which comprises the following steps 1) to 4):
step 1) a step of measuring PTP-1B inhibitory activity of a test substance;
step 2) a step of selecting a substance having PTP-1B inhibitory activity, based on the PTP-LB inhibitory activity measured in the above-mentioned step 1);
step 3) a step of measuring PPARγ activation activity of the substance having PTB-1B inhibitory activity selected in the above-mentioned step 2); and step 4) a step of selecting a substance having PPARγ activation activity, based on the PPARγ activation activity measured in the above-mentioned step 3).
(5) A screening method for a PPARγ activator, which comprises the following steps 1) and 2):
step 1) a step of measuring PTP-LB inhibitory activity of a test substance having PPARγ activation activity; and
step 2) a step of selecting a test substance having PTP-1B inhibitory activity, based on the PTP-1B inhibitory activity measured in the above-mentioned step 1).
(6) A screening method for a PTP-LB inhibitor, which comprises the following steps 1) and 2):
step 1) a step of measuring PPARγ activation activity of a test substance having PTP-1B inhibitory activity; and
step 2) a step of selecting a test substance having PPARγ activation activity, based on the PPARγ activation activity measured in the above-mentioned step 1).

In the above-mentioned (1) to (6), the "test substance" means a substance to be the object of measurement of PPARγ activation activity and PTP-1B inhibitory activity by the screening method of the present invention. As the test substance, compounds, metabolites of microorganisms, extracts of plant and animal tissues, derivatives thereof or a mixture thereof, and the like can be mentioned.

While the dose and concentration of the test substance can be appropriately set, or, for example, multiple kinds of doses may be set by preparing dilution series and the like. The test substance can be administered in a suitable state such as solid, liquid etc., and may be dissolved in a suitable buffer, or a stabilizer and the like may be added. In the case of a screening method using a cultured cell, it can be cultured by addition thereof to a medium. For addition to a medium, it may be added from the start of the culture, or may be added during the culture, where the frequency of addition is not limited to once. While the culture period in the presence of a test substance can be appropriately determined, preferred is 30 min to 2 weeks, more preferably 30 min to 48 hr. For administration of a test substance to a mammal, an administration mode is changed depending on the properties of the test substance from oral administration, intravenous injection, intraperitoneal injection, transdermal administration, subcutaneous injection and the like.

The PPARγ activation activity can be measured by, for example, the following methods.

PPARγ is involved in adipocyte differentiation (Cell. 1994 Dec. 30, vol. 79(7), p. 1147-56, and Genes Dev. 1996 Apr. 15, vol. 10(8), p. 974-84), and it is known that a compound capable of activating PPARγ promotes adipocyte differentiation (J Cell Physiol. 1988 January, vol. 134(1), p. 124-30, Endocrinology. 1994 November, vol. 135(5), p. 2279-82, and J. Biol. Chem. 1995 Jun. 2, vol. 270(22), p. 12953-6). Therefore, the presence of PPARγ activation activity is acknowledged when adipocyte differentiation is promoted by the addition of a test compound to a culture system of mouse 3T3-L1 cell line (American Type Culture Collection CCL 92.1), C3H10T1/2 cell line (American Type Culture Collection CCL-226) or an adipocyte precursor derived from mouse, rat, human and the like.

It is known that a compound that activates PPARγ increases expression of a group of genes such as aP2, CD36 and the like in cells (Cell. 1994 Dec. 30, vol. 79(7), p. 1147-56, Cell. 1998 Apr. 17, vol. 93(2), p. 229-40, and Annu. Rev. Nutr. 2002, vol. 22, p. 167-97). Therefore, when expression of aP2 and CD36 increases by the addition of a test compound to a cell expressing PPARγ, the test compound is considered to have PPARγ activation activity.

It is known that a compound that activates PPARγ can directly bind to PPARγ protein (J. Biol. Chem. 1995 Jun. 2, vol. 270(22), p. 12953-6, and Cell. 1995 Dec. 1, vol. 83(5), p. 803-12). Therefore, it is possible to obtain a PPARγ protein by purification from animal tissues according to a conventional method, or produce a PPARγ protein in *Escherichia coli*, insect cells or mammalian cells by gene recombination technique, and examine the binding ability of a test compound to the PPARγ protein. When the compound has a specific binding ability, the compound is considered to have PPARγ activation activity.

PPARγ protein is known to show higher binding ability to intracellular proteins such as SRC-1, TRAP220 and the like, which are called coactivators, when bound to a compound that activates PPARγ (Mol. Endocrinol. 1997 June, vol. 11(6), p. 779-91, Proc. Natl. Acad. Sci. USA. 1998 Jul. 7, vol. 95(14), p. 7939-44, Cytometry. 2001 Aug. 1, vol. 44(4), p. 326-37, and Cell Biochem. Biophys. 2000, vol. 32 Spring, p. 187-204). Therefore, it is possible to prepare a PPARγ protein and a coactivator protein such as SRC-1, TRAP220 and the like or a partial peptide thereof by a conventional method, react a test compound with the PPARγ protein, and determine the binding ability of the coactivator protein or peptide to the PPARγ protein. When the binding ability becomes high due to the action of the compound, the compound is considered to have PPARγ activation activity.

As a method for examining the level of activation of PPARγ, a so-called reporter assay is employed. For example, it is known that activity of intracellular luciferase increases when a promoter region of aP2 gene known to show an enhanced expression by PPARγ activation is linked to luciferase gene to generate a reporter gene, introduced into a cell with the PPARγ gene, and reacted with a compound that activates PPARγ (J. Biol. Chem. 1995 Jun. 2, vol. 270(22), p. 12953-6). Therefore, the presence of PPARγ activation activity is acknowledged when a test compound is reacted in a similar test system, and the measured product amount of intracellular reporter gene is found to have increased from that of a control. As a reporter assay based on a similar principle, the following method is also known. To be specific, it is known that intracellular luciferase activity increases when a protein wherein a ligand binding domain of PPARγ and a DNA binding region of a transcription factor (e.g., yeast transcription factor GAL4) other than PPAR, have been fused, is expressed in cells, and a reporter gene (e.g., luciferase gene) so prepared as to be responsible to the transcription factor (e.g., GAL4) used, is introduced into a cell, and a compound having PPARγ activation activity is reacted therewith (J. Biol. Chem. 1995 Jun. 2, vol. 270(22), p. 12953-6). Therefore, the presence of PPARγ activation activity is acknowledged when a test compound is reacted by a similar test method, and the measured intracellular luciferase activity is found to have increased from that of a control.

As a compound having PPARγ activation activity, compounds described in U.S. Pat. No. 4,687,777, U.S. Pat. No. 5,002,953 and WO00/71540 can be mentioned. However, the compound is not limited to the above-mentioned compounds as long as the presence of PPARγ activation activity can be acknowledged by the above-mentioned measurement methods.

In the present invention, the "PPARγ activator" means a compound having the above-mentioned "PPARγ activation activity" and a pharmaceutical composition comprising a compound having PPARγ activation activity.

The PTP inhibitory activity can be measured by, for example, the following methods.

A method of obtaining PTP such as PTP-1B etc. by purification from tissues and cells by a conventional method is known (Mol. Cell Biol. 1984 June, vol. 4(6), p. 1003-12, and J. Biol. Chem. 1988 May 15, vol. 263(14), p. 6722-30), and a method of obtaining PTP by production thereof in *Escherichia coli* and the like by genetic engineering is known (Eur. J. Biochem. 1994 Aug. 1, vol. 223(3), p. 1069-77, Proc. Natl. Acad. Sci. USA. 1997 Dec. 9, vol. 94(25), p. 13420-5, and Biochemistry. 1991 Jun. 25, vol. 30(25), p. 6210-6). When the thus-obtained PTP is reacted with phosphotyrosine or a peptide or protein containing phosphotyrosine, phosphoric acid is released due to the action of PTP. Therefore, the activity of PTP can be measured by assay of the resulting phosphoric acid (J. Biol. Chem. 1988 May 15, vol. 263(14), p. 6722-30, and FEBS Lett. 1988 Sep. 12, vol. 237(1-2), p. 137-40). In addition, p-nitrophenylphosphoric acid, fluoresceinphosphoric acid and the like, wherein a dephosphorylated form shows absorption or fluorescence, can be used instead of the phosphotyrosine. Thus, an assay comprising determination of absorption or fluorescence of a dephosphorylated form resulting from the reaction of PTP is also known (Eur. J. Biochem. 1994 Aug. 1, vol. 223(3), p. 1069-77, and Biochim. Biophys. Acta. 1999 Apr. 12, vol. 1431(1), p. 14-23). In this way, the PTP activity can be measured. When a PTP reaction is carried out in the presence of a test compound, and the PTP activity is found to have decreased from that of a control, the test compound is considered to have PTP inhibitory activity.

Moreover, in cells, PTP is considered to dephosphorylate and inactivate intracellular tyrosine phosphorylated proteins represented by insulin receptor and the like (Biochem J. 1988 Dec. 1, vol. 256(2), p. 493-500, Proc. Natl. Acad. Sci. USA. 1990 July, vol. 87(14), p. 5514-8, and J. Biol. Chem. 2000 Mar. 3, vol. 275(9), p. 6308-12). For example, vanadic acid and a certain kind of organic compound having PTP inhibitory activity are known to increase tyrosine phosphorylation of insulin receptor, and show an insulin-like action (Biochem. Biophys. Res. Commun. 1983 May 31, vol. 113(1), p. 80-6, and J. Biol. Chem. 2001 Jul. 20, vol. 276(29), p. 27511-8). Therefore, when, for example, a cell that expresses an insulin receptor is cultured and reacted with a test compound, and the test compound increases tyrosine phosphorylation of insulin receptor and an insulin-like action is observed, the test compound is considered to have PTP inhibitory activity.

As a compound having PTP-LB inhibitory activity, the compounds described in Journal of Medicinal Chemistry, 1999, vol. 42, p. 3199-3202, Journal of Medicinal Chemistry, 2000, vol. 43, p. 146-155, Journal of Biological Chemistry, 2000, vol. 275(10), p. 7101-7108, Journal of Biological Chemistry, 2000, vol. 275(14), p. 10300-10307, Journal of Medicinal Chemistry, 2000, vol. 43, p. 995-1010 and Journal of Medicinal Chemistry, 2000, vol. 43, p. 1293-1310 can be mentioned. However, the compound is not limited to the above-mentioned compounds as long as the presence of PTP-LB inhibitory activity can be acknowledged by the above-mentioned measurement methods.

In the present invention, the "PTP-1B inhibitor" means a compound having the above-mentioned "PTP-1B inhibitory activity" and a pharmaceutical composition comprising a compound having "PTP-1B inhibitory activity".

As examples of the test substance selected by any of the method selected from the above-mentioned (1) to (6), the compounds described in, for example, WO02/096880, WO99/58521, WO02/18363, WO99/61435 and the like can be mentioned.

Preferable examples may include the heterocyclic compound of the following formula (I)

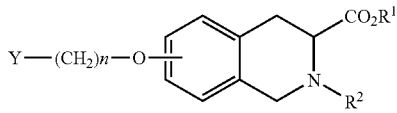

wherein
$R^1$ is a hydrogen atom or $C_{1-6}$ alkyl,
$R^2$ is
 a hydrogen atom,
 —CO—$R^3$
  wherein $R^3$ is $C_{2-6}$ alkyl optionally substituted by halogen(s),
 —CO—C($R^4$)=C($R^4$)—$R^5$
  wherein both $R^4$ are the same or different and each is a hydrogen atom or $C_{1-4}$ alkyl, and $R^5$ is $C_{1-8}$ alkyl, $C_{2-8}$ alkenyl, aryl or aromatic heterocycle,
 —CO—C≡C—$R^6$
  wherein $R^6$ is $C_{1-8}$ alkyl,

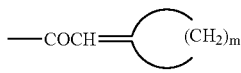

wherein m is an integer of 2-7, aryl, optionally substituted aryl-$C_{1-3}$ alkyl, $C_{1-6}$ alkyl optionally substituted by halogen(s), $C_{2-6}$ alkenyl, $C_{3-8}$ cycloalkyl or $C_{3-8}$ cycloalkyl-$C_{1-3}$ alkyl,
Y is

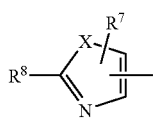

wherein
$R^7$ is a hydrogen atom or $C_{1-4}$ alkyl,
$R^8$ is
 $C_{5-8}$ alkyl, $C_{4-8}$ cycloalkyl, $C_{1-4}$ alkylthio-$C_{1-6}$ alkyl,
 $R^{10}$—C($R^9$)=C($R^9$)—
  wherein both $R^9$ are the same or different and each is a hydrogen atom or $C_{1-4}$ alkyl, and $R^{10}$ is $C_{1-6}$ alkyl optionally substituted by halogen(s), $C_{2-8}$ alkenyl, aryl, aromatic heterocycle, $C_{3-8}$ cycloalkyl, $C_{3-8}$ cycloalkyl-$C_{1-3}$ alkyl, $C_{1-4}$ alkoxy-$C_{1-6}$ alkyl, $C_{1-4}$ alkylthio-$C_{1-6}$ alkyl or $C_{1-6}$ alkyl substituted by $(R^9)_2$N— wherein both $R^9$ are the same or different and each is a hydrogen atom or $C_{1-4}$ alkyl,
 $R^{12}$—CO—N($R^{11}$)—
  wherein $R^{11}$ is a hydrogen atom or $C_{1-4}$ alkyl, and $R^{12}$ is $C_{1-6}$ alkyl or aryl,
 $R^{13}$—Z—
  wherein $R^{13}$ is $C_{1-8}$ alkyl or aryl, and Z is an oxygen atom or a sulfur atom, or

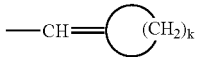

wherein k is an integer of 2-7, and
 X is an oxygen atom or a sulfur atom, or
 $R^{15}$—C($R^{14}$)=N—O—
  wherein $R^{14}$ is a hydrogen atom or $C_{1-4}$ alkyl, and
  $R^{15}$ is aryl or aromatic heterocycle,
Y—$(CH_2)_n$—O— is bonded to the 6- or 7-position of the tetrahydroisoquinoline skeleton, and
n is an integer of 1-4.

More preferable examples may include 2-(2,4-hexadienoyl)-7-[2-(5-methyl-2-(trans-1-penten-1-yl)oxazol-4-yl)ethoxy]-1,2,3,4-tetrahydroisoquinoline-(3S)-carboxylic acid, 2-(2,4-hexadienoyl)-7-{2-[5-methyl-2-(4-methyl-trans-1-penten-1-yl)oxazol-4-yl]ethoxy}-1,2,3,4-tetrahydroisoquinoline-(3S)-carboxylic acid, 2-(2-heptenoyl)-7-{2-[5-methyl-2-(4-methyl-trans-1-penten-1-yl)oxazol-4-yl]ethoxy}-1,2,3,4-tetrahydroisoquinoline-(3S)-carboxylic acid, 2-(2,4-hexadienoyl)-7-{2-[2-(trans-1-hexen-1-yl)-5-methyloxazol-4-yl]ethoxy}-1,2,3,4-tetrahydroisoquinoline-(3S)-carboxylic acid, 2-(2,4-hexadienoyl)-7-{2-[5-methyl-2-(5-methyl-trans-1-hexen-1-yl)oxazol-4-yl]ethoxy}-1,2,3,4-tetrahydroisoquinoline-(3S)-carboxylic acid, 2-(2,4-hexadienoyl)-7-{2-[5-methyl-2-(1-methyl-trans-1-penten-1-yl)oxazol-4-yl]ethoxy}-1,2,3,4-tetrahydroisoquinoline-(3S)-carboxylic acid, 2-(2,4-hexadienoyl)-7-{2-[5-methyl-2-(1-methyl-trans-1-buten-1-yl)oxazol-4-yl]ethoxy}-1,2,3,4-tetrahydroisoquinoline-(3S)-carboxylic acid, 2-(2-hexenoyl)-7-{2-[5-methyl-2-(4-methyl-trans-1-penten-1-yl)oxazol-4-yl]ethoxy}-1,2,3,4-tetrahydroisoquinoline-(3S)-carboxylic acid, 2-(3-butenyl)-7-{2-[5-methyl-2-(4-methyl-trans-1-penten-1-yl)oxazol-4-yl]ethoxy}-1,2,3,4-tetrahydroisoquinoline-(3S)-carboxylic acid, and 7-{2-[5-methyl-2-(4-methyl-trans-1-penten-1-yl)oxazol-4-yl]ethoxy}-2-(4-pentenyl)-1,2,3,4-tetrahydroisoquinoline-(3S)-carboxylic acid, or pharmaceutically acceptable salts thereof.

The compound represented by the formula (I) or a pharmaceutically acceptable salt thereof can be produced according to the disclosure in WO02/096880.

In the present invention, the $C_{1-4}$ alkyl includes linear or branched chain alkyls having 1 to 4 carbon atoms. Examples thereof may include methyl, ethyl, propyl, isopropyl, butyl, isobutyl, sec-butyl, tert-butyl and the like, and preferable examples thereof for $R^4$, $R^7$, $R^9$, $R^{11}$ or $R^{14}$ include methyl, ethyl, propyl and isopropyl.

In the formula (I), the $C_{1-6}$ alkyl includes linear or branched chain alkyls having 1 to 6 carbon atoms. Examples thereof may include methyl, ethyl, propyl, isopropyl, butyl, isobutyl, sec-butyl, tert-butyl, pentyl, isopentyl, neopentyl, hexyl and the like, and preferable examples thereof for $R^1$, $R^{10}$ or $R^{12}$ include methyl, ethyl, propyl, tert-butyl, butyl, isobutyl and isopentyl.

In the formula (I), the $C_{1-8}$ alkyl includes linear or branched chain alkyls having 1 to 8 carbon atoms. Examples thereof may include methyl, ethyl, propyl, isopropyl, butyl, isobutyl, sec-butyl, tert-butyl, pentyl, isopentyl, neopentyl, hexyl, heptyl, octyl and the like, and preferable examples thereof for $R^5$, $R^6$ and $R^{13}$ include methyl, ethyl, propyl, tert-butyl, butyl, pentyl and hexyl.

In the formula (I), the $C_{5-8}$ alkyl includes linear or branched chain alkyls having 5 to 8 carbon atoms. Examples thereof may include pentyl, isopentyl, neopentyl, hexyl, heptyl, octyl and the like, and preferable examples thereof for $R^8$ include pentyl, neopentyl and hexyl.

In the formula (I), in the $C_{2-6}$ alkyl optionally substituted by halogen(s), the halogen includes a chlorine atom, a bromine atom, an iodine atom and a fluorine atom; and the $C_{2-6}$ alkyl includes linear or branched chain alkyls having 2 to 6 carbon atoms, and specific examples thereof may include the aforementioned ethyl, propyl, isopropyl, butyl, isobutyl, tert-butyl, pentyl, neopentyl and hexyl. Examples of the $C_{2-6}$ alkyl substituted by halogen(s) may include 2-chloroethyl, 2-bromoethyl, 2-iodoethyl, 2-fluoroethyl, 2,2-difluoroethyl, 2,2,2-trifluoroethyl, pentafluoroethyl, 2,2,3,3-tetrafluoropropyl, 3,3,3-trifluoropropyl, 4,4,4-trifluorobutyl, 5,5,5-trifluoropentyl, 6,6,6-trifluorohexyl and the like, and preferable examples thereof for $R^3$ include 2-fluoroethyl, 2,2-difluoroethyl, 2,2,2-trifluoroethyl, pentafluoroethyl and 2,2,3,3-tetrafluoropropyl.

In the formula (I), in the $C_{1-6}$ alkyl optionally substituted by halogen(s), the halogen includes a chlorine atom, a bromine atom, an iodine atom and a fluorine atom; and the $C_{1-6}$ alkyl includes linear or branched chain alkyls having 1 to 6 carbon atoms, and specific examples thereof may include the aforementioned methyl, ethyl, propyl, isopropyl, butyl, isobutyl, tert-butyl, pentyl, neopentyl and hexyl. Examples of the $C_{1-6}$ alkyl substituted by halogen(s) may include fluoromethyl, difluoromethyl, trifluoromethyl, chloromethyl, dichloromethyl, trichloromethyl, bromomethyl, dibromomethyl, tribromomethyl, 2-chloroethyl, 2-bromoethyl, 2-iodoethyl, 2-fluoroethyl, 2,2-difluoroethyl, 2,2,2-trifluoroethyl, pentafluoroethyl, 2,2,3,3-tetrafluoropropyl, 3-fluoropropyl, 3,3-difluoropropyl, 3,3,3,2,2-pentafluoropropyl, 3,3,3-trifluoropropyl, 4,4,4-trifluorobutyl, 5,5,5-trifluoropentyl, 6,6,6-trifluorohexyl and the like, and preferable examples thereof for $R^2$ and $R^{10}$ include 3-fluoropropyl, 3,3-difluoropropyl, trifluoromethyl, 2,2,2-trifluoroethyl, 2,2-difluoroethyl, 3,3,3-trifluoropropyl and 3,3,3,2,2-pentafluoropropyl.

In the formula (I), the $C_{3-8}$ cycloalkyl includes cycloalkyls having 3 to 8 carbon atoms. Examples thereof may include cyclopropyl, cyclobutyl, cyclopentyl, cyclohexyl, cycloheptyl and cyclooctyl, and preferable examples thereof for $R^2$ and $R^{10}$ include cyclopropyl, cyclobutyl, cyclopentyl and cyclohexyl.

In the formula (I), the $C_{4-8}$ cycloalkyl includes cycloalkyls having 4 to 8 carbon atoms. Examples thereof may include cyclobutyl, cyclopentyl, cyclohexyl, cycloheptyl, cyclooctyl and the like, and preferable examples thereof for $R^8$ include cyclopentyl and cyclohexyl.

In the formula (I), the $C_{2-8}$ alkenyl includes linear or branched chain alkenyls having 2 to 8 carbon atoms. Examples thereof may include vinyl, 1-propenyl, 2-propenyl, isopropenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl and the like, and preferable examples thereof for $R^5$ and $R^{10}$ include 1-propenyl, 1-butenyl, 1-pentenyl and 1-hexenyl.

In the formula (I), the $C_{2-6}$ alkenyl includes linear or branched chain alkenyls having 2 to 6 carbon atoms. Examples thereof may include vinyl, 1-propenyl, 2-propenyl, isopropenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 1-hexenyl, 2-hexenyl, 3-hexenyl, 4-hexenyl, 5-hexenyl and the like, and preferable examples thereof for R include 3-butenyl, 4-pentenyl and 5-hexenyl.

In the formula (I), the aryl includes phenyl, naphthyl and the like, and preferable examples thereof for $R^2$, $R^5$, $R^{10}$, $R^{12}$, $R^{13}$ and $R^{15}$ include phenyl.

In the formula (I), preferable examples of the aromatic heterocycle for $R^5$, $R^{10}$ and $R^{15}$ may include monocyclic heterocycles and fused heterocycles, each of which comprises at least one heteroatoms selected from the group consisting of an oxygen atom, a nitrogen atom and a sulfur atom. In the present invention, the fused heterocycle has a bicyclic system, and those having heteroatoms in both rings are also encompassed in the fused heterocycle. Preferable examples of the monocyclic heterocycle may include 5- or 6-membered rings. Examples of the heterocycle which constitutes preferable fused heterocycle may include heterocycles having a 5- or 6-membered ring, and examples of the ring comprising no heteroatom, which constitutes preferable fused heterocycle may include 5 or 6-membered rings. Examples of the aromatic heterocycle may include monocyclic heterocycles such as furyl, thienyl, pyridyl, imidazolyl, pyrazolyl, oxazolyl, isoxazolyl, thiazolyl, triazolyl, thiadiazolyl, oxadiazolyl, pyridazinyl, pyrimidinyl and pyrazinyl; and fused heterocycles such as indolyl, isoindolyl, indolinyl, isoindolinyl, indazolyl, benzofuranyl, benzothiophenyl, benzimidazolyl, benzoxazolyl, benzothiazolyl, quinolyl, isoquinolyl, benzoxazinyl, benzothiazinyl, furo[2,3-b]pyridyl, thieno[2,3-b]pyridyl, naphthyridinyl, imidazopyridyl, oxazolopyridyl and thiazolopyridyl, and preferable examples thereof include furyl, thienyl, pyridyl, oxazolyl, thiazolyl, indolyl, indolinyl, benzofuranyl, benzothiophenyl, quinolyl and isoquinolyl.

In the formula (I), the $C_{3-8}$ cycloalkyl-$C_{1-3}$ alkyl includes groups in which the cycloalkyl moiety has 3 to 8 carbon atoms and the alkyl moiety is a linear or branched chain alkyl having 1 to 3 carbon atoms. Examples thereof may include cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, cyclooctylethyl, cyclopropylpropyl, cyclobutylpropyl, cyclopentylpropyl, cyclohexylpropyl, cycloheptylpropyl, cyclooctylpropyl, 1-methylcyclopentyl-1-yl, 1-methylcyclohexyl-1-yl and the like, and preferable examples thereof for $R^2$ and $R^{10}$ include cyclopropylmethyl, cyclopropylethyl, 1-methylcyclopentyl-1-yl, 1-methylcyclohexyl-1-yl, cyclopentylmethyl and cyclohexylmethyl.

In the formula (I), the $C_{1-4}$ alkoxy-$C_{1-6}$ alkyl includes groups in which an alkoxy group having 1 to 4 carbon atoms is bonded to a linear or branched chain alkyl group having 1 to 6 carbon atoms. Examples thereof may include methoxymethyl, ethoxymethyl, propyloxymethyl, isopropyloxymethyl, butoxymethyl, methoxyethyl, ethoxyethyl, propyloxyethyl, butoxyethyl, methoxypropyl, ethoxypropyl, propyloxypropyl, butoxypropyl, methoxybutyl, ethoxybutyl, propyloxybutyl, butoxybutyl, methoxypentyl, ethoxypentyl, propyloxypentyl, butoxypentyl, methoxyhexyl, ethoxyhexyl, propyloxyhexyl, butoxyhexyl and the like, and preferable examples thereof for $R^{10}$ include methoxymethyl, methoxyethyl, ethoxymethyl, propyloxymethyl, isopropyloxymethyl and ethoxyethyl.

In the formula (I), examples of the aryl moiety of the optionally substituted aryl -$C_{1-3}$ alkyl may include phenyl, naphthyl and the like, and examples of the alkyl moiety thereof may include linear or branched chain alkyl having 1 to 3 carbon atoms. Examples of the aryl-$C_{1-3}$ alkyl which is not substituted by the above-mentioned substituent may include benzyl, 1-naphthylmethyl, 2-naphthylmethyl, 2-phenylethyl, 2-(1-naphthyl)ethyl, 2-(2-naphthyl)ethyl, 3-phenylpropyl, 3-(1-naphthyl)propyl, 3-(2-naphthyl)propyl, 1-phenylethyl, 2-phenylpropyl, 1-(1-naphthyl)ethyl, 1-(2-naphthyl)ethyl, 1-(1-naphthyl)propyl, 1-(2-naphthyl)propyl, 2-(1-naphthyl)propyl, 2-(2-naphthyl)propyl and the like, and preferable examples thereof include benzyl, 2-phenylethyl, 3-phenylpropyl, 1-naphthylmethyl and 2-naphthylmethyl. Examples of the substituents may include $C_{1-4}$ alkyl, $C_{1-4}$ alkoxy, hydroxy, a halogen atom (e.g., chlorine, bromine, iodine, fluorine), nitro, amino and the like. Preferable number of the substituents is 1 or 2.

In the formula (I), the $C_{1-4}$ alkylthio-$C_{1-6}$ alkyl includes groups in which the alkyl moiety of the alkylthio moiety is a linear or branched chain alkyl having 1 to 4 carbon atoms and the alkyl moiety is a linear or branched chain alkyl having 1 to 6 carbon atoms. Examples thereof may include methylthiomethyl, methylthioethyl, methylthiopropyl, methylthiobutyl, methylthiopentyl, methylthiohexyl, ethylthiomethyl, ethylthioethyl, ethylthiopropyl, ethylthiobutyl, ethylthiopentyl, ethylthiohexyl, propylthiomethyl, propylthioethyl, propylthiopropyl, propylthiobutyl, propylthiopentyl, propylthiohexyl, isopropylthiomethyl, butylthiomethyl, butylthioethyl, butylthiopropyl, butylthiobutyl, butylthiopentyl, butylthiohexyl and the like, and preferable examples thereof for $R^8$ and $R^{10}$ include methylthiomethyl, methylthioethyl, ethylthiomethyl, ethylthioethyl, isopropylthiomethyl and methylthiopropyl.

In the formula (I), the $C_{1-6}$ alkyl substituted by $(R^9)_2N$— (wherein both $R^9$ are the same or different and each is a hydrogen atom or $C_{1-4}$ alkyl) includes alkyl moieties in which an alkyl having 1 to 6 carbon atoms is substituted by the above-mentioned $(R^9)_2N$—. Examples of such $C_{1-6}$ alkyl substituted by $(R^9)_2N$— for $R^{10}$ may include aminomethyl, methylaminomethyl, dimethylaminomethyl, aminoethyl, methylaminoethyl, dimethylaminoethyl, aminopropyl, dimethylaminopropyl, aminobutyl, aminopentyl, aminohexyl, diethylaminomethyl, diethylaminoethyl, ethylaminoethyl and the like, and preferable examples thereof include aminomethyl, methylaminomethyl, dimethylaminomethyl, aminoethyl, methylaminoethyl, dimethylaminoethyl, aminopropyl and dimethylaminopropyl.

In the formula (I), $R^1$ is preferably a hydrogen atom.

In the formula (I), preferable examples of $R^2$ may include —CO—C($R^4$)=C($R^4$)—$R^5$ (wherein $R^4$ is a hydrogen atom, and $R^5$ is $C_{1-8}$ alkyl or $C_{2-8}$ alkenyl), —CO—C≡C—$R^6$ (wherein $R^6$ is $C_{1-8}$ alkyl) and $C_{2-6}$ alkenyl.

In the formula (I), it is preferable that Y—(CH$_2$)n-O— bonds to the 7-position of the tetrahydroisoquinoline skeleton. Furthermore, in Y—(CH$_2$)n-O—, n is preferably 2. Y is preferably a group represented by the formula

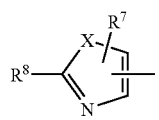

wherein each symbol is as defined above. More preferable examples of Y may include groups represented by the above-mentioned formula wherein (1) $R^7$ is a hydrogen atom or $C_{1-4}$ alkyl, and $R^8$ is $R^{10}$—C($R^9$)=C($R^9$)— (wherein both $R^9$ are the same or different and each is a hydrogen atom or $C_{1-4}$ alkyl, and $R^{10}$ is $C_{1-6}$ alkyl, $C_{2-8}$ alkenyl or aryl),
(2) $R^7$ is a hydrogen atom or $C_{1-4}$ alkyl, and $R^8$ is $R^{13}$—Z— (wherein $R^{13}$ is $C_{1-8}$ alkyl or aryl, and Z is a sulfur atom),
(3) $R^7$ is a hydrogen atom or $C_{1-4}$ alkyl, and $R^8$ is $C_{5-8}$ alkyl or $C_{4-8}$ cycloalkyl, and
(4) $R^7$ is a hydrogen atom or $C_{1-4}$ alkyl, and $R^8$ is $R^{10}$—C($R^9$)=C($R^9$)— (wherein $R^9$ is a hydrogen atom, and $R^{10}$ is $C_{3-8}$ cycloalkyl).

Further preferable examples of Y may include groups represented by the above-mentioned formula wherein (5) $R^7$ is $C_{1-4}$ alkyl, $R^8$ is $R^{10}$—C($R^9$)=C($R^9$)— (wherein both $R^9$ are the same or different and each is a hydrogen atom or $C_{1-4}$ alkyl, and $R^{10}$ is $C_{1-6}$ alkyl) and X is an oxygen atom, and
(6) $R^7$ is a $C_{1-4}$ alkyl, $R^8$ is $R^{10}$—C($R^9$)=C($R^9$)— (wherein $R^9$ is a hydrogen atom, and $R^{10}$ is aryl) and X is an oxygen atom.

In the formula (I), X for Y is preferably an oxygen atom.

In the formula (I), particularly preferable Y may include any of the groups selected from the (a) to (n) as shown below.

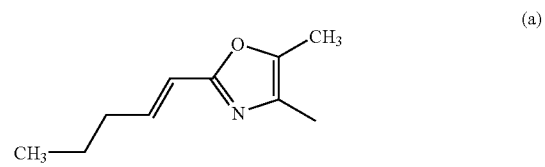

(a)

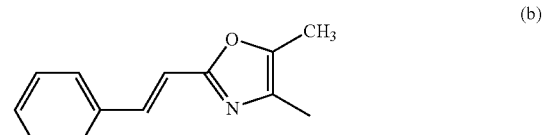

(b)

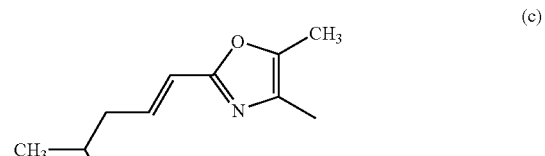

(c)

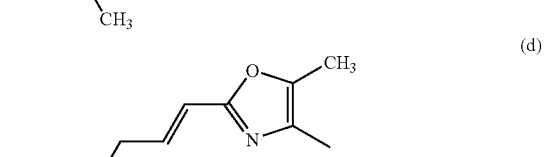

(d)

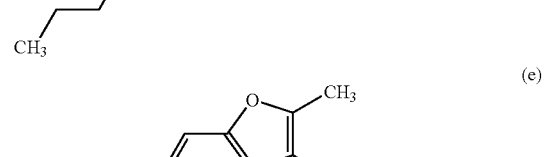

(e)

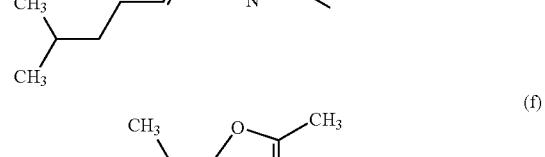

(f)

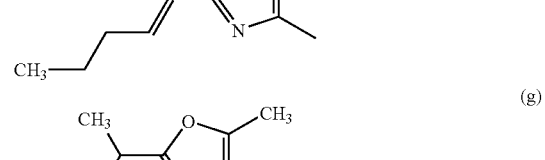

(g)

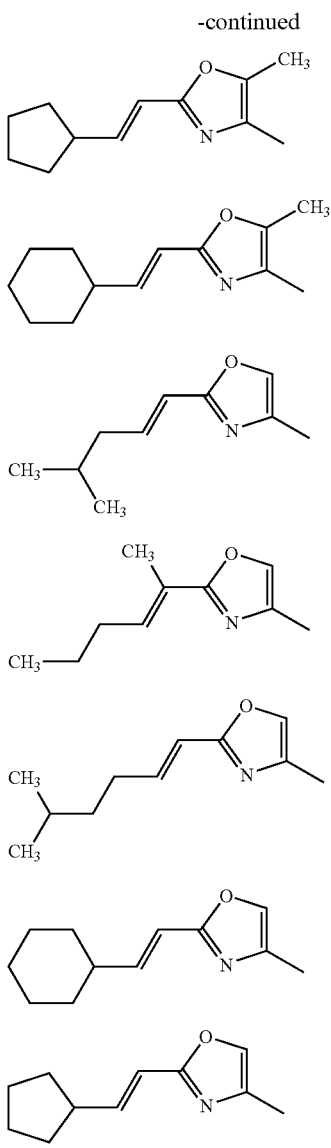

The compound represented by the formula (I) encompasses stereoisomers, since the carbon at the 3-position of the 1,2,3,4-tetrahydroisoquinoline ring is an asymmetric carbon. The most preferable configuration is

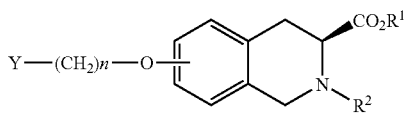

wherein $R^1$, $R^2$, Y and n are as defined above.

Furthermore, in the formula (I), where $R^2$ is —CO—C($R^4$)=C($R^4$)—$R^5$ (wherein $R^4$ and $R^5$ are defined as above), $R^8$ is $R^{10}$—C($R^9$)=C($R^9$)— (wherein $R^9$ and $R^{10}$ are defined as above) or Y is $R^{15}$—C($R^{14}$)=N—O— (wherein $R^{14}$ and $R^{15}$ are defined as above), stereoisomers (Z-form and E-form) at the double bond moiety or the oxime moiety exist, and both isomers are also encompassed in the present invention.

The compound of the present invention may form a pharmaceutically acceptable salt. The heterocyclic compound (I) can be converted to a pharmaceutically acceptable salt thereof by a method known per se.

When the compound of the present invention has a basic group, an acid addition salt can be formed. An acid to form such acid addition salt is not particularly limited as long as it can form a salt with a basic moiety and is a pharmaceutically acceptable acid. As such acid, inorganic acids such as hydrochloric acid, sulfuric acid, phosphoric acid, nitric acid and the like, and organic acids such as oxalic acid, fumaric acid, maleic acid, citric acid, tartaric acid, methanesulfonic acid, toluenesulfonic acid and the like can be mentioned.

When the compound of the present invention has an acidic group such as carboxyl group and the like, for example, alkali metal salt (e.g., sodium salt, potassium salt and the like), alkaline earth metal salt (e.g., calcium salt, magnesium salt and the like), organic base salts (e.g., tert-butylamine salt, triethylamine salt, dicyclohexylamine salt, ethanolamine salt, pyridine salt and the like) and the like can be formed.

A pharmaceutical composition comprising the compound of the present invention or a pharmaceutically acceptable salt thereof can contain additives and the like. As the additive, for example, excipients (e.g., starch, lactose, sugar, calcium carbonate, calcium phosphate etc.), binders (e.g., starch, gum arabic, carboxymethylcellulose, hydroxypropylcellulose, crystalline cellulose etc.), lubricants (e.g., magnesium stearate, talc etc.), disintegrants (e.g., carboxymethylcellulose calcium, talc etc.) and the like can be mentioned.

After mixing with the above-mentioned various components, the mixture can be processed to give, for example, preparations for oral administration such as capsule, tablet, fine granules, granules, dry syrup and the like or preparations for parenteral administration such as injection, suppository and the like by a means known per se.

While the dose of the compound of the present invention or a pharmaceutically acceptable salt thereof varies depending on the subject of administration, condition and other factors, for oral administration to an adult, for example, a dose of about 1-500 mg is administered to patients with diabetes, diabetic complications or hyperlipidemia about 1-3 times a day.

The compound of the present invention and a pharmaceutically acceptable salt thereof show superior hypoglycemic action, hypoglycemic action, insulin resistance improving effect and PPAR activation activity in mammals (human, horse, bovine, dog, cat, rat, mouse, hamster and the like), are useful as anti-hyperglycemia, anti-hyperlipidemia, insulin sensitizer, therapeutic agent for diabetes, therapeutic agent for diabetic complications, impaired glucose tolerance improving agent, anti-arteriosclerosis agent, anti-obesity agent, anti-inflammatory agent, agent for the prophylaxis or treatment of PPAR-mediated diseases, agent for the prophylaxis or treatment of PTP-mediated diseases and agent for the prophylaxis or treatment of X syndrome. That is, the compound of the present invention and a pharmaceutically acceptable salt thereof are useful for the prophylaxis and treatment of diabetes, diabetic complications, hyperlipidemia, arteriosclerosis, hyperglycemia, diseases caused by insulin resistance impaired glucose tolerance, diseases caused by insulin resistance, obesity, inflammation, PPAR-mediated diseases, PTP-mediated diseases and X syndrome.

EXAMPLES

The present invention is further explained in detail by referring to the following Examples and Reference Examples, which are not to be construed as limitative.

Rosiglitazone used in Examples is a commercially available PPARγ activator, which is described in U.S. Pat. No. 5,002,953 and can be produced by the method of the publication.

Example 1

Determination of PTP-1B Inhibitory Activity (1) Preparation of PTP-1B Enzyme

The nucleotide sequence of human PTP-1B cDNA is described in SEQ; ID NO. 1. It is registered in the GenBank (gene database) under the Registration No. NM 002827, and the amino acid sequence is described in SEQ; ID NO. 2. Of these, to obtain a protein encoding the 1st to 321st amino acids including an active region, the total RNA was extracted from cell line HepG2 derived from human liver tumor and, using this as a template, complementary DNA (cDNA) was obtained by reverse transcription polymerase chain reaction (RT-PCR) method. The cDNA was incorporated into an *Escherichia coli* expression vector, and expressed by *Escherichia coli* and purified. The detail is shown in the following.

(1-1) Obtainment of Total RNA from Cell Line HepG2

The cell line HepG2 (American Type Culture Collection HB-8065) was purchased from Dainippon Pharmaceutical Co., Ltd., and cultured in a tissue culture flask (culture area 75 $cm^2$ manufactured by BD Biosciences). As a medium, Dulbecco's Modified Eagle medium (Gibco D-MEM, manufactured by Invitrogen) supplemented with fetal bovine serum (manufactured by Highclone) at a volume ratio of 10%, and an antibiotic solution [Antibiotic Antimycotic Solution, stabilized (100×), manufactured by Sigma] at a volume ratio of 1%, was used.

The cells were cultured in a carbon dioxide incubator at 37° C., under 95% $CO_2$ for 3 days. When the cells reached almost semiconfluent, the medium in the flask was removed by suction. Ice-cooled phosphate-buffered saline (10 ml, Gibco Dulbecco's Phosphate-Buffered Saline, manufactured by Invitrogen) was added to wash the cells and the saline was removed by suction. Thereafter, 7.5 ml of a trizol reagent (Gibco TRIZOL reagent, manufactured by Invitrogen) was added to the cells in the flask, pipetting was repeated and the mixture was left standing at room temperature for about 5 min for cell lysis.

This cell lysate was subjected to isopropyl alcohol precipitation and the like generally following the instructions of the trizol reagent to obtain RNA precipitate, which was dissolved in pure water and preserved in a freezer at about −20° C. The RNA solution then was 0.22 ml, and a part thereof was taken and 100-fold diluted with pure water to give a sample, which showed an absorbance at 260 nm of 0.562. By the calculation assuming the presence of 39.5 μg/ml of RNA for absorbance of 1, the yield of the total RNA was 0.562×100×39.5×0.22=488 μg.

(1-2) PTP-1B cDNA Cloning

By reference to the Puius, Y A et al. method (Proceedings of the national academy of science of the USA, vol. 94, 13420-13425, 1997), as the primer for PCR amplification of PTP-1B cDNA, chemical synthesis of the following two oligodeoxynucleotides was committed to Amersham Pharmacia Biotech (Tokyo).

5'-agctggatccatatggagatggaaaaggagtt-3' (primer No. 1: SEQ; NO. 3),

5'-acgcgaattcttaattgtgtggctccaggattcg-3' (primer No.2: SEQ; NO. 4).

Then, using HepG2 total RNA obtained earlier as a template and the above-mentioned primers No. 1 and No. 2 as primers, amplification of PTP-1B cDNA was performed by RT-PCR method using Ready-To-Go RT-PCR Beads (Amersham Pharmacia Biotech). The reaction product was applied to 1.5% agarose electrophoresis, an amplified fragment was cleaved out, purified and cloned to pCR2.1 vector plasmid (manufactured by Invitrogen). The amplified DNA fragment contained a nucleotide sequence of nucleotide No. 73 to nucleotide No. 1035 in SEQ; NO. 1.

The base sequence of PTP-1B cDNA cloned to pCR 2.1 vector plasmid was examined, and, of the plasmid clones having a correct base sequence fragment, a clone wherein PTP-1B complementary DNA had been inserted in such direction that BamHI cleavage site that pCR 2.1 originally has was located in the downstream of 3' was selected, which was treated with restriction enzymes NdeI and BamHI to produce a fragment containing PTP-1B cDNA. The fragment was purified by agarose electrophoresis, inserted into *Escherichia coli* expression vector pET-11c (manufactured by Novagen, Inc.) treated with NdeI and BamHI and cloned. From the above, pET-hPTP1B (1-321) was constructed, which is a plasmid that expresses a polypeptide consisting of amino acid No. 1 to amino acid No. 321 of human PTP-1B SEQ; ID No.2, in *Escherichia coli*.

(1-3) Expression of Human PTP-1B (1-321) by *Escherichia coli* and Purification Thereof.

Plasmid pET-hPTP1B (1-321) was transformed to *Escherichia coli* BL21 DE3 strain (manufactured by Novagen, Inc.) to give ampicillin (100 μg/ml) resistant cells. They were cultured in 2×YT medium (2 L, yeast extract 1%, tryptone 1.6%, sodium chloride 0.5%) containing ampicillin (100 μg/ml) at 37° C. and, when the OD600 nm reached 0.6, IPTG (Isopropyl β-D-Thiogalactoside) was added to 0.1 mM, and the cells were further cultured at 37° C. for 6 hr to induce expression of recombinant protein.

The cells were collected by centrifugation (6,000 rpm, 15 min., 4° C.) and suspended in 30 ml of a lysis buffer [20 mM Tris HCl (pH 7.5), 1 mM DTT, 1 mM EDTA, Complete protease inhibitor cocktail manufactured by Roche Diagnostics, 1 tablet/50 ml]. The suspension was divided into four and placed in four 50 ml centrifuge tubes (manufactured by Falcon, 2070 tube) and centrifuged at 5,000 rpm, 4° C. for 15 min. The supernatant was discarded, and 5 ml of a lysis buffer was added to each tube to suspend the cells. The suspension was preserved in a freezer at −80° C.

To one of the cryopreserved cell suspension tubes (culture medium 500 ml) was added 22 ml of a lysis buffer and the cells were disrupted by ultrasonication. The disrupt solution was centrifuged (14,000 rpm, 90 min, 4° C.) and the supernatant was passed through a 0.45 μm filter. The filtrate was adsorbed onto a HiTrap Q FF column (column volume about 5 ml, Amersham Pharmacia Biotech), and the column was washed with buffer A [10 mM Tris HCl (pH 7.5), 1 mM DTT, 1 mM EDTA] and then eluted with linear NaCl concentration gradient in buffer A and buffer A containing 1M NaCl.

The eluted fractions having a calculated NaCl concentration ranging approximately from 0.2M to 0.33M was detected to have a band of a protein with a molecular weight of about 37,000 by SDS-PAGE, and PTP-1B enzyme activity was observed. The active fractions (12.5 ml) were collected, dialyzed against buffer B [10 mM MES (pH 6.5), 1 mM DTT, 1 mM EDTA] overnight, adsorbed to a HiTrap CM FF column (column volume about 1 ml, Amersham Pharmacia Biotech), washed with buffer B and eluted with linear NaCl concentration gradient in buffer B and buffer B containing 1M NaCl.

The eluted fractions having a calculated NaCl concentration ranging approximately from 0.25M to 0.4M were detected to have a band of a protein with a molecular weight of about 37,000 by SDS-PAGE, and PTP-1B enzyme activity was observed. The active fractions (3 ml) were collected, applied to a HiLoad 26/60 Superdex 75 pg column (column volume about 320 ml, Amersham Pharmacia Biotech) and gel filtration using buffer C [10 mM Tris-HCl (pH 7.5), 3 mM DTT, 0.2 mM EDTA]. The peak regions (18 ml) of eluted solution were collected and concentrated by centrifugation using Centriprep-10 (Millipore).

The solution of the PTP-1B protein [PTP-1B (1-321)] obtained was about 0.7 ml, the concentration was 25 mg/ml, and the yield was 18 mg. In a mass analysis using a mass spectrometer Q-TOF2 manufactured by Micromass, observed mass was 37310.5±4.3 Da relative to theoretical mass of 37312.75 Da.

(2) Determination of PTP-1B Enzyme Inhibitory Activity

As the substrates for PTP-1B enzyme reaction, synthetic peptides consisting of the following amino acid sequence: Thr-Arg-Asp-Ile-Tyr ($PO_4$)-Glu-Thr-Asp-Tyr ($PO_4$)-Tyr ($PO_4$)-Arg-Lys (SEQ; NO. 5), wherein 3 tyrosines had been all phosphorylated, were used (synthesis committed to Shimadzu Scientific Research Inc. (Chiyoda-ku, Tokyo)). [According to the amino acid numbers based on the report of Ullrich et al. (Nature, vol. 313, pages 756-761, 1985), this amino acid sequence corresponds to Nos. 1142-1153 of insulin receptor, and corresponds to Nos. 1169-1180 in the amino acid sequence of the insulin receptor precursor registered in Genbank No. X02160.]

This peptide substrate and a PTP-1B enzyme were reacted and the enzyme activity was determined by quantitation of inorganic phosphoric acid released from the substrate by the reaction. The decreased enzyme activity in the presence of a test compound during the enzyme reaction was taken as the enzyme inhibitory activity. Specifically, the following method was performed.

A peptide substrate (synthesis committed to Shimadzu Scientific Research Inc.) was dissolved in a buffer (20 mM imidazole (pH 7.0), 50 mM NaCl, 5 mM DTT and 2.5 mM EDTA) to 300 µM, and cryopreserved.

The PTP-1B solution obtained earlier was diluted with a buffer (20 mM imidazole (pH 7.0), 50 mM NaCl, 5 mM DTT, 2.5 mM EDTA, and 0.05% Nonidet P-40) to 200 ng/ml.

A 96 well microtiter plate [Costar 3695 (half area) Corning] was used and a buffer [39 µl, 20 mM imidazole (pH 7.0), 50 mM NaCl, 5 mM DTT, 2.5 mM EDTA], a PTP-1B enzyme solution (5 µl), and a solution (5 mM, 1 µl) of a test compound in dimethylsulfoxide (DMSO) were added to each well. As a control, solvent (DMSO, 1 µl) was added instead of the DMSO solution of test compound. After preincubation at 37° C. for about 10 min, a peptide substrate solution (300 µM, 5 ml) was added and the mixture was incubated at 37° C. for 10 min.

For quantitation of released inorganic phosphoric acid, malachite green solution (90 µl, manufactured by BIOMOL Research Laboratories, Inc.) was added to each well, and the mixture was left standing at room temperature for about 10 min and the absorbance at 650 nm was measured with a microplate reader. Linearity was mostly observed between the absorbance and the phosphoric acid concentration generally within the absorbance range of from 0.05 to 0.6 (phosphoric acid from about 0.05 to 1.0 nM/well) under these conditions.

The PTP-1B inhibitory activity of the test compound was obtained by the following calculation formula.

Inhibitory activity (%)={{absorbance [in the presence of each compound (100 µM)]}/[absorbance (control)]}×100

The obtained results are shown in Table 1.

TABLE 1

| Reference Example Nos. or compound name | inhibitory activity (%) |
| --- | --- |
| Rosiglitazone | <10 |
| 40 | 90 |
| 27 | 88 |
| 24 | 92 |
| 33 | 92 |
| 30 | 96 |
| 22 | 95 |
| 66 | 80 |
| 83 | 82 |

From Table 1, it is clear that the compound represented by the formula (I) has superior PTP-1B enzyme inhibitory activity. In contrast, rosiglitazone, a known PPARγ activator, scarcely has PTP-1B enzyme inhibitory activity.

Example 2

Determination of PPARγ Activation Ability

As a method for determining the ability of a compound to activate PPARγ (hereinafter PPARγ activation ability), a test by a reporter assay was performed with reference to the report of Kliewer et al. (Journal of Biological Chemistry, 1995, vol. 270(22), p. 12953-12956). The detail is shown below.

(1) Preparation of PPARγ Receptor Expression Plasmid

With reference to the report of Kliewer, a gene expressing a GAL4-PPARγ receptor, wherein human PPARγ ligand binding site (corresponding to about 300 amino acids on carboxy terminal) is bound with a DNA binding site (corresponding to 147 amino acids on amino terminal region) of yeast transcription factor GAL4, was prepared.

The base sequence human PPARγ gene is described in the gene database GenBank as Accession No. X90563, and the amino acid sequence is described as SEQ; NO. 6.

(1-1) Obtainment of Total RNA From Cell Line HepG2

In the same manner as in the method described in the aforementioned determination of PTP-1B inhibitory activity, and (1-1) Obtainment of total RNA from cell line HepG, human liver tumor-derived cell line HepG2 (American Type Culture Collection HB-8065) purchased from Dainippon Pharmaceutical Co., Ltd. was cultured, and the total RNA was extracted using a trizol reagent (Gibco Trizol Reagent, manufactured by Invitrogen) following the instructions attached thereto.

(1-2) Cloning of cDNA to PPARγ Ligand Binding Site

As a primer for amplification by reverse transcription polymerase chain reaction (hereinafter RT-PCR) method of cDNA on the PPARγ ligand binding site, the following two deoxyoligo nucleotides (primers No. 3 and No. 4) designed based on the human PPARγ gene sequence were chemically synthesized using Beckman Oligo 1000 (manufactured by Beckman).

```
5'-ggatccataatgccatcaggtttgggcgg-3'
(primer No. 3, SEQ; NO. 7)

5'-aagcttctagtacaagtccttgtagatctc-3'
(primer No. 4, SEQ; NO. 8)
```

Using HepG2 total RNA obtained earlier as a template and the above-mentioned primers No. 3 and No. 4 as primers, PPARγ cDNA was amplified by RT-PCR method using Ready-To-Go RT-PCR Beads (manufactured by Amersham Pharmacia Biotech). The reaction product was applied to 1.5% agarose electrophoresis, an amplified about 900 base pair band was cleaved out and purified, and cloned to plasmid pCRII (manufactured by Invitrogen). The amplified DNA fragment was considered to contain a sequence encoding human PPARγ ligand binding site, or Nos. 175-475, and have a nucleotide sequence depicted in SEQ; NO. 9, which comprised a restriction enzyme BamHI cleavage site and a restriction enzyme HindIII site on the 5' side and the 3' side, respectively. The nucleotide sequence was confirmed and a plasmid clone correctly containing the sequence depicted in sequence No. 9 was selected.

(1-3) Obtainment of Plasmid pM-PPARγ

Then, the selected plasmid was treated with restriction enzymes BamHI and HindIII to give an about 900 base pair fragment containing a gene of a PPARγ ligand binding site. This was inserted into a BamHI-HindIII site of a plasmid pM (manufactured by CLONTECH Laboratories, Inc.) having a gene of a yeast transcription factor GAL4 DNA binding site to perform cloning.

The plasmid pM-PPARγ obtained by the above-mentioned operation contains a nucleotide sequence depicted in SEQ; NO. 10, and is a gene capable of expressing in mammalian cells, a GAL4-PPARγ chimeric receptor containing amino acid Nos. 1-147 of yeast transcription factor GAL4 on the amino terminal and Nos. 175-475 and termination codon of human PPARγ on the carboxy terminal, and having an amino acid sequence depicted in SEQ; NO. 11.

(2) Determination of PPARγ Activation Ability

The plasmid pM-PPARγ obtained earlier, and plasmid pFR-Luc purchased from STRATAGENE CLONING SYSTEMS were each dissolved in desalted water to a concentration of 1 mg/1 ml.

A human fetal kidney-derived cell line HEK293 (American Type Culture Collection CRL-1573) was sown in a 75 cm² culture flask, and cultured in Dulbecco's Modified Eagle medium containing 10% fetal bovine serum (hereinafter a medium) under the conditions of 37° C., 5% $CO_2$ until it reached nearly 80% confluent.

Using 7.5 μg of plasmid pM-PPARγ and 7.5 μg of plasmid pFR-Luc, both per flask, as well as a FuGENE6 transfection reagent (manufactured by Rosch Diagnostics) the plasmids were transfected to HEK293 cells and cultured overnight.

The next day, the cells were treated with trypsin and recovered. A 96 well plate coated with poly-L-lysine (IWAKI poly-L-lysine coated 96 well plate, manufactured by ASAHI TECHNOGLASS) was prepared, the cells were sown at about 50,000 cells/well, 90 μl, using the medium and cultured overnight.

The test compound was dissolved in DMSO at a concentration of 10 mM. This was diluted 1,000-fold with the medium, and 10 μl therefrom was added to the well in which cells were growing. The treatment concentration in the cell was 1 μM. After the addition, the cells were cultured overnight.

The next day, the medium was removed, and the cells were washed with phosphate buffered saline containing 1 mM magnesium and 1 mM calcium chloride. PicaGene LT FR manufactured by Wako Pure Chemical Industries, Ltd. was diluted 2-fold with the same saline and the solution was added to each well by 200 μl. After standing the mixture for about 1 hr, it was stirred and 180 μl thereof was taken from each well and placed in a white 96 well plate (OptiPlate 96, manufactured by Packard), applied to TopCount (manufactured by Packard) and the amount of luminescence of each well was measured for 6 seconds.

The PPARγ activation ability of the test compound was determined by the following calculation formula:

PPARγ activation ability=(amount of luminescence [in the presence of each compound (1 μM)]}/ [amount of luminescence (control)]

When the value calculated by the above formula is greater than 1, the test compound is considered to have PPARγ activation ability.

The obtained results are shown in Table 2.

TABLE 2

| Reference Example No. or compound name | PPARγ activation ability |
| --- | --- |
| rosiglitazone | 10.2 |
| 40 | 5.4 |
| 27 | 5.9 |
| 24 | 9.4 |
| 33 | 6.5 |
| 30 | 6.2 |
| 22 | 5.1 |
| 66 | 3.0 |
| 83 | 3.1 |
| control | 1 |

From Table 2, it is clear that rosiglitazone and the compound represented by the formula (I) both have PPARγ activation ability.

Example 3

Expression suppressive action on edema and the like by compound A ((2-(2,4-hexadienoyl)-7-{2-[5-methyl-2-(5-methyl-trans-1-hexen-1-yl)oxazol-4-yl]ethoxy}-1,2,3,4-tetrahydroisoquinoline-(3S)-carboxylic acid tert-butyl amine salt: Reference Example 30) having PTP-1B inhibitory activity and PPARγ activation activity For the test, male Zucker Fatty rats (6-week-old, Japan SLC) were used. During the acclimation period for 1 week and test period, feed (FR-2 (Funabashi Farm)) and water were freely given.

Blood was taken from the tail vain using a heparin-coated hematocrit tube and an EDTA-added hematocrit tube, and a part thereof was preserved as a whole blood and the rest was centrifuged and plasma was collected and subjected to the measurement of biochemical parameter (insulin). For insulin measurement, a rat Insulin RIA kit (US Linco) was used, and all the samples were collectively measured after the completion of administration. The whole blood sample was subjected to the measurement of blood cell parameters (erythrocyte concentration, hemoglobin concentration) using an automatic blood cell measurement apparatus (KX-21N, Sysmex Corporation).

At the beginning of the test, blood was taken from all the rats, and randomly grouped to make the parameters (body weight, erythrocyte, hemoglobin and the like) almost the same. The animals were divided into a control group, a compound A (0.3, 1, 3, 10, 30 mg/kg, po, once-daily) administration group, and a rosiglitazone (0.3, 1, 3, 10, 30 mg/kg, po, once-daily) administration-group, and the administration was continued for 2 consecutive weeks (each group n=5). The start of the administration was day 0, and the animals were fasted for about 16 hr from the evening of day 13. Blood was taken and measured for each parameter.

Figure 2:
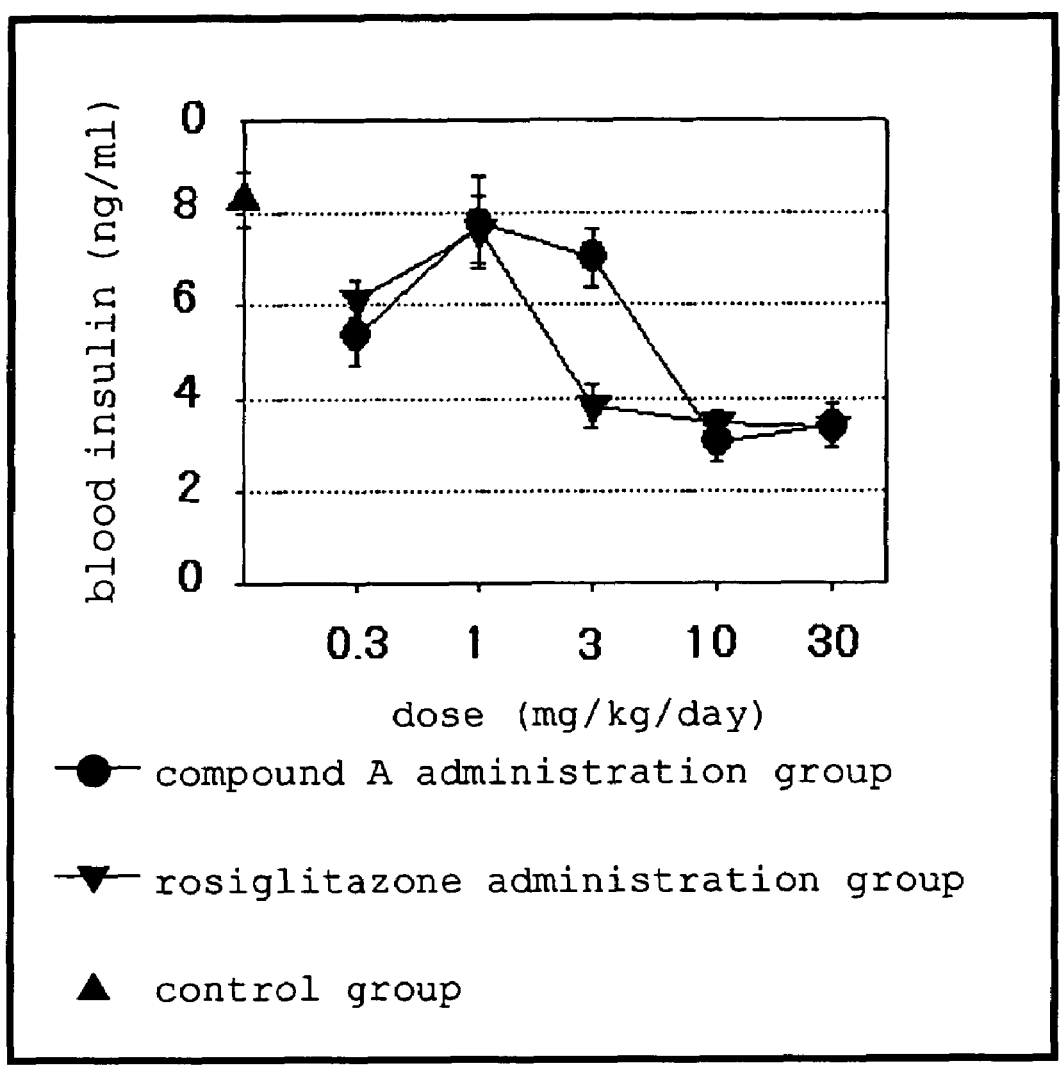
FIG. 2 shows a graph plotting a blood insulin concentration on the vertical axis, and a dose of the test compound on the transverse axis.
Figure 3:
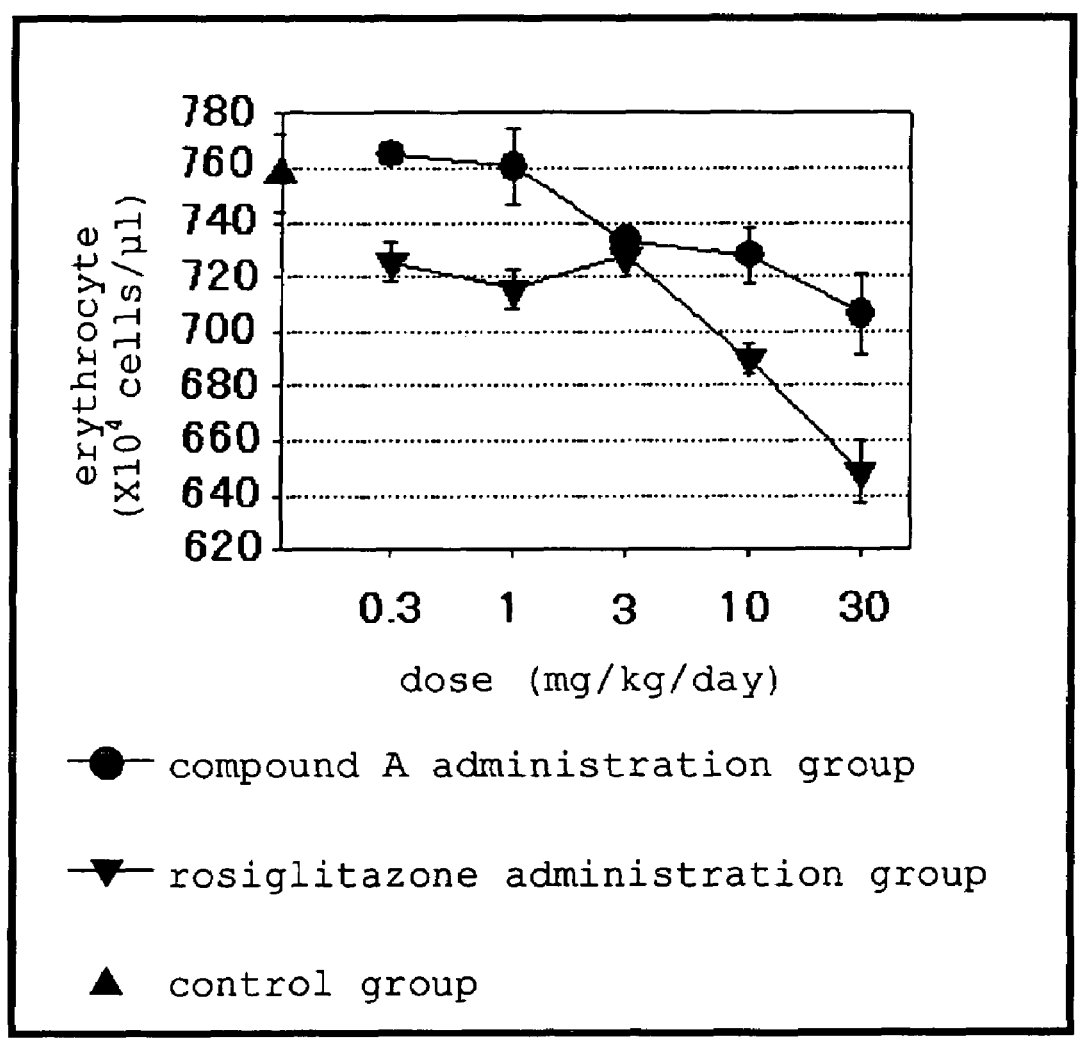
FIG. 3 shows a graph plotting an erythrocyte concentration on the vertical axis, and a dose of the test compound on the transverse axis.

The results are shown in FIGS. 1-3.

FIG. 1 shows a graph plotting a hemoglobin concentration on the vertical axis, and a dose of the test compound on the transverse axis.

FIG. 2 shows a graph plotting a blood insulin concentration on the vertical axis, and a dose of the test compound on the transverse axis.

FIG. 3 shows a graph plotting an erythrocyte concentration on the vertical axis, and a dose of the test compound on the transverse axis.

As is clear from FIG. 1, FIG. 2 and FIG. 3, at 30 mg/kg, the compound A administration group showed an insulin lowering action equivalent to that of the rosiglitazone (commercially available PPARγ activator) administration group. In other words, compound A can be said to have an efficacy of the same level as or above the level of rosiglitazone at the same dose. Examination of the results of hemoglobin and erythrocyte of the compound A administration group reveals that, at 30 mg/kg, the concentrations of the hemoglobin and erythrocyte were somewhat lower than those of the control group, but maintained at a remarkably high level as compared to the rosiglitazone administration group. In other words, it is appreciated that blood dilution (decrease in the concentrations of hemoglobin and erythrocyte) considered to generally occur due to a PPARγ activator such as rosiglitazone is markedly suppressed in the compound A administration group. Dilution of blood is caused by an increase in the plasma amount, and a long-term increase in the redundant body fluids (plasma, hydrothorax and the like) is known to cause side effects such as edema, heart weight gain, cardiac enlargement, hydrothorax and the like.

From the above, it is clear that compound A is almost free of side effects (particularly blood dilution) characteristic of PPARγ activators, even though it has an efficacy of the same level as or not less than that of conventional PPARγ activators.

As the reason for the absence of side effects characteristic of PPARγ activators despite the strong PPARγ activation activity, it can be mentioned that the compound of the present invention concurrently has PPARγ activation activity and PTP inhibitory activity. It is considered that the effect of attenuation of side effects caused by PPARγ activation is attributable to the addition of an insulin resistance improving effect as a result of inhibition of PTP-1B.

Therefore, a compound having PPARγ activation activity and PTP-1B inhibitory activity is useful as a highly safe, superior drug for diabetes.

REFERENCE EXAMPLES

Reference Example 1

2-(2-heptenoyl)-7-[2-(5-methyl-2-(trans-1-penten-1-yl)oxazol-4-yl)ethoxy]-1,2,3,4-tetrahydroisoquinoline-(3S)-carboxylic Acid Sodium Salt (1) Methyl 2-(2-heptenoyl)-7-hydroxy-1,2,3,4-tetrahydroisoquinoline-(3S)-carboxylate (500 mg) and 2-[5-methyl-2-(trans-1-penten-1-yl)oxazol-4-yl]ethyl methanesulfonate (650 mg) were dissolved in toluene (15 ml), potassium carbonate (650 mg) and tetraethylammonium fluoride hydrate (100 mg) were added, and the mixture was stirred at 80° C. for 10 hr. Ethyl acetate (50 ml) was added to the reaction mixture, and the mixture was washed with water (30 ml) and saturated brine (30 ml), and dried over $Na_2SO_4$. The solvent was evaporated under reduced pressure. The obtained residue was purified by silica gel column chromatography to give methyl 2-(2-heptenoyl)-7-[2-(5-methyl-2-(trans-1-penten-1-yl)oxazol-4-yl)ethoxy]-1,2,3,4-tetrahydroisoquinoline-(3S)-carboxylate (620 mg).

$^1$H-NMR (CDCl$_3$) δ (ppm); 0.95 (6H, br-t), 1.15-1.75 (6H, m), 2.00-2.45 (4H, m), 2.27 (3H, s), 2.87 (2H, t, J=6.8 Hz), 3.00-3.30 (2H, m), 3.60 (3H, s), 4.15 (2H, t, J=6.8 Hz), 4.50-5.70 (3H, m), 6.18 (1H, d, J=15.8 Hz), 6.35-7.20 (5H, m), 7.04 (1H, d, J=8.2 Hz).

(2) The compound (200 mg) obtained in the above-mentioned (1) was dissolved in a mixed solvent (5 ml) of tetrahydrofuran-methanol (3:1), 1M aqueous lithium hydroxide solution (1.2 ml) was added, and the mixture was stirred at 50° C. for 30 min. The mixture was acidified with 10% aqueous citric acid, and the solution was concentrated under reduced pressure. The precipitated gum-like substance was extracted with ethyl acetate (20 ml), and the ethyl acetate layer was washed with saturated brine (10 ml), and dried over $Na_2SO_4$. The ethyl acetate was evaporated under reduced pressure. The obtained residue was purified by silica gel column chromatography to give 2-(2-heptenoyl)-7-[2-(5-methyl-2-(trans-1-penten-1-yl)oxazol-4-yl)ethoxy]-1,2,3,4-tetrahydroisoquinoline-(3S)-carboxylic acid (170 mg). This compound was dissolved in methanol (2 ml), a 0.586M solution (0.62 ml) of sodium hydroxide in methanol was added, and the methanol was evaporated under reduced pressure. The obtained residue was dissolved in water (1 ml), and lyophilized to give the title compound (170 mg).

IR ν (KBr) cm$^{-1}$; 1653, 1595, 1506. $^1$H-NMR (DMSO-d$_6$) δ (ppm); 0.89 (6H, br-t), 1.10-1.75 (6H, m), 1.90-2.20 (4H, m), 2.25 (3H, s), 2.79 (2H, br-t), 3.00-3.30 (2H, br), 4.07 (2H, br-t), 4.20-5.15 (3H, m), 6.19 (1H, d, J=16.7 Hz), 6.30-6.80 (5H, m), 6.96 (1H, d, J=8.4 Hz).

Reference Example 2

2-(2,4-hexadienoyl)-7-[2-(5-methyl-2-(trans-1-penten-1-yl)oxazol-4-yl)ethoxy]-1,2,3,4-tetrahydroisoquinoline-(3S)-carboxylic Acid (1) Methyl 2-tert-butoxycarbonyl-7-hydroxy-1,2,3,4-tetrahydroisoquinoline-(3S)-carboxylate (0.5 g) and 2-[5-methyl-2-(trans-1-penten-1-yl)oxazol-4-yl]ethyl methanesulfonate (0.67 g) were dissolved in toluene (5 ml), potassium carbonate (0.68 g) and tetraethylammonium fluoride hydrate (0.12 g) were added, and the mixture was stirred at 80° C. for 18 hr. Ethyl acetate (20 ml) was added to the reaction mixture, and the mixture was washed with water (20 ml) and saturated brine (20 ml), and dried over $Na_2SO_4$. The solvent was evaporated under reduced pressure. The obtained residue was purified by silica gel column chromatography to give methyl 2-tert-butoxycarbonyl-7-[2-(5-methyl-2-(trans-1-penten-1-yl)oxazol-4-yl)ethoxy]-1,2,3,4-tetrahydroisoquinoline-(3S)-carboxylate (0.57 g).

IR ν (neat) cm$^{-1}$; 1746, 1698, 1615, 1533, 1505. $^1$H-NMR (CDCl$_3$) δ (ppm); 0.89 (3H, t, J=7.0 Hz), 1.20-1.80 (11H, m), 2.00-2.40 (2H, m), 2.28 (3H, s), 2.89 (2H, t, J=6.8 Hz), 2.90-3.20 (2H, m), 3.61 (3H, s), 4.15 (2H, t, J=6.8 Hz), 4.40-4.90 (2H, m), 5.00-5.20 (1H, m), 6.18 (1H, d, J=16.1 Hz), 6.73 (1H, dt, J=16.1, 6.8 Hz), 6.50-6.80 (2H, m), 7.01 (1H, d, J=8.4 Hz).

(2) The compound (0.55 g) obtained in the above-mentioned (1) was dissolved in formic acid (3 ml), a 8.78M solution (0.39 ml) of hydrogen chloride in 2-propanol was added under ice-cooling, and the mixture was stirred at room temperature for 30 min. Ethyl acetate (20 ml) was added to the reaction mixture, the mixture was neutralized with saturated aqueous sodium hydrogencarbonate, and the two layers were separated. The obtained ethyl acetate layer was washed with saturated brine (10 ml), and dried over $Na_2SO_4$. The ethyl acetate was evaporated under reduced pressure. The obtained residue was purified by silica gel column chromatography to give methyl 7-[2-(5-methyl-2-(trans-1-penten-1-yl)oxazol-4-yl)ethoxy]-1,2,3,4-tetrahydroisoquinoline-(3S)-carboxylate (0.39 g).

IR ν (neat) cm$^{-1}$; 1743, 1505. $^1$H-NMR (CDCl$_3$) δ (ppm); 0.94 (3H, t, J=7.0 Hz), 1.20-1.70 (2H, m), 2.00-2.40 (3H, m), 2.27 (3H, s), 2.50-3.20 (2H, m), 2.86 (2H, t, J=6.7 Hz), 3.60-3.90 (1H, m), 3.76 (3H, s), 4.05 (2H, s), 4.14 (2H, t, J=6.7 Hz), 6.17 (1H, d, J=16.0 Hz), 6.40-6.80 (1H, m), 6.54 (1H, d, J=2.6 Hz), 6.69 (1H, dd, J=8.3, 2.6 Hz), 6.99 (1H, d, J=8.3 Hz).

(3) The compound (0.36 g) obtained in the above-mentioned (2) was dissolved in methylene chloride (5 ml), sorbyl chloride (0.13 g) and triethylamine (0.17 ml) were added, and the mixture was stirred at room temperature for 30 min. Ethyl acetate (30 ml) was added, the mixture was washed with 10% aqueous citric acid (15 ml) and saturated brine (15 ml), and dried over $Na_2SO_4$. The solvent was evaporated under reduced pressure. The obtained residue was purified by silica gel column chromatography to give methyl 2-(2,4-hexadienoyl)-7-[2-(5-methyl-2-(trans-1-penten-1-yl)oxazol-4-yl)ethoxy]-1,2,3,4-tetrahydroisoquinoline-(3S)-carboxylate (0.4 g).

IR ν (neat) cm$^{-1}$; 1740, 1655, 1628, 1605, 1506. $^1$H-NMR (CDCl$_3$) δ (ppm); 0.95 (3H, t, J=6.8 Hz), 1.20-1.70 (2H, m), 1.85 (3H, d, J=5,0 Hz), 2.00-2.40 (2H, m), 2.04 (3H, s), 2.87 (2H, t, J=6.7 Hz), 3.00-3.25 (2H, m), 3.59 (3H, s), 4.15 (2H, t, J=6.7 Hz), 4.50-5.65 (3H, m), 6.00-6.90 (7H, m), 7.03 (1H, d, J=8.2 Hz), 7.15-7.55 (1H, m).

(4) The compound (0.37 g) obtained in the above-mentioned (3) was dissolved in a mixed solvent (9.4 ml) of tetrahydrofuran-methanol (3:1), 1M aqueous lithium hydroxide solution (2.35 ml) was added, and the mixture was stirred at 50° C. for 30 min. The mixture was acidified with 10% aqueous citric acid, and the solution was concentrated under reduced pressure. The precipitated gum-like substance was extracted with ethyl acetate (50 ml), the ethyl acetate layer was washed with saturated brine (30 ml), and dried over $Na_2SO_4$. The ethyl acetate was evaporated under reduced pressure. The obtained residue was purified by silica gel column chromatography to give the title compound (0.28 g).

IR ν (nujol) cm$^{-1}$; 1728, 1651, 1616, 1531, 1504. $^1$H-NMR (CDCl$_3$) δ (ppm); 0.92 (3H, t, J=6.8 Hz), 1.20-1.75 (2H, m), 1.84 (3H, d, J=4.8 Hz), 2.14 (2H, m), 2.22 (3H, s), 2.65 (2H, br-t), 2.80-3.50 (2H, m), 3.95 (2H, br-t), 4.60-5.10 (3H, m), 5.40-5.65 (1H, m), 6.00-6.80 (5H, m), 7.02 (1H, d, J=8.4 Hz), 7.15-7.55 (1H, m), 9.80-10.50 (1H, br).

Reference Example 3 methyl 2-(2-heptenoyl)-7-[2-(5-methyl-2-(trans-1-penten-1-yl)oxazol-4-yl)ethoxy]-1,2,3,4-tetrahydroisoquinoline-(3S)-carboxylate The compound (210 mg) obtained in Reference Example 2 (2) was dissolved in methylene chloride (2.1 ml), 2-heptenoic acid (105 mg) and 1-ethyl-3-(3'-dimethylaminopropyl)carbodiimide hydrochloride (160 mg) were added, and the mixture was stirred at room temperature for 1 hr. Ethyl acetate (30 ml) was added, the mixture was washed with 10% aqueous citric acid (15 ml) and saturated brine (15 ml), and dried over $Na_2SO_4$. The solvent was evaporated under reduced pressure. The obtained residue was purified by silica gel column chromatography to give methyl 2-(2-heptenoyl)-7-[2-(5-methyl-2-(trans-1-penten-1-yl)oxazol-4-yl)ethoxy]-1,2,3,4-tetrahydroisoquinoline-(3S)-carboxylate (200 mg).

The $^1$H-NMR data was matched with those of the compound of Reference Example 1.

The compounds of Reference Examples 4-15 were synthesized according to Reference Examples 1-3.

Reference Example 4

2-(2-hexynoyl)-7-[2-(5-methyl-2-(trans-1-penten-1-yl)oxazol-4-yl)ethoxy]-1,2,3,4-tetrahydroisoquinoline-(3S)-carboxylic Acid IR ν (nujol) cm$^{-1}$; 2237, 1717, 1684, 1616, 1576, 1506. $^1$H-NMR (CDCl$_3$) δ (ppm); 0.85-1.20 (6H, m), 1.25-1.90 (4H, m), 2.00-2.50 (4H, m), 2.24 (3H, s), 2.60-3.50 (4H, m), 3.80-4.10 (2H, m), 4.35-5.20 (2H, m), 5.30-5.65 (1H, m), 6.18 (1H, d, J=16.0 Hz), 6.45-6.85 (3H, m), 7.02 (1H, d, J=7.9 Hz), 8.80-9.40 (1H, br).

Reference Example 5

2-(2,4-hexadienoyl)-7-[2-(5-methyl-2-styryloxazol-4-yl)ethoxy]-1,2,3,4-tetrahydroisoquinoline-(3S)-carboxylic Acid IR ν (nujol) cm$^{-1}$; 1729, 1652, 1615, 1575. $^1$H-NMR (CDCl$_3$) δ (ppm); 1.83 (3H, br-d), 2.28 (3H, s), 2.82 (2H, br-t), 2.90-3.50 (2H, m), 4.03 (2H, br-t), 4.60-5.10 (3H, m), 5.40-5.65 (1H, m), 6.00-6.80 (5H, m), 6.84 (1H, d, J=16.5 Hz), 7.04 (1H, d, J=8.4 Hz), 7.15-7.65 (7H, m), 9.40-10.20 (1H, br).

Reference Example 6

2-(2-heptenoyl)-7-[2-(5-methyl-2-styryloxazol-4-yl)ethoxy]-1,2,3,4-tetrahydroisoquinoline-(3S)-carboxylic Acid IR ν (nujol) cm$^{-1}$; 1740, 1653, 1612, 1553, 1506. $^1$H-NMR (CDCl$_3$) δ (ppm); 0.70-1.00 (3H, br), 1.10-1.75 (4H, m), 1.90-2.40 (2H, br), 2.29 (3H, s), 2.60-3.40 (4H, m), 3.75-4.20 (2H, m), 4.55-5.10 (2H, m), 5.40-5.70 (1H, m), 6.33 (1H, d, J=15.7 Hz), 6.55-7.25 (5H, m), 7.30-7.70 (6H, m), 8.00-8.80 (1H, br).

Reference Example 7

2-(2-hexynoyl)-7-[2-(5-methyl-2-styryloxazol-4-yl)ethoxy]-1,2,3,4-tetrahydroisoquinoline-(3S)-carboxylic Acid IR ν (nujol) cm$^{-1}$; 2235, 1734, 1630, 1580, 1528, 1504. $^1$H-NMR(CDCl$_3$) δ (ppm); 0.96, 1.04 (3H, t, t, J=6.7 Hz), 1.35-1.80 (2H, m), 2.20-2.50 (2H, m), 2.32 (3H, s), 2.70-3.50 (4H, m), 3.80-4.15 (2H, m), 4.55-5.20 (2H, m), 5.30-5.60 (2H, m), 6.45-6.70 (2H, m), 7.85 (1H, d, J=16.5 Hz), 7.25-7.65 (6H, m), 7.90-8.60 (1H, br).

Reference Example 8

7-[2-(5-methyl-2-styryloxazol-4-yl)ethoxy]-2-pentafluoropropionyl-1,2,3,4-tetrahydroisoquinoline-(3S)-carboxylic Acid IR ν (nujol) cm$^{-1}$; 1732, 1680, 1647, 1614, 1578, 1531, 1506. $^1$H-NMR (CDCl$_3$+DMSO-d$_6$) δ (ppm); 2.34 (3H, s), 2.91 (2H, t, J=6.6 Hz), 3.10-3.30 (2H, m), 4.18 (2H, t, J=6.6 Hz), 4.40-5.30 (3H, m), 6.50-6.90 (2H, m), 6.84 (1H, d, J=16.5 Hz), 6.90-7.25 (2H, m), 7.30-7.60 (5H, m).

Reference Example 9

2-(2-heptenoyl)-7-[2-(5-methyl-2-styrylthiazol-4-yl)ethoxy]-1,2,3,4-tetrahydroisoquinoline-(3S)-carboxylic Acid IR ν (nujol) cm$^{-1}$; 1732, 1657, 1614, 1585, 1558, 1506. $^1$H-NMR (CDCl$_3$) δ (ppm); 0.75-1.05 (3H, br), 1.10-1.75 (4H, br), 2.00-2.50 (4H, m), 2.38 (3H, s), 2.70-3.40 (4H, m), 3.90-4.30 (2H, m), 4.50-5.10 (2H, m), 5.35-5.70 (1H, m), 6.10-7.70 (13H, m).

Reference Example 10

2-(2,4-hexadienoyl)-7-[2-(5-methyl-2-(1,3-pentadien-1-yl)oxazol-4-yl)ethoxy]-1,2,3,4-tetrahydroisoquinoline-(3S)-carboxylic Acid IR ν (nujol) cm$^{-1}$; 1730, 1648, 1616, 1456, 1377, 990. $^1$H-NMR (DMSO-d$_6$) δ (ppm); 1.83 (6H, br-s), 2.27 (3H, s), 2.6-3.4 (4H, m), 4.12 (2H, br-t), 4.2-5.0 (2H, m), 5.18 (1H, br-t), 5.9-7.4 (11H, m).

Reference Example 11

2-(2,4-hexadienoyl)-7-[2-(5-methyl-2-pentyloxazol-4-yl)ethoxy]-1,2,3,4-tetrahydroisoquinoline-(3S)-carboxylic Acid IR ν (nujol) cm$^{-1}$; 1728, 1653, 1616, 1574, 1506. $^1$H-NMR (CDCl$_3$) δ (ppm); 0.87 (3H, t, J=5.9 Hz), 1.10-1.40 (4H, m), 1.45-1.80 (2H, m), 1.84 (3H, d, J=4.6 Hz), 2.20 (3H, s), 2.65 (2H, t, J=8.1 Hz), 2.73 (2H, br-t), 3.93 (2H, br-t), 4.40-5.10 (3H, m), 5.45-5.70 (1H, m), 6.10-6.80 (5H, m), 7.03 (1H, d, J=8.6 Hz), 7.10-7.50 (1H, m), 9.10-10.00 (1H, br).

Reference Example 12

7-[2-(2-cyclopentyl-5-methyloxazol-4-yl)ethoxy]-2-(2,4-hexadienoyl)-1,2,3,4-tetrahydroisoquinoline-(3S)-carboxylic Acid IR ν (nujol) cm$^{-1}$; 1733, 1652, 1615, 1568. $^1$H-NMR (CDCl$_3$) δ (ppm); 1.0-2.0 (11H, m), 2.20 (3H, s), 2.77 (2H, t, J=6.0 Hz), 2.8-3.4 (3H, m), 3.93 (2H, t, J=6.4 Hz), 4.6-5.0 (2H, m), 5.54 (1H, br-t), 6.0-6.8 (5H, m), 7.02 (1H, d, J=8.4 Hz), 7.1-7.6 (1H, m), 8.8-9.6 (1H, br).

Reference Example 13

7-[2-(2-cyclohexyl-5-methyloxazol-4-yl)ethoxy]-2-(2,4-hexadienoyl)-1,2,3,4-tetrahydroisoquinoline-(3S)-carboxylic Acid IR ν (nujol) cm$^{-1}$; 1733, 1652, 1616, 1456, 1377, 1260, 999. $^1$H-NMR (DMSO-d$_6$) δ (ppm); 1.0-2.0 (13H, m), 2.20 (3H, s), 2.77 (2H, t, J=6.4 Hz), 2.8-3.4 (3H, m), 4.09 (2H, t, J=6.4 Hz), 4.2-5.0 (2H, m), 5.17 (1H, br-t), 5.9-7.3 (7H, m).

Reference Example 14

2-(2-heptenoyl)-7-[2-(1-phenylethylideneaminoxy)ethoxy]-1,2,3,4-tetrahydroisoquinoline-(3S)-carboxylic Acid IR ν (nujol) cm$^{-1}$; 1732, 1716, 1651, 1574, 1506. $^1$H-NMR (CDCl$_3$) δ (ppm); 0.75-1.05 (3H, m), 1.10-1.70 (4H, m), 2.00-2.40 (2H, m), 2.21 (3H, s), 2.80-3.30 (2H, m), 4.10-4.30 (2H, m), 4.40-5.10 (4H, m), 5.30-5.60 (1H, m), 6.15-7.15 (6H, m), 7.25-7.50 (3H, m), 7.60-7.80 (2H, m).

Reference Example 15

2-(2-heptenoyl)-7-[2-(4-methyl-2-phenylsulfanylthiazol-5-yl)ethoxy]-1,2,3,4-tetrahydroisoquinoline-(3S)-carboxylic Acid IR ν (nujol) cm$^{-1}$; 1726, 1612, 1582, 1502. $^1$H-NMR (DMSO-d$_6$) δ (ppm); 0.70-1.10 (3H, m), 1.20-1.70 (4H, m), 2.00-2.30 (2H, m), 2.29 (3H, s), 2.90-3.60 (5H, m), 4.04 (2H, t, J=5.9 Hz), 4.35-4.95 (2H, m), 5.00-5.30 (1H, m), 6.35-6.90 (4H, m), 7.09 (1H, d, J=7.9 Hz), 7.35-7.70 (5H, m).

Reference Example 16

7-[2-(2-benzoylaminothiazol-5-yl)ethoxy]-2-(2-heptenoyl)-1,2,3,4-tetrahydroisoquinoline-(3S)-carboxylic Acid (1) 2-(2-Aminothiazol-5-yl)ethyl methanesulfonate (2.43 g) and methyl 2-tert-butoxycarbonyl-7-hydroxy-1,2,3,4-tetrahydroisoquinoline-(3S)-carboxylate (2.17 g) were dissolved in N,N-dimethylformamide (50 ml), cesium carbonate (5.20 g) was added, and the mixture was stirred at 55° C. for 15 hr. Water (200 ml) was added to the reaction mixture, and the mixture was extracted with ethyl acetate (100 ml, three times). The ethyl acetate layer was washed with water (100 ml, twice) and saturated brine (100 ml), and dried over Na$_2$SO$_4$. The ethyl acetate was evaporated under reduced pressure. The obtained residue was purified by column chromatography to give methyl 7-(2-aminothiazol-5-yl)ethoxy-2-tert-butoxycarbonyl-1,2,3,4-tetrahydroisoquinoline-(3S)-carboxylate (2.20 g).

$^1$H-NMR (CDCl$_3$) δ (ppm); 1.46, 1.51 (9H, s, s), 2.80-3.30 (4H, m), 3.61 (3H, s), 4.07 (2H, t, J=6.3 Hz), 4.30-4.90 (4H, m), 4.95-5.25 (1H, m), 6.55-6.90 (3H, m), 7.03 (1H, d, J=8.4 Hz).

(2) The compound (500 mg) obtained in the above-mentioned (1) was dissolved in N,N-dimethylformamide (5.0 ml), triethylamine (0.25 ml) and benzoyl chloride (0.16 ml) were added, and the mixture was stirred at 55° C. for 15 hr. Water (20 ml) was added to the reaction mixture, and the mixture was extracted with ethyl acetate (10 ml, three times). The ethyl acetate layer was washed with water (20 ml, twice) and saturated brine (20 ml), and the dried over Na$_2$SO$_4$. The ethyl acetate was evaporated under reduced pressure. The obtained residue was purified by column chromatography to give methyl 7-(2-benzoylaminothiazol-5-yl)ethoxy-2-tert-butoxycarbonyl-1,2,3,4-tetrahydroisoquinoline-(3S)-carboxylate (535 mg).

IR ν (nujol) cm$^{-1}$; 1746, 1684, 1605, 1582, 1555, 1535, 1506. $^1$H-NMR (CDCl$_3$) δ (ppm); 1.46, 1.51 (9H, s, s), 2.90-3.30 (5H, m), 3.61 (3H, s), 4.11 (2H, t, J=6.1 Hz), 4.20-4.90 (2H, m), 4.95-5.25 (1H, m), 6.55-6.90 (3H, m), 7.04 (1H, d, J=7.9 Hz), 7.30-7.70 (3H, m), 7.90-8.20 (2H, m).

(3) The compound (535 mg) obtained in the above-mentioned (2) was dissolved in formic acid (2.0 ml), a 8.78M solution (0.30 ml) of hydrogen chloride in 2-propanol was added under ice-cooling, and the mixture was stirred at the same temperature for 15 min. The reaction mixture was neutralized with saturated aqueous sodium hydrogencarbonate, and extracted with chloroform (30 ml), and the chloroform layer was dried over $Na_2SO_4$. The chloroform was evaporated under reduced pressure to give methyl 7-(2-benzoylaminothiazol-5-yl)ethoxy-1,2,3,4-tetrahydroisoquinoline-(3S)-carboxylate (401 mg).

IR ν (nujol) cm$^{-1}$; 3161, 1744, 1659, 1603, 1582, 1558, 1535, 1501. $^1$H-NMR (CDCl$_3$) δ (ppm): 2.90-3.10 (2H, m), 3.19 (2H, t, J=6.1 Hz), 3.60-3.80 (1H, m), 3.77 (3H, s), 4.00-4.30 (4H, m), 6.58 (1H, d, J=2.2 Hz), 6.74 (1H, dd, J=2.2, 8.4 Hz), 6.95-7.10 (2H, m), 7.30-7.60 (3H, m), 7.85-8.10 (2H, m).

(4) The compound (400 mg) obtained in the above-mentioned (3) was dissolved in methylene chloride (5.0 ml), 2-heptenoic acid (0.19 ml) and 1-ethyl-3-(3'-dimethylaminopropyl)carbodiimide hydrochloride (265 mg) were added under ice-cooling, and the mixture was stirred at room temperature for 1 hr. The mixture was washed with 10% aqueous citric acid (10 ml) and saturated brine (30 ml), and the dried over $Na_2SO_4$. The methylene chloride was evaporated under reduced pressure. The obtained residue was purified by column chromatography to give methyl 7-(2-benzoylaminothiazol-5-yl)ethoxy-2-(2-heptenoyl)-1,2,3,4-tetrahydroisoquinoline-(3S)-carboxylate (495 mg). IR ν (neat) cm$^{-1}$; 3165, 1740, 1661, 1616, 1558, 1533, 1506.

$^1$H-NMR (CDCl$_3$) δ (ppm): 0.80-1.10 (3H, m), 1.20-1.70 (4H, m), 2.00-2.50 (2H, m), 3.00-3.45 (4H, m), 3.60 (3H, s), 4.12 (2H, t, J=5.9 Hz), 4.50-5.00 (2H, m), 5.40-5.60 (1H, m), 6.35 (1H, d, J=15.1 Hz), 6.65-7.20 (4H, m), 7.35-7.70 (3H, m), 7.80-8.15 (2H, m).

(5) The compound (490 mg) obtained in the above-mentioned (4) was dissolved in a mixed solvent (20 ml) of tetrahydrofuran-methanol (3:1), 1M aqueous lithium hydroxide solution (3.0 ml) was added, and the mixture was stirred at 50° C. for 30 min. The mixture was acidified with 10% aqueous citric acid, and the solvent was evaporated under reduced pressure. The precipitated crystals were collected by filtration to give the title compound (342 mg).

IR ν (nujol) cm$^{-1}$; 1734, 1655, 1603, 1560, 1541, 1506. $^1$H-NMR (CDCl$_3$) δ (ppm): 0.80-1.10 (3H, m), 1.20-1.70 (4H, m), 2.00-2.50 (2H, m), 2.80-3.40 (4H, m), 3.80-4.20 (2H, m), 4.50-5.05 (2H, m), 5.50-5.80 (1H, m), 6.05-7.20 (6H, m), 7.30-7.70 (3H, m), 7.80-8.15 (2H, m), 9.60-11.20 (1H, br).

The compound of Reference Example 17 was synthesized according to Reference Example 16.

Reference Example 17

7-[2-(2-butyrylaminothiazol-5-yl)ethoxy]-2-(2-heptenoyl)-1,2,3,4-tetrahydroisoquinoline-(3S)-carboxylic Acid IR ν (nujol) cm$^{-1}$; 3172, 1734, 1692, 1655, 1612, 1562, 1504. $^1$H-NMR (CDCl$_3$) (ppm): 0.94 (6H, t, J=7.0 Hz), 1.10-1.90 (6H, m), 2.10-2.60 (2H, m), 2.80-3.50 (4H, m), 3.80-4.30 (2H, m), 4.40-5.10 (2H, m), 5.55-5.80 (1H, m), 6.10-7.30 (6H, m), 9.60-11.20 (2H, br).

Reference Example 18 methyl 7-{2-[5-methyl-2-(4-methyl-trans-1-penten-1-yl)oxazol-4-yl]ethoxy}-1,2,3,4-tetrahydroisoquinoline-(3S)-carboxylate (1) Methyl 2-tert-butoxycarbonyl-7-hydroxy-1,2,3,4-tetrahydroisoquinoline-(3S)-carboxylate (1.0 g) and 2-[5-methyl-2-(4-methyl-trans-1-penten-1-yl)oxazol-4-yl] ethyl methanesulfonate (1.4 g) were dissolved in toluene (30 ml), potassium carbonate (1.35 g) and tetraethylammonium fluoride hydrate (0.2 g) were added, and the mixture was stirred at 80° C. for 13 hr. Ethyl acetate (50 ml) was added to the reaction mixture, and the mixture was washed successively with water (50 ml) and saturated brine (30 ml), and the dried over $Na_2SO_4$. The solvent was evaporated under reduced pressure. The obtained residue was purified by silica gel column chromatography to give methyl 2-tert-butoxycarbonyl-7-[2-(5-methyl-2-(4-methyl-trans-1-penten-1-yl)oxazol-4-yl)ethoxy]-1,2,3,4-tetrahydroisoquinoline-(3S)-carboxylate (1.6 g).

IR ν (neat) cm$^{-1}$; 2957, 2928, 2872, 1746, 1701, 1614, 1533, 1506. $^1$H-NMR (CDCl$_3$) δ (ppm): 0.94(6H, d, J=6.3 Hz), 1.46, 1.50(9H, s, s), 1.50-2.00 (1H, m), 2.11(2H, t, J=6.8 Hz), 2.28 (3H, s), 2.87 (2H, t, J=6.6 Hz), 3.00-3.25 (2H, m), 3.61 (3H, s), 4.15 (2H, t, J=6.6 Hz), 4.45-5.25 (3H, m), 6.15 (1H, d, J=15.8 Hz), 6.45-6.80 (3H, m), 7.01 (1H, d, J=8.8 Hz).

(2) The compound (1.6 g) obtained in the above-mentioned (1) was dissolved in formic acid (8 ml), a 8.78M solution (1.1 ml) of hydrogen chloride in 2-propanol was added under ice-cooling, and the mixture was stirred at room temperature for 15 min. Ethyl acetate and water (50 ml, respectively) were added to the reaction mixture, the mixture was neutralized with sodium hydrogencarbonate, and the two layers were separated. The obtained ethyl acetate layer was washed with saturated brine (30 ml), and the dried over $Na_2SO_4$. The ethyl acetate was evaporated under reduced pressure. The obtained residue was purified by silica gel column chromatography to give the title compound (1.17 g).

IR ν (neat) cm$^{-1}$; 3344, 2955, 2926, 2870, 1738, 1661, 1641, 1612, 1533, 1504. $^1$H-NMR(CDCl$_3$) δ (ppm): 0.94 (6H, d, J=6.3 Hz), 1.50-1.95 (1H, m), 2.11 (2H, t, J=6.6 Hz), 2.12 (1H, br-s), 2.28 (3H, s), 2.87 (2H, t, J=6.8 Hz), 2.90-3.10 (2H, m), 3.55-3.90 (1H, m), 3.77 (3H, s), 4.06 (2H, s), 4.14 (2H, t, J=6.8 Hz), 6.16 (1H, d, J=15.8 Hz), 6.40-6.80 (3H, m), 7.00 (1H, d, J=8.4 Hz).

Reference Example 19

2-(2,4-hexadienoyl)-7-{2-[5-methyl-2-(4-methyl-trans-1-penten-1-yl)oxazol-4-yl]ethoxy}-1,2,3,4-tetrahydroisoquinoline-(3S)-carboxylic Acid (1) The compound (1.15 g) obtained in Reference Example 18 was dissolved in methylene chloride (20 ml), sorbyl chloride (0.45 g) and triethylamine (0.6 ml) were added, and the mixture was stirred at room temperature for 15 min. Methylene chloride (30 ml) was added, and the mixture was washed with water and saturated brine (30 ml, respectively), and the dried over $Na_2SO_4$. The methylene chloride was evaporated under reduced pressure. The obtained residue was purified by silica gel column chromatography to give methyl 2-(2,4-hexadienoyl)-7-[2-(5-methyl-2-(4-methyl-trans-1-penten-1-yl)oxazol-4-yl)ethoxy]-1,2,3,4-tetrahydroisoquinoline-(3S)-carboxylate (1.36 g).

IR ν (neat) cm$^{-1}$; 1740, 1655, 1628, 1533, 1508. $^1$H-NMR (CDCl$_3$) δ (ppm): 0.94 (6H, d, J=6.4 Hz), 1.50-1.95 (4H, m), 2.11 (2H, t, J=7.0 Hz), 2.28 (3H, s), 2.87 (2H, t, J=6.6 Hz), 3.00-3.30 (2H, m), 3.60 (3H, s), 4.15 (2H, t, J=6.6 Hz), 4.50-5.15 (2H, m), 5.40-5.70 (1H, m), 6.00-6.90 (7H, m), 7.04 (1H, d, J=8.2 Hz), 7.15-7.55 (1H, m).

(2) The compound (1.36 g) obtained in the above-mentioned (1) was dissolved in a mixed solvent (16 ml) of tetrahydrofuran-methanol (3:1), 1M aqueous lithium hydroxide solution (8.3 ml) was added, and the mixture was stirred at room temperature for 30 min. The mixture was acidified with 10% aqueous citric acid, and the solution was concentrated under reduced pressure. The precipitated gum-like substance was extracted with ethyl acetate (50 ml), the ethyl acetate layer was washed with saturated brine (30 ml), and dried over $Na_2SO_4$. The ethyl acetate was evaporated under reduced pressure to give the title compound (1.26 g). IR ν (neat) $cm^{-1}$; 2959, 2930, 2872, 1738, 1651, 1620, 1583, 1533, 1506.

$^1$H-NMR (CDCl$_3$) δ (ppm); 0.92 (6H, d, J=6.4 Hz), 1.45-2.00 (1H, m), 1.84 (3H, d, J=4.9 Hz), 2.09 (2H, t, J=7.0 Hz), 2.23 (3H, s), 2.78 (2H, t, J=6.4 Hz), 2.95-3.40 (2H, m), 4.00 (2H, t, J=6.4 Hz), 4.30-5.65 (3H, m), 5.95-7.55 (9H, m).

Reference Example 20

2-(2,4-hexadienoyl)-7-{2-[5-methyl-2-(4-methyl-trans-1-penten-1-yl)oxazol-4-yl]ethoxy}-1,2,3,4-tetrahydroisoquinoline-(3S)-carboxylic acid tert-butylamine Salt The compound (1.25 g) obtained in Reference Example 19 was dissolved in methanol (7.0 ml), tert-butylamine (0.55 ml) was added dropwise, diisopropyl ether (70 ml) was added, and the mixture was stirred at room temperature for 30 min. The precipitated crystals were collected by filtration to give the title compound (1.15 g).

IR ν (neat) $cm^{-1}$; 2741, 2633, 2544, 1653, 1628, 1558, 1506. $^1$H-NMR (CDCl$_3$) δ (ppm); 0.93 (6H, d, J=6.6 Hz), 0.99 (9H, s), 1.60-2.00 (4H, m), 2.10 (2H, t, J=6.8 Hz), 2.28 (3H, s), 2.86 (2H, t, J=6.8 Hz), 2.90-3.40 (2H, m), 4.11 (2H, t, J=6.8 Hz), 4.30-5.25 (3H, m), 6.00-7.50 (12H, m).

Reference Example 21 methyl 7-{2-[2-(trans-2-cyclopentylvinyl)-5-methyloxazol-4-yl]ethoxy}-1,2,3,4-tetrahydroisoquinoline-(3S)-carboxylate (1) Methyl 2-tert-butoxycarbonyl-7-hydroxy-1,2,3,4-tetrahydroisoquinoline-(3S)-carboxylate (2.93 g) and 2-[2-(trans-2-cyclopentylvinyl)-5-methyloxazol-4-yl]ethyl methanesulfonate (4.29 g) were dissolved in toluene (90 ml), potassium carbonate (3.95 g) and tetraethylammonium fluoride hydrate (0.75 g) were added, and the mixture was stirred at 90° C. for 16 hr. Ethyl acetate (30 ml) was added to the reaction mixture, and the mixture was washed successively with water (50 ml) and saturated brine (50 ml), and the dried over $Na_2SO_4$. The solvent was evaporated under reduced pressure. The obtained residue was purified by silica gel column chromatography to give methyl 2-tert-butoxycarbonyl-7-[2-(trans-2-cyclopentylvinyl)-5-methyloxazol-4-yl)oxazol-4-yl)ethoxy]-1,2,3,4-tetrahydroisoquinoline-(3S)-carboxylate (3.9 g).

IR ν (neat) $cm^{-1}$; 2955, 2970, 1742, 1699, 1614, 1533, 506. $^1$H-NMR (CDCl$_3$) δ (ppm); 1.20-2.00 (17H, m), 2.27 (3H, s), 2.34-2.74 (1H, m), 2.86 (2H, t, J=6.6 Hz), 2.99-3.20 (2H, m), 3.61 (3H, s), 4.12 (2H, t, J=6.6 Hz), 4.24-5.20 (3H, m), 6.15 (1H, d, J=16.1 Hz), 6.61 (1H, dd, J=16.1, 7.5 Hz), 6.53-6.80 (2H, m), 7.01 (1H, d, J=8.3 Hz).

(2) The compound (3.89 g) obtained in the above-mentioned (1) was dissolved in formic acid (9.7 ml), a 10M solution (2.28 ml) of hydrogen chloride in 2-propanol was added under ice-cooling, and the mixture was stirred at room temperature for 35 min. Under ice-cooling, the reaction mixture was poured into a mixed solvent (200 ml) of diisopropyl ether-n-hexane (1:1), and the resulting oil was separated by decantation. The obtained oil was dissolved in ethyl acetate (100 ml), water (100 ml) was added. The mixture was neutralized with sodium hydrogencarbonate, and the two layers were separated. The ethyl acetate layer was washed successively with water and saturated brine (50 ml, respectively), and dried over $Na_2SO_4$. The ethyl acetate was evaporated under reduced pressure to give the title compound (3.07 g).

IR ν (neat) $cm^{-1}$; 3344, 2951, 2870, 2777, 2740, 1659, 1643, 1612, 1504. $^1$H-NMR (CDCl$_3$) δ (ppm); 1.20-1.97 (8H, m), 1.99 (1H, s), 2.27 (3H, s), 2.30-2.77 (1H, m), 2.86 (2H, t, J=6.7 Hz), 2.80-3.10 (2H, m), 3.60-3.83 (1H, m), 3.76 (3H, s), 3.95-4.34 (4H, m), 6.15 (1H, d, J=16.0 Hz), 6.41-6.80 (3H, m), 6.99 (1H, d, J=8.4 Hz).

Reference Example 22

7-{2-[2-(trans-2-cyclopentylvinyl)-5-methyloxazol-4-yl]ethoxy}-2-(2,4-hexadienoyl)-1,2,3,4-tetrahydroisoquinoline-(3S)-carboxylic acid tert-butylamine Salt (1) The compound (3.05 g) obtained in Reference Example 21 was dissolved in methylene chloride (30 ml), sorbyl chloride (1.12 g) and triethyl amine (1.35 ml) were added under ice-cooling, and the mixture was stirred at the same temperature for 20 min. The mixture was washed with 10% aqueous citric acid and saturated brine (20 ml, respectively), and the dried over $Na_2SO_4$. The methylene chloride was evaporated under reduced pressure. The obtained residue was purified by silica gel column chromatography to give methyl 7-{2-[2-(trans-2-cyclopentylvinyl)-5-methyloxazol-4-yl]ethoxy}-2-(2,4-hexadienoyl)-1,2,3,4-tetrahydroisoquinoline-(3S)-carboxylate (2.49 g).

IR ν (neat) $cm^{-1}$; 3464, 2953, 2870, 1740, 1657, 1628, 1605, 1506. $^1$H-NMR (CDCl$_3$) δ (ppm); 1.20-1.97 (8H, m), 1.85 (3H, d, J=4.8 Hz), 2.27 (3H, s), 2.40-2.75 (1H, m), 2.86 (2H, t, J=6.5 Hz), 3.00-3.22 (2H, m), 3.59 (3H, s), 4.14 (2H, t, J=6.5 Hz), 4.36-5.00 (2H, m), 5.40-5.60 (1H, m), 6.07-6.80 (5H, m), 6.15 (1H, d, J=16.1 Hz), 6.61 (1H, dd, J=16.1, 7.2 Hz), 7.03 (1H, d, J=8.4 Hz), 7.13-7.50 (1H, m).

(2) The compound (2.48 g) obtained in the above-mentioned (1) was dissolved in a mixed solvent (60 ml) of tetrahydrofuran-methanol (3:1), 1M aqueous lithium hydroxide solution (14.7 ml) was added, and the mixture was stirred at room temperature for 50 min. The mixture was acidified with 6M hydrochloric acid, and the solution was concentrated under reduced pressure. The precipitated gum-like substance was extracted with ethyl acetate (30 ml), and the ethyl acetate layer was washed with saturated brine (30 ml), and the dried over $Na_2SO_4$. The ethyl acetate was evaporated under reduced pressure. The obtained residue was dissolved in methanol (2.4 ml), tert-butylamine (1.0 ml) was added dropwise, diisopropyl ether (30 ml) was added, and the mixture was stirred under ice-cooling for 1 hr 20 min. The precipitated crystals were collected by filtration to give the title compound (2.41 g).

IR ν (nujol) $cm^{-1}$; 2731, 2631, 2544, 1653, 1626, 1553, 1506. $^1$H-NMR (CDCl$_3$) δ (ppm); 0.99 (9H, s), 1.20-2.05 (11H, m), 2.27 (3H, s), 2.38-2.73 (1H, m), 2.85 (2H, t, J=6.5 Hz), 2.90-3.40 (2H, m), 4.10 (2H, t, J=6.5 Hz), 4.26-5.20 (3H, m), 5.86-7.38 (12H, m).

Reference Example 23 methyl 2-(2-heptenoyl)-7-{2-[5-methyl-2-(4-methyl-trans-1-penten-1-yl)oxazol-4-yl]ethoxy}-1,2,3,4-tetrahydroisoquinoline-(3S)-carboxylate IR ν (nujol) cm$^{-1}$; 2955, 2928, 2872, 1740, 1661, 1622, 1533, 1506. $^1$H-NMR (CDCl$_3$) δ (ppm); 0.75-2.15 (3H, m), 0.94 (6H, d, J=6.4 Hz), 1.20-2.00 (5H, m), 2.20-2.45 (2H, m), 2.11 (2H, t, J=6.6 Hz), 2.28 (3H, s), 2.87 (2H, t, J=6.8 Hz), 3.00-3.325 (2H, m), 3.60 (3H, s), 4.15 (2H, t, J=6.8 Hz), 4.40-5.60 (3H, m), 6.16 (1H, d, J=16.0 Hz), 6.35-7.20 (6H, m).

Reference Example 24

2-(2-heptenoyl)-7-{2-[5-methyl-2-(4-methyl-trans-1-penten-1-yl)oxazol-4-yl]ethoxy}-1,2,3,4-tetrahydroisoquinoline-(3S)-carboxylic acid tert-butylamine Salt IR ν (nujol) cm$^{-1}$; 1661, 1616, 1558, 1506.
$^1$H-NMR (CDCl$_3$) δ (ppm); 0.75-2.20 (3H, m), 0.93 (6H, d, J=6.4 Hz), 1.02 (9H, s), 1.20-1.60 (4H, m), 1.60-1.95 (1H, m), 1.95-2.30 (2H, m), 2.10 (2H, t, J=6.6 Hz), 2.28 (3H, s), 2.86 (2H, t, J=6.8 Hz), 3.00-3.40 (2H, m), 4.10 (2H, t, J=6.8 Hz), 4.40-5.20 (3H, m), 6.15 (1H, d, J=16.1 Hz), 6.10-7.20 (9H, m).

Reference Example 25 methyl 7-{2-[2-(trans-1-hexen-1-yl)-5-methyloxazol-4-yl]ethoxy}-1,2,3,4-tetrahydroisoquinoline-(3S)-carboxylate IR ν (neat) cm$^{-1}$; 3346, 2955, 2928, 2872, 1742, 1661, 1612, 1504. $^1$H-NMR (CDCl$_3$) δ (ppm); 0.72-1.06 (3H, m), 1.06-1.65 (4H, m), 1.96-2.40 (3H, m), 2.27 (3H, s), 2.80-3.02 (2H, m), 2.86 (2H, t, J=6.7 Hz), 3.57-3.74 (1H, m), 3.76 (3H, s), 3.91-4.10 (2H, m), 4.14 (2H, t, J=6.7 Hz), 6.16 (1H, d, J=16.0 Hz), 6.39-6.79 (3H, m), 6.99 (1H, d, J=7.5 Hz).

Reference Example 26 methyl 2-(2,4-hexadienoyl)-7-{2-[2-(trans-1-hexen-1-yl)-5-methyloxazol-4-yl]ethoxy}-1,2,3,4-tetrahydroisoquinoline-(3S)-carboxylate IR ν (neat) cm$^{-1}$; 3468, 3020, 2957, 2930, 2872, 1740, 1657, 1629, 1605, 1506. $^1$H-NMR (CDCl$_3$) δ (ppm); 0.75-1.07 (3H, m), 1.20-1.60 (4H, m), 1.85 (3H, d, J=5.0 Hz), 2.08-2.40 (2H, m), 2.27 (3H, s), 2.87 (2H, t, J=6.6 Hz), 3.00-3.25 (2H, m), 3.60 (3H, s), 4.15 (2H, t, J=6.6 Hz), 4.35-5.10 (2H, m), 5.52 (1H, br-t), 5.96-6.84 (7H, m), 7.01 (1H, d, J=8.4 Hz), 7.15-7.50 (1H, m).

Reference Example 27

2-(2,4-hexadienoyl)-7-{2-[2-(trans-1-hexen-1-yl)-5-methyloxazol-4-yl]ethoxy}-1,2,3,4-tetrahydroisoquinoline-(3S)-carboxylic acid tert-butylamine Salt IR ν (nujol) cm$^{-1}$; 3400, 2745, 2637, 2548, 2220, 1651, 1626, 1556, 1506. $^1$H-NMR (CDCl$_3$) δ (ppm); 0.75-1.16 (3H, m), 0.98 (9H, s), 1.20-1.60 (4H, m), 1.70-2.00 (3H, m), 2.07-2.40 (2H, m), 2.27 (3H, s), 2.86 (2H, t, J=6.5 Hz), 2.88-3.30 (2H, m), 4.11 (2H, t, J=6.5 Hz), 4.25-5.20 (3H, m), 5.90-7.40 (12H, m).

Reference Example 28 methyl 7-{2-[5-methyl-2-(5-methyl-trans-1-hexen-1-yl)oxazol-4-yl]ethoxy}-1,2,3,4-tetrahydroisoquinoline-(3S)-carboxylate IR ν (neat) cm$^{-1}$; 3346, 2953, 2926, 2870, 2849, 1742, 1641, 1612, 1533, 1504. $^1$H-NMR (CDCl$_3$) δ (ppm); 0.90 (6H, d, J=6.1 Hz), 1.15-1.73 (3H, m), 1.86 (1H, br-s), 2.04-2.40 (2H, m), 2.27 (3H, s), 2.86 (2H, t, J=6.6 Hz), 2.90-3.06 (2H, m), 3.55-3.75 (1H, m), 3.77 (3H, s), 3.90-4.10 (2H, m), 4.22 (2H, t, J=6.6 Hz), 6.17 (1H, d, J=16.0 Hz), 6.39-6.81 (3H, m), 6.99 (1H, d, J=8.3 Hz).

Reference Example 29 methyl 2-(2,4-hexadienoyl)-7-{2-[5-methyl-2-(5-methyl-trans-1-hexen-1-yl)oxazol-4-yl]ethoxy}-1,2,3,4-tetrahydroisoquinoline-(3S)-carboxylate IR ν (neat) cm$^{-1}$; 3462, 2955, 2928, 2870, 1740, 1653, 1630, 1533, 1506. $^1$H-NMR (CDCl$_3$) δ (ppm); 0.90 (6H, d, J=6.2 Hz), 1.14-1.72 (3H, m), 1.86 (3H, d, J=5.0 Hz), 2.05-2.40 (2H, m), 2.27 (3H, s), 2.87 (2H, t, J=6.6 Hz), 3.00-3.25 (2H, m), 3.60 (3H, s), 4.15 (2H, t, J=6.6 Hz), 4.39-5.20 (2H, m), 5.42-5.65 (1H, m), 6.00-6.87 (7H, m), 7.04 (1H, d, J=8.1 Hz), 7.18-7.51 (1H, m).

Reference Example 30

2-(2,4-hexadienoyl)-7-{2-[5-methyl-2-(5-methyl-trans-1-hexen-1-yl)oxazol-4-yl]ethoxy}-1,2,3,4-tetrahydroisoquinoline-(3S)-carboxylic acid tert-butylamine Salt IR ν (nujol) cm$^{-1}$; 3400, 2735, 2635, 2550, 1657, 1634, 1558, 1506. $^1$H-NMR (CDCl$_3$) δ (ppm); 0.90 (6H, d, J=6.3 Hz), 0.97 (9H, s), 1.20-1.70 (3H, m), 1.70-1.98 (3H, m), 2.06-2.40 (2H, m), 2.27 (3H, s), 2.86 (2H, t, J=6.4 Hz), 2.90-3.25 (2H, m), 4.10 (2H, t, J=6.4 Hz), 4.25-5.20 (3H, m), 5.72-7.38 (12H, m).

Reference Example 31 methyl 7-{2-[5-methyl-2-(1-methyl-trans-1-penten-1-yl)oxazol-4-yl]ethoxy}-1,2,3,4-tetrahydroisoquinoline-(3S)-carboxylate IR ν (neat) cm$^{-1}$; 3344, 2957, 2930, 2872, 1742, 1647, 1612, 1504. $^1$H-NMR (CDCl$_3$) δ (ppm); 0.95 (3H, t, J=7.2 Hz), 1.20-1.72 (2H, m), 2.02 (3H, s), 2.03-2.30 (3H, m), 2.27 (3H, s), 2.88 (2H, t, J=6.8 Hz), 2.90-3.10 (2H, m), 3.60-3.80 (1H, m), 3.76 (3H, s), 4.05 (2H, s), 4.14 (2H, t, J=6.8 Hz), 6.30-6.80 (3H, m), 6.99 (1H, d, J=8.4 Hz).

Reference Example 32 methyl 2-(2,4-hexadienoyl)-7-{2-[5-methyl-2-(1-methyl-trans-1-penten-1-yl)oxazol-4-yl]ethoxy}-1,2,3,4-tetrahydroisoquinoline-(3S)-carboxylate IR ν (neat) cm$^{-1}$; 3462, 2957, 2930, 2872, 1740, 1655, 1628, 1612, 1533, 1506. $^1$H-NMR (CDCl$_3$) δ (ppm); 0.95 (3H, t, J=7.0 Hz), 1.20-1.75 (2H, m), 1.86 (3H, d, J=5.0 Hz), 2.00-2.30 (2H, m), 2.04 (3H, s), 2.28 (3H, s), 2.89 (2H, t, J=6.5 Hz), 3.02-3.25 (2H, m), 3.60 (3H, s), 4.15 (2H, t, J=6.5

Hz), 4.36-5.00 (2H, m), 5.50 (1H, br-t), 5.92-6.85 (6H, m), 7.03 (1H, d, J=8.1 Hz), 7.15-7.53 (1H, m).

Reference Example 33

2-(2,4-hexadienoyl)-7-{2-[5-methyl-2-(1-methyl-trans-1-penten-1-yl)oxazol-4-yl]ethoxy}-1,2,3,4-tetrahydroisoquinoline-(3S)-carboxylic acid tert-butylamine Salt IR ν (nujol) cm$^{-1}$; 2748, 2637, 2544, 2220, 1651, 1624, 1600, 1553. $^1$H-NMR (CDCl$_3$) δ (ppm): 0.80-1.08 (3H, m), 0.97 (9H, s), 1.11-1.70 (2H, m), 1.70-1.93 (3H, m), 1.93-2.35 (2H, m), 2.01 (3H, s), 2.27 (3H, s), 2.87 (2H, t, J=6.7 Hz), 2.90-3.40 (2H, m), 4.10 (2H, t, J=6.7 Hz), 4.24-5.20 (3H, m), 5.92-7.38 (11H, m).

Reference Example 34 methyl 7-{2-[5-methyl-2-(1-methyl-trans-1-buten-1-yl)oxazol-4-yl]ethoxy}-1,2,3,4-tetrahydroisoquinoline-(3S)-carboxylate IR ν (neat) cm$^{-1}$; 2956, 2932, 2875, 1739, 1646, 1611, 1582, 1533, 1505. $^1$H-NMR (CDCl$_3$) δ (ppm); 1.06 (3H, t, J=7.5 Hz), 2.01 (3H, s), 2.10-2.45 (3H, m), 2.27 (3H, s), 2.70-3.20 (4H, m), 3.55-3.90 (1H, m), 3.76 (3H, s), 4.05 (2H, s), 4.14 (2H, t, J=6.8 Hz), 6.25-6.85 (3H, m), 6.99 (1H, d, J=8.6 Hz).

Reference Example 35 methyl 2-(2,4-hexadienoyl)-7-{2-[5-methyl-2-(1-methyl-trans-1-buten-1-yl)oxazol-4-yl]ethoxy}-1,2,3,4-tetrahydroisoquinoline-(3S)-carboxylate IR ν (neat) cm$^{-1}$; 2961, 2933, 2875, 1739, 1652, 1627, 1606, 1534, 1506. $^1$H-NMR (CDCl$_3$) δ (ppm): 1.06 (3H, t, J=7.5 Hz), 1.85 (3H, d, J=5.0 Hz), 2.01 (3H, s), 2.05-2.45 (2H, m), 2.28 (3H, s), 2.89 (2H, t, J=6.4 Hz), 3.00-3.40 (2H, m), 4.15 (2H, t, J=6.4 Hz), 4.30-5.65 (3H, m), 7.03 (1H, d, J=8.4 Hz), 5.90-7.60 (7H, m).

Reference Example 36

2-(2,4-hexadienoyl)-7-{2-[5-methyl-2-(1-methyl-trans-1-buten-1-yl)oxazol-4-yl]ethoxy}-1,2,3,4-tetrahydroisoquinoline-(3S)-carboxylic acid tert-butylamine Salt IR ν (nujol) cm$^{-1}$; 2733, 2635, 2550, 1657, 1634, 1611, 1558, 1506. $^1$H-NMR (CDCl$_3$) δ (ppm): 0.99 (9H, s), 1.05 (3H, t, J=7.5 Hz), 1.65-1.95 (3H, m), 2.01 (3H, s), 2.05-2.45 (2H, m), 2.28 (3H, s), 2.87 (2H, t, J=6.7 Hz), 2.90-3.30 (2H, m), 4.11 (2H, t, J=6.7 Hz), 4.25-5.20 (3H, m), 5.90-8.30 (12H, m).

Reference Example 37

7-{2-[5-methyl-2-(trans-1-penten-1-yl)oxazol-4-yl]ethoxy}-2-(2,2,3,3,3-pentafluoropropionyl)-1,2,3,4-tetrahydroisoquinoline-(3S)-carboxylic Acid IR ν (nujol) cm$^{-1}$; 2725, 2509, 1917, 1732, 1682, 1614, 1589, 1531. $^1$H-NMR (CDCl$_3$) δ (ppm): 0.93 (3H, t, J=7.1 Hz), 1.20-1.70 (2H, m), 2.00-2.38 (2H, m), 2.23 (3H, s), 2.59-2.87 (2H, m), 2.91-3.52 (2H, m), 3.64-4.00 (2H, m), 4.21-5.03 (2H, m), 5.03-5.47 (1H, m), 6.18 (1H, d, J=16.3 Hz), 6.42-6.85 (3H, m), 7.05 (1H, d, J=8.4 Hz), 7.14-7.68 (1H, br).

Reference Example 38 methyl 7-{2-[2-(trans-2-cyclohexylvinyl)-5-methyloxazol-4-yl]ethoxy}-1,2,3,4-tetrahydroisoquinoline-(3S)-carboxylate IR ν (neat) cm$^{-1}$; 2926, 2851, 1740, 1641, 1612, 1582, 1533, 1504. $^1$H-NMR (CDCl$_3$) δ (ppm): 0.80-2.45 (11H, m), 2.27 (3H, s), 2.70-3.20 (2H, m), 2.86 (2H, t, J=7.0 Hz), 3.55-3.85 (1H, m), 3.76 (3H, s), 4.04 (2H, s), 4.14 (2H, t, J=6.8 Hz), 6.12 (1H, d, J=16.0 Hz), 6.40-6.80 (3H, m), 6.99 (1H, d, J=8.4 Hz).

Reference Example 39 methyl 7-{2-[2-(trans-2-cyclohexylvinyl)-5-methyloxazol-4-yl]ethoxy}-2-(2,4-hexadienoyl)-1,2,3,4-tetrahydroisoquinoline-(3S)-carboxylate IR ν (nujol) cm$^{-1}$; 1745, 1614, 1531, 1506. $^1$H-NMR (CDCl$_3$) δ (ppm): 0.85-2.45 (14H, m), 2.27 (3H, s), 2.87 (2H, t, J=6.8 Hz), 3.00-3.35 (2H, m), 3.59 (3H, s), 4.15 (2H, t, J=6.8 Hz), 4.30-5.65 (3H, m), 6.00-7.55 (7H, m), 6.50 (1H, d, J=6.4 Hz), 7.03 (1H, d, J=8.4 Hz).

Reference Example 40

7-{2-[2-(trans-2-cyclohexylvinyl)-5-methyloxazol-4-yl]ethoxy}-2-(2,4-hexadienoyl)-1,2,3,4-tetrahydroisoquinoline-(3S)-carboxylic acid tert-butylamine Salt IR ν (nujol) cm$^{-1}$; 2739, 2635, 2548, 1655, 1630, 1560, 1506. $^1$H-NMR (CDCl$_3$) δ (ppm): 0.98 (9H, s), 1.00-2.40 (14H, m), 2.27 (3H, s), 2.85 (2H, t, J=6.8 Hz), 2.90-3.30 (2H, m), 4.10 (2H, t, J=6.8 Hz), 4.20-5.20 (3H, m), 5.80-7.45 (12H, m).

Reference Example 41

2-cinnamoyl-7-[2-(5-methyl-2-(trans-1-penten-1-yl)oxazol-4-yl)ethoxy]-1,2,3,4-tetrahydroisoquinoline-(3S)-carboxylic Acid IR ν (nujol) cm$^{-1}$; 1728, 1647, 1612, 1578, 1533, 1506. $^1$H-NMR (DMSO-d$_6$) δ (ppm): 0.89 (3H, t, J=7.3 Hz), 1.20-1.70 (2H, m), 1.95-2.25 (2H, m), 2.26 (3H, s), 2.65-2.95 (2H, m), 2.95-3.15 (2H, m), 3.60-5.80 (1H, br), 3.95-4.35 (2H, m), 4.40-5.60 (3H, m), 6.19 (1H, d, J=16.5 Hz), 6.33-6.90 (3H, m), 7.11 (1H, d, J=8.4 Hz), 7.30-7.95 (7H, m).

Reference Example 42

7-{2-[2-(3-ethyl-trans-1-penten-1-yl)-5-methyloxazol-4-yl]ethoxy}-2-(2,4-hexadienoyl)-1,2,3,4-tetrahydroisoquinoline-(3S)-carboxylic Acid tert-butylamine Salt IR ν (nujol) cm$^{-1}$; 2735, 2633, 2544, 1653, 1624, 1599, 1551, 1506. $^1$H-NMR (CDCl$_3$) δ (ppm): 0.87 (6H, t, J=7.2 Hz), 0.96 (9H, s), 1.20-1.63 (4H, m), 1.63-2.10 (4H, m), 2.28 (3H, s), 2.86 (2H, t, J=6.8 Hz), 2.90-3.30 (2H, m), 4.11 (2H, t, J=6.8 Hz), 4.40-5.30 (3H, m), 5.80-7.60 (12H, m).

Reference Example 43

7-{2-[2-(3,3-dimethyl-trans-1-buten-1-yl)-5-methyloxazol-4-yl]ethoxy}-2-(2,4-hexadienoyl)-1,2,3,4-tetrahydroisoquinoline-(3S)-carboxylic acid tert-butylamine Salt IR ν (nujol) cm$^{-1}$; 3568, 2745, 2637, 2216, 1653, 1553. $^1$H-NMR (CDCl$_3$) δ (ppm); 0.97 (18H, s), 1.60-2.00 (3H, m), 2.28 (3H, s), 2.86 (2H, t, J=6.5 Hz), 2.90-3.35 (2H, m), 4.11 (2H, t, J=6.5 Hz), 4.28-5.20 (3H, m), 5.90-7.48 (12H, m).

Reference Example 44

7-{2-[2-(3,3-dimethyl-trans-1-penten-1-yl)-5-methyloxazol-4-yl]ethoxy}-2-(2,4-hexadienoyl)-1,2,3,4-tetrahydroisoquinoline-(3S)-carboxylic Acid tert-butylamine Salt IR ν (nujol) cm$^{-1}$; 3400, 2745, 2635, 2544, 2220, 1651, 1622, 1553. $^1$H-NMR (CDCl$_3$) δ (ppm); 0.82 (3H, t, J=7.3 Hz), 0.98 (9H, S), 1.05 (6H, s), 1.41 (2H, q, J=7.3 Hz), 1.63-1.94 (3H, m), 2.28 (3H, s), 2.86 (2H, t, J=6.8 Hz), 2.90-3.37 (2H, m), 4.11 (2H, t, J=6.8 Hz), 4.23-5.20 (3H, m), 6.09 (1H, d, J=16.3 Hz), 6.00-7.39 (11H, m).

Reference Example 45

7-{2-[2-(4,4-dimethyl-trans-1-penten-1-yl)-5-methyloxazol-4-yl]ethoxy}-2-(2,4-hexadienoyl)-1,2,3,4-tetrahydroisoquinoline-(3S)-carboxylic Acid tert-butylamine Salt IR ν (nujol) cm$^{-1}$; 2733, 2635, 2550, 1657, 1634, 1611, 1558, 1506. $^1$H-NMR (CDCl$_3$) δ (ppm); 0.94 (9H, s), 1.01 (9H, s), 1.65-1.95 (3H, m), 2.09 (2H, d, J=7.5 Hz), 2.28 (3H, s), 2.86 (2H, t, J=6.6 Hz), 2.90-3.30 (2H, m), 4.11 (2H, t, J=6.6 Hz), 4.25-5.20 (3H, m), 5.90-7.35 (12H, m).

Reference Example 46

2-(2,4-hexadienoyl)-7-{2-[5-methyl-2-(3-methyl-trans-1-buten-1-yl)oxazol-4-yl]ethoxy}-1,2,3,4-tetrahydroisoquinoline-(3S)-carboxylic Acid tert-butylamine Salt IR ν (nujol) cm$^{-1}$; 2741, 2633, 2544, 1651, 1622, 1553, 1506. $^1$H-NMR (CDCl$_3$) δ (ppm); 1.01 (9H, s), 1.08 (6H, d, J=6.7 Hz), 1.65-1.95 (3H, m), 2.28 (3H, s), 2.35-2.70 (1H, m), 2.86 (2H, t, J=6.6 Hz), 2.85-3.30 (2H, m), 4.11 (2H, t, J=6.6 Hz), 4.25-5.20 (3H, m), 5.85-8.00 (12H, m).

Reference Example 47

2-(5-methyl-2-hexenoyl)-7-{2-[5-methyl-2-(trans-1-penten-1-yl)oxazol-4-yl]ethoxy}-1,2,3,4-tetrahydroisoquinoline-(3S)-carboxylic Acid tert-butylamine Salt IR ν (nujol) cm$^{-1}$; 3398, 2741, 2635, 2548, 1661, 1614, 1553.
$^1$H-NMR (CDCl$_3$) δ (ppm); 0.70-1.14 (18H, m), 1.14-2.20 (7H, m), 2.27 (3H, s), 2.85 (2H, br-t), 2.90-3.40 (2H, m), 4.10 (2H, br-t), 4.40-5.20 (3H, m), 5.80-7.10 (10H, m).

Reference Example 48

2-(4,4-dimethyl-2-pentenoyl)-7-{2-[5-methyl-2-(trans-1-penten-1-yl)oxazol-4-yl]ethoxy}-1,2,3,4-tetrahydroisoquinoline-(3S)-carboxylic Acid tert-butylamine Salt IR ν (nujol) cm$^{-1}$; 2741, 2633, 1622, 1556, 1504. $^1$H-NMR (CDCl$_3$) δ (ppm); 0.94 (3H, t, J=7.5 Hz), 1.05 (9H, S), 1.10 (9H, s), 1.20-1.70 (2H, m), 2.05-2.45 (2H, m), 2.28 (3H, s), 2.86 (2H, t, J=6.3 Hz), 2.95-3.30 (2H, m), 4.11 (2H, t, J=6.3 Hz), 4.30-5.20 (3H, m), 5.00-6.00 (3H, br), 6.00-7.20 (7H, m).

Reference Example 49

2-(2,4-hexadienoyl)-7-{2-[5-methyl-2-(trans-2-thiophen-2-ylvinyl)oxazol-4-yl]ethoxy}-1,2,3,4-tetrahydroisoquinoline-(3S)-carboxylic Acid tert-butylamine Salt IR ν (nujol) cm$^{-1}$; 3420, 2737, 2633, 2548, 1651, 1622, 1558, 1504. $^1$H-NMR (CDCl$_3$) δ (ppm); 0.97 (9H, s), 1.83 (3H, br-d), 2.31 (3H, s), 2.89 (2H, t, J=6.3 Hz), 2.90-3.23 (2H, m), 4.13 (2H, t, J=6.3 Hz), 4.30-5.20 (3H, m), 6.00-6.78 (10H, m), 6.85-7.37 (2H, m), 7.49 (1H, d, J=16.4 Hz).

Reference Example 50

2-(2-heptenoyl)-7-{2-[5-methyl-2-phenylsulfanyloxazol-4-yl]ethoxy}-1,2,3,4-tetrahydroisoquinoline-(3S)-carboxylic Acid IR ν (nujol) cm$^{-1}$; 2571, 1732, 1657, 1614, 1583, 1506. $^1$H-NMR (CDCl$_3$) δ (ppm); 0.91 (3H, br-t), 1.10-1.70 (4H, m), 2.82 (2H, t, J=6.8 Hz), 1.90-2.40 (2H, m), 2.22 (3H, s), 2.95-3.40 (2H, m), 4.07 (2H, t, J=6.8 Hz), 4.20-5.65 (3H, m), 6.32 (1H, d, J=16.2 Hz), 6.50-6.85 (4H, m), 7.04 (1H, d, J=7.7 Hz), 7.20-7.65 (5H, m).

Reference Example 51

2-(2,4-hexadienoyl)-7-{2-[2-(trans-1-penten-1-yl)-5-propyloxazol-4-yl]ethoxy}-1,2,3,4-tetrahydroisoquinoline-(3S)-carboxylic Acid tert-butylamine Salt IR ν (nujol) cm$^{-1}$; 2731, 2633, 2546, 1630, 1553, 1504. $^1$H-NMR (CDCl$_3$) δ (ppm); 0.91 (6H, t, J=7.0 Hz), 0.96 (9H, s), 1.25-2.00 (7H, m), 2.20 (2H, q, J=7.0 Hz), 2.60 (2H, t, J=7.0 Hz), 2.87 (2H, t, J=6.6 Hz), 2.90-3.30 (2H, m), 4.11 (2H, t, J=6.6 Hz), 4.25-5.20 (3H, m), 5.80-7.40 (12H, m).

Reference Example 52

2-(2,2-difluorobutyryl)-7-{2-[5-methyl-2-(trans-1-penten-1-yl)oxazol-4-yl]ethoxy}-1,2,3,4-tetrahydroisoquinoline-(3S)-carboxylic Acid tert-butylamine Salt IR ν (nujol) cm$^{-1}$; 2745, 2638, 2552, 1661, 1614, 1564, 1506. $^1$H-NMR (CDCl$_3$) δ (ppm); 0.75-2.20 (6H, m), 1.25-1.70 (2H, m), 1.85-2.45 (4H, m), 0.93 (9H, s), 1.26-2.70 (11H, m), 2.27 (3H, s), 2.86 (2H, t, J=6.6 Hz), 2.95-3.25 (2H, m), 4.11 (2H, t, J=6.6 Hz), 4.30-5.15 (3H, m), 6.17 (1H, d, J=16.3 Hz), 6.35-7.50 (7H, m).

Reference Example 53

2-(4,4-difluoropentanoyl)-7-{2-[5-methyl-2-(trans-1-penten-1-yl)oxazol-4-yl]ethoxy}-1,2,3,4-tetrahydroisoquinoline-(3S)-carboxylic Acid tert-butylamine Salt IR ν (nujol) cm$^{-1}$; 3398, 2745, 2637, 2550, 1645, 1556. $^1$H-NMR (CDCl$_3$) δ (ppm); 0.95 (3H, t, J=7.5 Hz), 0.99 (3H, s), 1.26-2.70 (11H, m), 2.28 (3H, s), 2.86 (2H, br-t), 3.00-3.41 (2H, m), 4.11 (2H, br-t), 4.36-4.70 (2H, m), 4.80-5.10 (1H, m), 5.57-6.14 (3H, br), 6.16 (1H, d, J=16.3 Hz), 6.41-6.80 (3H, m), 6.83-7.08 (1H, m).

Reference Example 54

7-{2-[5-methyl-2-(trans-1-penten-1-yl)oxazol-4-yl]ethoxy}-2-(3,3,3-trifluoropropionyl)-1,2,3,4-tetrahydroisoquinoline-(3S)-carboxylic Acid IR ν (nujol) cm$^{-1}$; 2723, 2621, 1732, 1661, 1614, 1506. $^1$H-NMR (CDCl$_3$) δ (ppm); 0.95 (3H, t, J=7.5 Hz), 1.20-1.75 (2H, m), 2.23 (2H, t, J=6.8 Hz), 2.34 (3H, s), 2.94 (2H, br-t), 3.00-3.60 (4H, m), 4.09 (2H, br-t), 4.30-5.50 (3H, m), 6.36 (1H, d, J=16.0 Hz), 7.04 (1H, d, J=7.7 Hz), 6.50-6.95 (3H, m), 8.93 (1H, br-s).

Reference Example 55

2-(2,4-hexadienoyl)-7-{2-[5-methyl-2-(2-methylsulfanylethyl)oxazol-4-yl]ethoxy}-1,2,3,4-tetrahydroisoquinoline-(3S)-carboxylic Acid tert-butylamine Salt IR ν (nujol) cm$^{-1}$; 2745, 2637, 2548, 1651, 1624, 1601, 1553, 1504. $^1$H-NMR (CDCl$_3$) δ (ppm); 0.97 (9H, s), 1.65-2.00 (3H, m), 2.11 (3H, s), 2.25 (3H, s), 2.70-5.40 (6H, m), 2.85 (2H, t, J=6.8 Hz), 4.10 (2H, t, J=6.8 Hz), 4.25-5.20 (3H, m), 5.80-7.40 (12H, m).

Reference Example 56

2-(2,4-hexadienoyl)-7-(2-{5-methyl-2-[2-trans-(1-methylcyclohexan-1-yl)vinyl]oxazol-4-yl}ethoxy)-1,2,3,4-tetrahydroisoquinoline-(3S)-carboxylic Acid tert-butylamine Salt IR ν (nujol) cm$^{-1}$; 2739, 2631, 2548, 1651, 1622, 1599, 1585, 1547, 1508. $^1$H-NMR(CDCl$_3$) δ (ppm); 0.97 (9H, s), 1.05 (3H, s), 1.15-2.00 (13H, m), 2.28 (3H, s), 2.86 (2H, t, J=6.6 Hz), 2.90-3.40 (2H, m), 4.11 (2H, t, J=6.6 Hz), 4.25-5.20 (3H, m), 5.85-7.50 (12H, m).

Reference Example 57

2-(2,4-hexadienoyl)-7-(2-{5-methyl-2-[2-trans-(1-methylcyclopentan-1-yl)vinyl]oxazol-4-yl}ethoxy)-1,2,3,4-tetrahydroisoquinoline-(3S)-carboxylic Acid tert-butylamine Salt IR ν (nujol) cm$^{-1}$; 2739, 2633, 2544, 1634, 1549, 1504. $^1$H-NMR (CDCl$_3$) δ (ppm); 0.99 (9H, s), 1.14 (3H, s), 1.30-2.05 (11H, m), 2.28 (3H, s), 2.86 (2H, t, J=6.8 Hz), 2.90-3.40 (2H, m), 4.11 (2H, t, J=6.8 Hz), 4.25-5.20 (3H, m), 5.80-7.45 (12H, m).

Reference Example 58

7-{2-[5-methyl-2-(4-methyl-trans-1-penten-1-yl)oxazol-4-yl]ethoxy}-2-(4-pentenyl)-1,2,3,4-tetrahydroisoquinoline-(3S)-carboxylic acid (1) Methyl 7-{2-[5-methyl-2-(4-methyl-trans-1-penten-1-yl)oxazol-4-yl]ethoxy}-1,2,3,4-tetrahydroisoquinoline-(3S)-carboxylate (1.0 g) was dissolved in N,N-dimethylformamide (10 ml), triethylamine (1.4 ml) and 5-bromo-1-pentene (1.2 ml) were added, and the mixture was stirred at room temperature for 40 hr. Triethylamine (1.05 ml) and 5-bromo-1-pentene (0.89 ml) were added, and the mixture was further stirred for 26 hr. Ethyl acetate (20 ml) was added, and the mixture was washed with water (50 ml, twice), 10% aqueous citric acid and saturated brine (10 ml, respectively), and the dried over Na$_2$SO$_4$. The ethyl acetate was evaporated under reduced pressure. The obtained residue was purified by silica gel column chromatography to give methyl 7-{2-[5-methyl-2-(4-methyl-trans-1-penten-1-yl)oxazol-4-yl]ethoxy}-2-(4-pentenyl)-1,2,3,4-tetrahydroisoquinoline-(3S)-carboxylate (0.89 g) as an oil.

IR ν (neat) cm$^{-1}$; 3449, 2953, 2928, 2870, 1738, 1641, 1614, 1533, 1506. $^1$H-NMR (CDCl$_3$) δ (ppm); 0.94 (6H, d, J=6.3 Hz), 1.40-1.90 (3H, m), 1.90-2.33 (4H, m), 2.27 (3H, s), 2.50-3.17 (6H, m), 3.65 (3H, s), 3.70-4.25 (5H, m), 4.80-5.13 (2H, m), 5.45-6.00 (1H, m), 6.16 (1H, d, J=16.0 Hz), 6.36-6.79 (3H, m), 6.97 (1H, d, J=8.4 Hz).

(2) The compound (0.8 g) obtained in the above-mentioned (1) was dissolved in a mixed solvent (23 ml) of tetrahydrofuran-methanol (3:1), 1M aqueous lithium hydroxide solution (5.66 ml) was added, and the mixture was stirred at room temperature for 40 min. The mixture was acidified with 10% aqueous citric acid, and the solution was concentrated under reduced pressure. The precipitated gum-like substance was extracted with ethyl acetate (20 ml), the ethyl acetate layer was washed with saturated brine (20 ml), and dried over Na$_2$SO$_4$. The ethyl acetate was evaporated under reduced pressure. n-Hexane was added to the residue and the precipitated crystals were collected by filtration to give the title compound (0.74 g).

IR ν (nujol) cm$^{-1}$; 3400, 3057, 2725, 2664, 2565, 2494, 1626, 1551, 1508. $^1$H-NMR (CDCl$_3$) δ (ppm); 0.93 (6H, d, J=6.4 Hz), 1.48-2.30 (7H, m), 2.28 (3H, s), 2.60-3.33 (6H, m), 3.72 (1H, br-t), 3.82-4.46 (4H, m), 4.80-5.20 (2H, m), 5.42-5.97 (1H, m), 6.15 (1H, d, J=16.1 Hz), 6.40-6.90 (3H, m), 7.08 (1H, d, J=8.4 Hz), 8.55-9.05 (1H, br).

Reference Example 59

2-benzyl-7-{2-[5-methyl-2-(4-methyl-trans-1-penten-1-yl)oxazol-4-yl]ethoxy}-1,2,3,4-tetrahydroisoquinoline-(3S)-carboxylic Acid (1) Methyl 2-benzyl-7-hydroxy-1,2,3,4-tetrahydroisoquinoline-(3S)-carboxylate (483 mg) and 2-[5-methyl-2-(4-methyl-trans-1-penten-1-yl)oxazol-4-yl]ethyl methanesulfonate (700 mg) were dissolved in toluene (15 ml), potassium carbonate (674 mg) and tetraethyl ammonium fluoride hydrate (100 mg) were added, and the mixture was stirred at 90° C. for 18 hr. Ethyl acetate (10 ml) was added to the reaction mixture, and the mixture was washed successively with water (20 ml) and saturated brine (20 ml), and the dried over Na$_2$SO$_4$. The solvent was evaporated under reduced pressure. The obtained residue was purified by silica gel column chromatography to give methyl 2-benzyl-7-{2-[5-methyl-2-(4-methyl-trans-1-penten-1-yl)oxazol-4-yl]ethoxy}-1,2,3,4-tetrahydroisoquinoline-(3S)-carboxylate (590 mg).

IR ν (neat) cm$^{-1}$; 3443, 3027, 2953, 2926, 2871, 2841, 1739, 1613, 1534, 1505. $^1$H-NMR (CDCl$_3$) δ (ppm); 0.93 (6H, d, J=6.4 Hz), 1.48-2.00 (1H, m), 2.10 (2H, t, J=6.8 Hz), 2.26 (3H, s), 2.84 (2H, t, J=6.8 Hz), 3.08 (2H, d, J=4.6 Hz), 3.66 (3H, s), 3.70-4.30 (5H, m), 3.90 (2H, s), 6.15 (1H, d, J=16.1 Hz), 6.38-6.78 (3H, m), 6.98 (1H, d, J=8.2 Hz), 7.16-7.50 (5H, m).

(2) The compound (1) (570 mg) obtained in the above-mentioned (1) was dissolved in a mixed solvent (14 ml) of tetrahydrofuran-methanol (3:1), 1M aqueous lithium hydroxide solution (3.5 ml) was added, and the mixture was stirred at 40° C. for 1.5 hr. The mixture was acidified with 6M hydrochloric acid, and the solution was concentrated under reduced pressure. The precipitated gum-like substance was extracted with ethyl acetate (15 ml), and the ethyl acetate layer was washed with saturated brine (10 ml), and dried over Na$_2$SO$_4$ The ethyl acetate was evaporated under reduced pressure. n-Hexane was added to the obtained residue, the mixture was stirred under ice-cooling for 30 min, and the precipitated crystals were collected by filtration to give the title compound (445 mg).
IR ν (nujol) cm$^{-1}$; 3385, 3047, 1718, 1636, 1585, 1549, 1533, 1501. $^1$H-NMR (CDCl$_3$) δ (ppm): 0.93 (6H, d, J=6.4 Hz), 1.46-1.99 (1H, m), 2.10 (2H, t, J=6.7 Hz), 2.27 (3H, s), 2.85 (2H, t, J=6.8 Hz), 3.19 (2H, d, J=6.1 Hz), 3.63-4.40 (5H, m), 4.03 (2H, s), 6.15 (1H, d, J=15.8 Hz), 6.36-6.85 (3H, m), 7.06 (1H, d, J=8.6 Hz), 7.20-7.60 (5H, m), 9.37 (1H, br-s).

Reference Example 60

2-benzyl-7-{2-[2-(3,3-dimethyl-trans-1-buten-1-yl)-5-methyloxazol-4-yl]ethoxy}-1,2,3,4-tetrahydroisoquinoline-(3S)-carboxylic Acid IR ν (nujol) cm$^{-1}$; 3420, 1680, 1614, 1506. $^1$H-NMR (DMSO-d$_6$) δ (ppm); 1.07 (9H, s), 2.23 (3H, s), 2.77 (2H, t, J=6.3 Hz), 2.80-3.10 (2H, m), 3.20-4.60 (8H, m), 6.07 (1H, d, J=16.5 Hz), 6.59 (1H, d, J=16.5 Hz), 6.40-6.80 (2H, m), 7.01 (1H, J=8.4 Hz), 7.32 (5H, br-s).

Reference Example 61

2-(2,2-dimethylpropyl)-7-{2-[5-methyl-2-(4-methyl-trans-1-penten-1-yl)oxazol-4-yl]ethoxy}-1,2,3,4-tetrahydroisoquinoline-(3S)-carboxylic acid tert-butylamine salt IR ν (nujol) cm$^{-1}$; 3398, 2746, 2637, 2554, 1641, 1612, 1543. $^1$H-NMR (CDCl$_3$) δ (ppm); 0.87 (9H, s), 0.93 (6H, d, J=6.6 Hz), 1.02 (9H, s), 1.48-2.00 (1H, m), 2.11 (2H, t, J=6.8 Hz), 2.28 (3H, s), 2.48 (2H, d, J=7.9 Hz), 2.60-3.20 (2H, m), 2.86 (2H, t, J=6.8 Hz), 3.30-3.53 (1H, m), 4.00 (2H, dd, J=16.6 Hz, 52.7 Hz), 4.11 (2H, t, J=6.8 Hz), 6.16 (1H, d, J=16.0 Hz), 6.37-7.00 (6H, m), 6.90 (1H, d, J=8.1 Hz).

Reference Example 62

7-{2-[5-methyl-2-(trans-1-penten-1-yl)oxazol-4-yl]ethoxy}-2-(2,2,3,3,3-pentafluoropropyl)-1,2,3,4-tetrahydroisoquinoline-(3S)-carboxylic Acid IR ν (nujol) cm$^{-1}$; 1697, 1610, 1529, 1508. $^1$H-NMR (DMSO-d$_6$) δ (ppm); 0.89 (3H, t, J=7.3 Hz), 1.20-1.70 (2H, m), 1.95-2.25 (2H, m), 2.25 (3H, s), 2.00-4.40 (1H, br), 2.79 (2H, m), 2.95-3.15 (2H, m), 3.30-4.40 (7H, m), 6.19 (1H, d, J=16.5 Hz), 6.33-6.90 (3H, m), 7.02 (1H, d, J=8.1 Hz).

Reference Example 63

7-{2-[5-methyl-2-(trans-1-penten-1-yl)oxazol-4-yl]ethoxy}-2-(3,3,3-trifluoropropyl)-1,2,3,4-tetrahydroisoquinoline-(3S)-carboxylic Acid IR ν (nujol) cm$^{-1}$; 1616, 1506. $^1$H-NMR (CDCl$_3$) δ (ppm); 0.93 (3H, t, J=6.8 Hz), 1.30-1.75 (2H, m), 2.10-2.70 (4H, m), 2.27 (3H, s), 2.75-3.40 (6H, m), 3.60-4.20 (5H, m), 5.80-8.00 (1H, br), 6.10-6.80 (4H, m), 7.02 (1H, d, J=8.1 Hz).

Reference Example 64

2-(3-butenyl)-7-{2-[5-methyl-2-(4-methyl-trans-1-penten-1-yl)oxazol-4-yl]ethoxy}-1,2,3,4-tetrahydroisoquinoline-(3S)-carboxylic Acid IR ν (nujol) cm$^{-1}$; 3385, 3080, 2725, 2583, 1717, 1614, 1533, 1506. $^1$H-NMR (CDCl$_3$) δ (ppm); 0.93 (6H, d, J=6.4 Hz), 1.48-1.99 (1H, m), 2.11 (2H, t, J=6.7 Hz), 2.28 (3H, s), 2.35-2.62 (2H, m), 2.70-3.35 (6H, m), 3.76 (1H, br-t), 3.85-4.46 (4H, m), 4.90-5.25 (2H, m), 5.45-5.98 (1H, m), 6.15 (1H, d, J=16.1 Hz), 6.40-6.86 (3H, m), 7.08 (1H, d, J=8.2 Hz), 8.60-9.00 (1H, br).

Reference Example 65

2-(2,4-hexadienoyl)-7-{2-[2-(3-methoxy-trans-1-propen-1-yl)-5-methyloxazol-4-yl]ethoxy}-1,2,3,4-tetrahydroisoquinoline-(3S)-carboxylic Acid tert-butylamine Salt IR ν (nujol) cm$^{-1}$; 2737, 1652, 1624, 1599, 1555, 1587, 1506. $^1$H-NMR (CDCl$_3$) δ (ppm); 1.00 (9H, s), 1.85-2.00 (3H, m), 2.29 (3H, s), 2.87 (2H, t, J=6.8 Hz), 2.90-3.25 (2H, m), 3.38 (3H, s), 3.95-4.20 (2H, m), 4.11 (2H, t, J=6.8 Hz), 4.30-5.20 (3H, m), 5.90-8.40 (12H, m).

Reference Example 66

7-{2-[2-(5-fluoro-trans-1-penten-1-yl)-5-methyloxazol-4-yl]ethoxy}-2-(2,4-hexadienoyl)-1,2,3,4-tetrahydroisoquinoline-(3S)-carboxylic Acid tert-butylamine Salt IR ν (nujol) cm$^{-1}$; 2735, 2631, 2544, 2432, 2365, 2212, 1651, 1624, 1599, 1553, 1504. $^1$H-NMR (CDCl$_3$) δ (ppm); 0.99 (9H, s), 1.50-2.10 (5H, m), 2.15-2.55 (2H, m), 2.28 (3H, s), 2.80-3.40 (2H, m), 2.86 (2H, t, J=6.6 Hz), 4.11 (2H, t, J=6.6 Hz), 4.47 (2H, dt, J=47.0, 5.7 Hz), 4.50-5.20 (3H, m), 5.80-6.80 (9H, m), 6.85-7.25 (2H, m).

Reference Example 67

7-[2-(2-cyclopentylidenemethyl-5-methyloxazol-4-yl)ethoxy]-2-(2,4-hexadienoyl)-1,2,3,4-tetrahydroisoquinoline-(3S)-carboxylic Acid tert-butylamine Salt IR ν (nujol) cm$^{-1}$; 2737, 2631, 2544, 1653, 1624, 1587, 1553, 1506. $^1$H-NMR (CDCl$_3$) δ (ppm); 0.96 (9H, s), 1.50-2.05 (7H, m), 2.28 (3H, s), 2.25-2.55 (2H, m), 2.55-3.30 (4H, m), 2.87 (2H, t, J=6.8 Hz), 4.12 (2H, t, J=6.8 Hz), 4.25-5.20 (3H, m), 5.80-7.40 (11H, m).

Reference Example 68

7-[2-(2-cyclohexylidenemethyl-5-methyloxazol-4-yl)ethoxy]-2-(2,4-hexadienoyl)-1,2,3,4-tetrahydroisoquinoline-(3S)-carboxylic Acid tert-butylamine Salt IR ν (nujol) cm$^{-1}$; 2739, 2631, 2542, 1653, 1624, 1549, 1506. $^1$H-NMR (CDCl$_3$) δ (ppm); 1.01 (9H, s), 1.40-2.00 (9H, m), 2.10-2.40 (2H, m), 2.27 (3H, s), 2.65-3.40 (6H, m), 2.86 (2H, t, J=6.6 Hz), 4.12 (2H, t, J=6.6 Hz), 4.25-5.20 (3H, m), 5.80-7.40 (11H, m), 5.93 (1H, s).

Reference Example 69

2-cyclopentylideneacetyl-7-(2-[5-methyl-2-(4-methyl-trans-1-penten-1-yl)oxazol-4-yl]ethoxy]-1,2,3,4-tetrahydroisoquinoline-(3S)-carboxylic Acid tert-butylamine Salt IR ν (nujol) cm$^{-1}$; 2745, 2638, 2554, 1655, 1556, 1506. $^1$H-NMR (CDCl$_3$) δ (ppm); 0.94 (6H, d, J=6.8 Hz), 0.97 (9H, s), 1.43-2.00 (5H, m), 2.11 (2H, t, J=6.7 Hz), 2.28 (3H, s), 2.30-2.8 (4H, m), 2.86 (2H, t, J=6.8 Hz), 2.90-3.40 (2H, m), 4.11 (2H, t, J=6.8 Hz), 4.20-5.20 (3H, m), 5.93-6.28 (1H, m), 6.40-6.80 (3H, m), 6.80-7.20 (4H, m).

Reference Example 70

2-cyclohexylideneacetyl-7-(2-[5-methyl-2-(4-methyl-trans-1-penten-1-yl)oxazol-4-yl]ethoxy]-1,2,3,4-tetrahydroisoquinoline-(3S)-carboxylic Acid tert-butylamine Salt IR ν (nujol) cm$^{-1}$; 2743, 2637, 2554, 2216, 1636, 1556, 1506. $^1$H-NMR (CDCl$_3$) δ (ppm); 0.93 (6H, d, J=6.4 Hz), 1.02 (9H, s), 1.33-1.80 (7H, m), 2.00-2.50 (6H, m), 2.28 (3H, s), 2.86 (2H, t, J=6.7 Hz), 2.95-3.42 (2H, m), 4.11 (2H, t, J=6.7 Hz), 4.27-5.20 (3H, m), 5.64 (1H, d, J=7.7 Hz), 6.16 (1H, d, J=14.8 Hz), 6.40-6.80 (3H, m), 6.80-7.30 (4H, m).

Reference Example 71 methyl 7-{2-[2-(5-tert-butylsulfanyl-trans-1-penten-1-yl)-5-methyloxazol-4-yl]ethoxy}-1,2,3,4-tetrahydroisoquinoline-(3S)-carboxylate IR ν (neat) cm$^{-1}$; 2928, 2864, 1740, 1638, 1612, 1578, 1533, 1504. $^1$H-NMR (CDCl$_3$) δ (ppm); 1.32 (9H, s), 1.60-2.00 (2H, m), 1.98 (1H, br-s), 2.15-2.40 (2H, m), 2.27 (3H, s), 2.56 (2H, t, J=7.2 Hz), 2.80-3.05 (2H, m), 2.86 (2H, t, J=6.7 Hz), 3.55-3.80 (1H, m), 3.76 (3H, s), 4.04 (2H, br-s), 4.16 (2H, t, J=6.7 Hz), 6.17 (1H, d, J=16.0 Hz), 6.40-6.80(3H, m), 6.99(1H, d, J=8.3 Hz).

Reference Example 72 methyl 7-{2-[2-(5-tert-butylsulfanyl-trans-1-penten-1-yl)-5-methyloxazol-4-yl]ethoxy}-2-(2,4-hexadienoyl)-1,2,3,4-tetrahydroisoquinoline-(3S)-carboxylate IR ν (neat) cm$^{-1}$; 2957, 2926, 2862, 1740, 1655, 1612, 1506. $^1$H-NMR (CDCl$_3$) δ (ppm); 1.32 (9H, s), 1.60-2.00 (5H, m), 2.15-2.40 (2H, m), 2.28 (3H, s), 2.57 (2H, t, J=7.5 Hz), 2.87 (2H, t, J=6.6 Hz), 3.00-3.25 (2H, m), 3.59 (3H, s), 4.15 (2H, t, J=6.6 Hz), 4.35-5.60 (3H, m), 5.90-6.85 (7H, m), 7.04 (1H, d, J=8.4 Hz), 7.15-7.50 (1H, m).

Reference Example 73

7-{2-[2-(5-tert-butylsulfanyl-trans-1-penten-1-yl)-5-methyloxazol-4-yl]ethoxy}-2-(2,4-hexadienoyl)-1,2,3,4-tetrahydroisoquinoline-(3S)-carboxylic Acid tert-butylamine Salt IR ν (nujol) cm$^{-1}$; 2743, 2635, 2548, 1742, 1655, 1628, 1601, 1555, 1506. $^1$H-NMR (CDCl$_3$) δ (ppm); 1.00 (9H, s), 1.32 (9H, s), 1.60-2.00 (5H, m), 2.15-2.40 (2H, m), 2.28 (3H, s), 2.56 (2H, t, J=7.2 Hz), 2.86 (2H, t, J=6.3 Hz), 2.90-3.35 (2H, m), 4.11 (2H, t, J=6.3 Hz), 4.30-5.15 (3H, m), 5.90-7.35 (12H, m).

Reference Example 74 methyl 7-{2-[2-(5-dimethylamino-trans-1-penten-1-yl)-5-methyloxazol-4-yl]ethoxy}-2-(2,4-hexadienoyl)-1,2,3,4-tetrahydroisoquinoline-(3S)-carboxylate IR ν (neat) cm$^{-1}$; 3404, 2949, 2860, 2818, 2770, 1743, 1655, 1626, 1603, 1533, 1506. $^1$H-NMR (CDCl$_3$) δ (ppm); 1.40-1.95 (5H, m), 2.10-2.40 (4H, m), 2.23 (6H, s), 2.28 (3H, s), 2.87 (2H, t, J=6.6 Hz), 3.05-3.25 (2H, m), 3.59 (3H, s), 4.14 (2H, t, J=6.6 Hz), 4.60-5.00 (2H, m), 5.40-5.70 (1H, m), 6.00-6.80 (7H, m), 6.90-7.35 (2H, m).

Reference Example 75

7-{2-[2-(5-dimethylamino-trans-1-penten-1-yl)-5-methyloxazol-4-yl]ethoxy}-2-(2,4-hexadienoyl)-1,2,3,4-tetrahydroisoquinoline-(3S)-carboxylic Acid Sodium Salt IR ν (nujol) cm$^{-1}$; 3381, 2766, 2725, 1651, 1595, 1535, 1504. $^1$H-NMR (CDCl$_3$) δ (ppm); 1.40-1.95 (5H, m), 2.05-2.60 (4H, m), 2.25 (9H, s), 2.65-3.10 (4H, m), 3.90-4.10 (2H, m), 4.40-4.80 (2H, m), 5.05-5.55 (1H, m), 5.80-6.75 (7H, m), 6.80-7.25 (2H, m).

Reference Example 76

2-(2-hexenoyl)-7-{2-[5-methyl-2-(4-methyl-trans-1-penten-1-yl)oxazol-4-yl]ethoxy}-1,2,3,4-tetrahydroisoquinoline-(3S)-carboxylic Acid-tert-butylamine Salt IR ν (nujol) cm$^{-1}$; 1661, 1616, 1558, 1506. $^1$H-NMR (CDCl$_3$) δ (ppm); 0.75-2.20 (3H, m), 0.93 (6H, d, J=6.4 Hz), 1.02 (9H, s), 1.20-1.60 (2H, m), 1.60-1.95 (1H, m), 1.95-2.30 (4H, m), 2.10 (2H, t, J=6.6 Hz), 2.27 (3H, s), 2.86 (2H, t, J=6.8 Hz), 3.00-3.40 (2H, m), 4.10 (2H, t, J=6.8 Hz), 4.40-5.20 (3H, m), 6.15 (1H, d, J=16.1 Hz), 6.10-7.20 (9H, m).

Reference Example 77

2-(2,4-hexadienoyl)-7-{2-[2-(4-methyl-trans-1-penten-1-yl)oxazol-4-yl]ethoxy}-1,2,3,4-tetrahydroisoquinoline-(3S)-carboxylic Acid-tert-butylamine Salt IR ν (nujol) cm$^{-1}$; 3435, 2729, 2633, 2548, 2214, 1657, 1630, 1551, 1504. $^1$H-NMR (CDCl$_3$) δ (ppm); 0.94 (6H, d, J=6.6 Hz), 0.97 (9H, s), 1.60-1.90 (4H, m), 2.13 (2H, t, J=6.8 Hz), 2.80-3.20 (2H, m), 3.03 (2H, t, J=6.6 Hz), 4.15 (2H, t, J=6.6 Hz), 4.25-5.20 (3H, m), 6.00-7.30 (12H, m), 7.38 (1H, s).

Reference Example 78

7-{2-[2-(trans-2-cyclopentylvinyl)oxazol-4-yl]ethoxy}-2-(2,4-hexadienoyl)-1,2,3,4-tetrahydroisoquinoline-(3S)-carboxylic Acid-tert-butylamine Salt $^1$H-NMR (CDCl$_3$) δ (ppm); 0.99 (9H, s), 1.20-2.05 (11H, m), 2.38-2.73 (1H, m), 2.90-3.40 (2H, m), 2.94 (2H, t, J=6.5 Hz), 4.14 (2H, t, J=6.5 Hz), 4.26-5.20 (3H, m), 5.86-7.38 (12H, m), 7.50 (1H, s).

Reference Example 79

7-{2-[2-(trans-2-cyclohexylvinyl)oxazol-4-yl]ethoxy}-2-(2,4-hexadienoyl)-1,2,3,4-tetrahydroisoquinoline-(3S)-carboxylic Acid-tert-butylamine Salt $^1$H-NMR (CDCl$_3$) δ (ppm); 0.98 (9H, s), 1.00-2.40 (14H, m), 2.90-3.30 (2H, m), 2.94 (2H, t, J=6.8 Hz), 4.14 (2H, t, J=6.8 Hz), 4.20-5.20 (3H, m), 5.80-7.47 (12H, m), 7.49 (1H, s).

Reference Example 80

2-(2-heptenoyl)-7-{2-[2-(4-methyl-trans-1-penten-1-yl)oxazol-4-yl]ethoxy}-1,2,3,4-tetrahydroisoquinoline-(3S)-carboxylic Acid-tert-butylamine Salt $^1$H-NMR (CDCl$_3$) δ (ppm); 0.75-2.20 (3H, m), 0.93 (6H, d, J=6.4 Hz), 1.02 (9H, s), 1.20-1.60 (4H, m), 1.60-1.95 (1H, m), 1.95-2.30 (2H, m), 2.10 (2H, t, J=6.6 Hz), 2.95 (2H, t, J=6.8 Hz), 3.00-3.40 (2H, m), 4.15 (2H, t, J=6.8 Hz), 4.40-5.20 (3H, m), 6.15 (1H, d, J=16.1 Hz), 6.10-7.20 (9H, m), 7.48 (1H, s).

Reference Example 81

2-(2-hexenoyl)-7-{2-[2-(4-methyl-trans-1-penten-1-yl)oxazol-4-yl]ethoxy}-1,2,3,4-tetrahydroisoquinoline-(3S)-carboxylic Acid-tert-butylamine Salt IR ν (nujol) cm$^{-1}$; 3435, 2729, 2633, 2548, 2214, 1661, 1622, 1553, 1504. $^1$H-NMR (DMSO-d$_6$) δ (ppm); 0.80-1.00 (3H, m), 0.90 (6H, d, J=6.2 Hz), 1.14 (9H, s), 1.20-1.90 (6H, m), 1.95-2.25 (2H, m), 2.70-3.40 (3H, m), 4.10-5.20 (8H, m), 6.10-6.85 (6H, m), 7.00 (1H, d, J=8.4 Hz), 7.78 (1H, s).

Reference Example 82

2-(2,4-hexadienoyl)-7-{2-[2-(trans-1-hexen-1-yl)oxazol-4-yl]ethoxy}-1,2,3,4-tetrahydroisoquinoline-(3S)-carboxylic Acid-tert-butylamine Salt $^1$H-NMR (CDCl$_3$) δ (ppm); 0.75-1.16 (3H, m), 0.98 (9H, s), 1.20-1.60 (4H, m), 1.70-2.00 (3H, m), 2.07-2.40 (2H, m), 2.88-3.30 (2H, m), 2.95 (2H, t, J=6.5 Hz), 4.16 (2H, t, J=6.5 Hz), 4.25-5.20 (3H, m), 5.90-7.40 (12H, m), 7.49 (1H, s).

Reference Example 83

2-(2,4-hexadienoyl)-7-{2-[2-(1-methyl-trans-1-penten-1-yl)oxazol-4-yl]ethoxy}-1,2,3,4-tetrahydroisoquinoline-(3S)-carboxylic Acid-tert-butylamine Salt $^1$H-NMR (CDCl$_3$) δ (ppm); 0.80-1.08 (3H, m), 0.97 (9H, s), 1.11-1.70 (2H, m), 1.70-1.93 (3H, m), 1.93-2.35 (2H, m), 2.01 (3H, s), 2.90-3.40 (2H, m), 2.96 (2H, t, J=6.7 Hz), 4.14 (2H, t, J=6.7 Hz), 4.24-5.20 (3H, m), 5.92-7.38 (11H, m), 7.50 (1H, s).

Reference Example 84

2-(2,4-hexadienoyl)-7-{2-[2-(1-methyl-trans-1-buten-1-yl)oxazol-4-yl]ethoxy}-1,2,3,4-tetrahydroisoquinoline-(3S)-carboxylic Acid-tert-butylamine Salt $^1$H-NMR (CDCl$_3$) δ (ppm); 0.99 (9H, s), 1.05 (3H, t, J=7.5 Hz), 1.65-1.95 (3H, m), 2.01 (3H, s), 2.05-2.45 (2H, m), 2.90-3.30 (2H, m), 2.96 (2H, t, J=6.7 Hz), 4.15 (2H, t, J=6.7 Hz), 4.25-5.20 (3H, m), 5.90-8.30 (13H, m).

Reference Example 85

2-(2,4-hexadienoyl)-7-{2-[(5-methyl-trans-1-hexen-1-yl)oxazol-4-yl]ethoxy}-1,2,3,4-tetrahydroisoquinoline-(3S)-carboxylic Acid-tert-butylamine Salt $^1$H-NMR (CDCl$_3$) δ (ppm); 0.90 (6H, d, J=6.3 Hz), 0.97 (9H, s), 1.20-1.70 (3H, m), 1.70-1.98 (3H, m), 2.06-2.40 (2H, m), 2.90-3.25 (2H, m), 2.95 (2H, t, J=6.4 Hz), 4.15 (2H, t, J=6.4 Hz), 4.25-5.20 (3H, m), 5.72-7.38 (12H, m), 7.50 (1H, s).

INDUSTRIAL APPLICABILITY

According to the present invention, a compound having PPARγ activation activity and PTP inhibitory activity (preferably PPARγ activation activity and PTP-1B inhibitory activity) has superior efficacy and has suppressed side effects (e.g., edema, cardiac enlargement, body fluid retention, hydrothorax etc.) caused by PPARγ activation activity. Therefore, it is useful as an agent for the prophylaxis or treatment of diabetes.

Sequence Listing Free Text

SEQ ID; NO. 3: PCR sense primer
SEQ ID; NO. 4: PCR antisense primer
SEQ ID; NO. 5: synthetic peptide 1 (Xaa of amino acid Nos. 5, 9 and 10 represents phosphotyrosine)
SEQ ID; NO. 7: PCR sense primer
SEQ ID; NO. 8: PCR antisense primer
SEQ ID; NO. 9: nucleotide sequence of synthetic human PPARγ cDNA
SEQ ID; NO. 10: nucleotide sequence of GAL4-PPARγ chimeric receptor gene
SEQ ID; NO. 11: amino acid sequence of GAL4-PPARγ chimeric receptor This application is based on a patent application No. 2003-152544 (filing date: May 29, 2003) filed in Japan, the contents of which are hereby incorporated by reference.

---

The invention claimed is:

1. A method of screening for an insulin sensitizer, which comprises the following steps 1) and 2):
   step 1) a step of measuring PTP-1B inhibitory activity of a test substance having PPARγ activation activity;
   step 2) a step of selecting a test substance having PTP-1B inhibitory activity, based on the PTP-1B inhibitory activity measured in step 1) above.

2. A method of screening for an insulin sensitizer, which comprises the following steps 1) to 4):
   step 1) a step of measuring PPARγ activation activity of a test substance;
   step 2) a step of selecting a substance having PPARγ activation activity, based on the PPARγ activation activity measured in step 1) above;
   step 3) a step of measuring PTP-1B inhibitory activity of the substance having PPARγ activation activity selected in step 2) above;
   step 4) a step of selecting a test substance having PTP-1B inhibitory activity, based on the PTP-1B inhibitory activity measured in step 3) above.

3. A method of screening for an insulin sensitizer, which comprises the following steps 1) and 2):
   step 1) a step of measuring PPARγ activation activity of a test substance having PTP-1B inhibitory activity;
   step 2) a step of selecting a test substance having PPARγ activation activity, based on the PPARγ activation activity measured in step 1) above.

4. A method of screening for an insulin sensitizer, which comprises the following steps 1) to 4):
   step 1) a step of measuring PTP-1B inhibitory activity of a test substance;
   step 2) a step of selecting a test substance having PTP-1B inhibitory activity, based on the PTP-1B inhibitory activity measured in step 1) above;
   step 3) a step of measuring the PPARγ activation activity of the substance having PTP-1B inhibitory activity selected in step 2) above;
   step 4) a step of selecting a test substance having PPARγ activation activity, based on the PPARγ activation activity measured in step 3) above.

* * * * *

SEQUENCE LISTING

```
<160> NUMBER OF SEQ ID NOS: 11

<210> SEQ ID NO 1
<211> LENGTH: 3215
<212> TYPE: DNA
<213> ORGANISM: Homo sapiens
<220> FEATURE:
<221> NAME/KEY: CDS
<222> LOCATION: (73)..(1377)

<400> SEQUENCE: 1
gcgcgacgcg gcctagagcg gcagacggcg cagtgggccg agaaggaggc gcagcagccg      60
ccctggcccg tc atg gag atg gaa aag gag ttc gag cag atc gac aag tcc     111
              Met Glu Met Glu Lys Glu Phe Glu Gln Ile Asp Lys Ser
                1               5                   10 ggg agc tgg gcg gcc att tac cag gat atc cga cat gaa gcc agt gac     159
Gly Ser Trp Ala Ala Ile Tyr Gln Asp Ile Arg His Glu Ala Ser Asp
 15                  20                  25
```

-continued

| | |
|---|---|
| ttc cca tgt aga gtg gcc aag ctt cct aag aac aaa aac cga aat agg<br>Phe Pro Cys Arg Val Ala Lys Leu Pro Lys Asn Lys Asn Arg Asn Arg<br>30                            35                       40                         45 | 207 |
| tac aga gac gtc agt ccc ttt gac cat agt cgg att aaa cta cat caa<br>Tyr Arg Asp Val Ser Pro Phe Asp His Ser Arg Ile Lys Leu His Gln<br>                  50                           55                           60 | 255 |
| gaa gat aat gac tat atc aac gct agt ttg ata aaa atg gaa gaa gcc<br>Glu Asp Asn Asp Tyr Ile Asn Ala Ser Leu Ile Lys Met Glu Glu Ala<br>                  65                           70                           75 | 303 |
| caa agg agt tac att ctt acc cag ggc cct ttg cct aac aca tgc ggt<br>Gln Arg Ser Tyr Ile Leu Thr Gln Gly Pro Leu Pro Asn Thr Cys Gly<br>                80                           85                           90 | 351 |
| cac ttt tgg gag atg gtg tgg gag cag aaa agc agg ggt gtc gtc atg<br>His Phe Trp Glu Met Val Trp Glu Gln Lys Ser Arg Gly Val Val Met<br>     95                       100                       105 | 399 |
| ctc aac aga gtg atg gag aaa ggt tcg tta aaa tgc gca caa tac tgg<br>Leu Asn Arg Val Met Glu Lys Gly Ser Leu Lys Cys Ala Gln Tyr Trp<br>110                       115                       120                       125 | 447 |
| cca caa aaa gaa gaa aaa gag atg atc ttt gaa gac aca aat ttg aaa<br>Pro Gln Lys Glu Glu Lys Glu Met Ile Phe Glu Asp Thr Asn Leu Lys<br>                 130                       135                       140 | 495 |
| tta aca ttg atc tct gaa gat atc aag tca tat tat aca gtg cga cag<br>Leu Thr Leu Ile Ser Glu Asp Ile Lys Ser Tyr Tyr Thr Val Arg Gln<br>               145                       150                       155 | 543 |
| cta gaa ttg gaa aac ctt aca acc caa gaa act cga gag atc tta cat<br>Leu Glu Leu Glu Asn Leu Thr Thr Gln Glu Thr Arg Glu Ile Leu His<br>             160                       165                       170 | 591 |
| ttc cac tat acc aca tgg cct gac ttt gga gtc cct gaa tca cca gcc<br>Phe His Tyr Thr Thr Trp Pro Asp Phe Gly Val Pro Glu Ser Pro Ala<br>175                       180                       185 | 639 |
| tca ttc ttg aac ttt ctt ttc aaa gtc cga gag tca ggg tca ctc agc<br>Ser Phe Leu Asn Phe Leu Phe Lys Val Arg Glu Ser Gly Ser Leu Ser<br>190                       195                       200                       205 | 687 |
| ccg gag cac ggg ccc gtt gtg gtg cac tgc agt gca ggc atc ggc agg<br>Pro Glu His Gly Pro Val Val Val His Cys Ser Ala Gly Ile Gly Arg<br>                     210                       215                       220 | 735 |
| tct gga acc ttc tgt ctg gct gat acc tgc ctc ttg ctg atg gac aag<br>Ser Gly Thr Phe Cys Leu Ala Asp Thr Cys Leu Leu Leu Met Asp Lys<br>                   225                       230                       235 | 783 |
| agg aaa gac cct tct tcc gtt gat atc aag aaa gtg ctg tta gaa atg<br>Arg Lys Asp Pro Ser Ser Val Asp Ile Lys Lys Val Leu Leu Glu Met<br>               240                       245                       250 | 831 |
| agg aag ttt cgg atg ggg ctg atc cag aca gcc gac cag ctg cgc ttc<br>Arg Lys Phe Arg Met Gly Leu Ile Gln Thr Ala Asp Gln Leu Arg Phe<br>             255                       260                       265 | 879 |
| tcc tac ctg gct gtg atc gaa ggt gcc aaa ttc atc atg ggg gac tct<br>Ser Tyr Leu Ala Val Ile Glu Gly Ala Lys Phe Ile Met Gly Asp Ser<br>270                       275                       280                       285 | 927 |
| tcc gtg cag gat cag tgg aag gag ctt tcc cac gag gac ctg gag ccc<br>Ser Val Gln Asp Gln Trp Lys Glu Leu Ser His Glu Asp Leu Glu Pro<br>                     290                       295                       300 | 975 |
| cca ccc gag cat atc ccc cca cct ccc cgg cca ccc aaa cga atc ctg<br>Pro Pro Glu His Ile Pro Pro Pro Pro Arg Pro Pro Lys Arg Ile Leu<br>                     305                       310                       315 | 1023 |
| gag cca cac aat ggg aaa tgc agg gag ttc ttc cca aat cac cag tgg<br>Glu Pro His Asn Gly Lys Cys Arg Glu Phe Phe Pro Asn His Gln Trp<br>             320                       325                       330 | 1071 |
| gtg aag gaa gag acc cag gag gat aaa gac tgc ccc atc aag gaa gaa<br>Val Lys Glu Glu Thr Gln Glu Asp Lys Asp Cys Pro Ile Lys Glu Glu | 1119 |

```
                335                 340                 345
aaa gga agc ccc tta aat gcc gca ccc tac ggc atc gaa agc atg agt      1167
Lys Gly Ser Pro Leu Asn Ala Ala Pro Tyr Gly Ile Glu Ser Met Ser
350                 355                 360                 365 caa gac act gaa gtt aga agt cgg gtc gtg ggg gga agt ctt cga ggt      1215
Gln Asp Thr Glu Val Arg Ser Arg Val Val Gly Gly Ser Leu Arg Gly
                370                 375                 380 gcc cag gct gcc tcc cca gcc aaa ggg gag ccg tca ctg ccc gag aag      1263
Ala Gln Ala Ala Ser Pro Ala Lys Gly Glu Pro Ser Leu Pro Glu Lys
            385                 390                 395 gac gag gac cat gca ctg agt tac tgg aag ccc ttc ctg gtc aac atg      1311
Asp Glu Asp His Ala Leu Ser Tyr Trp Lys Pro Phe Leu Val Asn Met
                400                 405                 410 tgc gtg gct acg gtc ctc acg gcc ggc gct tac ctc tgc tac agg ttc      1359
Cys Val Ala Thr Val Leu Thr Ala Gly Ala Tyr Leu Cys Tyr Arg Phe
        415                 420                 425 ctg ttc aac agc aac aca tagcctgacc ctcctccact ccacctccac             1407
Leu Phe Asn Ser Asn Thr
430                 435 ccactgtccg cctctgcccg cagagcccac gcccgactag caggcatgcc gcggtaggta    1467
agggccgccg gaccgcgtag agagccgggc cccggacgga cgttggttct gcactaaaac    1527
ccatcttccc cggatgtgtg tctcacccct catccttta cttttgccc cttccacttt      1587
gagtaccaaa tccacaagcc attttttgag gagagtgaaa gagagtacca tgctggcggc    1647
gcagagggaa ggggcctaca cccgtcttgg ggctcgcccc acccagggct ccctcctgga    1707
gcatcccagg cgggcggcac gccagacagc cccccccttg aatctgcagg gagcaactct    1767
ccactccata tttatttaaa caatttttc cccaaaggca tccatagtgc actagcattt     1827
tcttgaacca ataatgtatt aaaattttt gatgtcagcc ttgcatcaag ggctttatca     1887
aaaagtacaa taataaatcc tcaggtagta ctgggaatgg aaggctttgc catgggcctg    1947
ctgcgtcaga ccagtactgg gaaggaggac ggttgtaagc agttgttatt tagtgatatt    2007
gtgggtaacg tgagaagata gaacaatgct ataatatata tgaacacgt gggtatttaa     2067
taagaaacat gatgtgagat tactttgtcc cgcttattct gctccctgtt atctgctaga    2127
tctagttctc aatcactgct cccccgtgtg tattagaatg catgtaaggt cttcttgtgt    2187
cctgatgaaa aatatgtgct tgaaatgaga actttgatc tctgcttact aatgtgcccc     2247
atgtccaagt ccaacctgcc tgtgcatgac ctgatcatta catggctgtg gttcctaagc    2307
ctgttgctga agtcattgtc gctcagcaat agggtgcagt tttccaggaa taggcatttg    2367
cctaattcct ggcatgacac tctagtgact tcctggtgag gcccagcctg tcctggtaca    2427
gcagggtctt gctgtaactc agacattcca agggtatggg aagccatatt cacacctcac    2487
gctctggaca tgatttaggg aagcagggac accccccgcc ccccacctt gggatcagcc     2547
tccgccattc caagtcgaca ctcttcttga gcagaccgtg atttggaaga gaggcacctg    2607
ctggaaacca cacttcttga aacagcctgg gtgacggtcc tttaggcagc ctgccgccgt    2667
ctctgtcccg gttcaccttg ccgagagagg gcgtctgcc ccaccctcaa accctgtggg     2727
gcctgatggt gctcacgact cttcctgcaa agggaactga agacctccac attaagtggc    2787
tttttaacat gaaaaacacg gcagctgtag ctcccgagct actctcttgc cagcattttc    2847
acattttgcc tttctcgtgg tagaagccag tacagagaaa ttctgtggtg ggaacattcg    2907
aggtgtcacc ctgcagagct atggtgaggt gtggataagg cttaggtgcc aggctgtaag    2967
cattctgagc tggcttgttg ttttaagtc ctgtatatgt atgtagtagt ttgggtgtgt     3027
```

-continued

```
atatatagta gcatttcaaa atggacgtac tggtttaacc tcctatcctt ggagagcagc    3087
tggctctcca ccttgttaca cattatgtta gagaggtagc gagctgctct gctatgtcct    3147
taagccaata tttactcatc aggtcattat tttttacaat ggccatggaa taaaccattt    3207
ttacaaaa                                                             3215
```

<210> SEQ ID NO 2
<211> LENGTH: 435
<212> TYPE: PRT
<213> ORGANISM: Homo sapiens

<400> SEQUENCE: 2

```
Met Glu Met Glu Lys Glu Phe Glu Gln Ile Asp Lys Ser Gly Ser Trp
  1               5                  10                  15

Ala Ala Ile Tyr Gln Asp Ile Arg His Glu Ala Ser Asp Phe Pro Cys
             20                  25                  30

Arg Val Ala Lys Leu Pro Lys Asn Lys Asn Arg Asn Arg Tyr Arg Asp
         35                  40                  45

Val Ser Pro Phe Asp His Ser Arg Ile Lys Leu His Gln Glu Asp Asn
     50                  55                  60

Asp Tyr Ile Asn Ala Ser Leu Ile Lys Met Glu Glu Ala Gln Arg Ser
 65                  70                  75                  80

Tyr Ile Leu Thr Gln Gly Pro Leu Pro Asn Thr Cys Gly His Phe Trp
                 85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val Val His Cys Ser Ala Gly Ile Gly Arg Ser Gly Thr
    210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
        275                 280                 285

Asp Gln Trp Lys Glu Leu Ser His Glu Asp Leu Glu Pro Pro Pro Glu
    290                 295                 300

His Ile Pro Pro Pro Pro Arg Pro Pro Lys Arg Ile Leu Glu Pro His
305                 310                 315                 320

Asn Gly Lys Cys Arg Glu Phe Phe Pro Asn His Gln Trp Val Lys Glu
                325                 330                 335
```

```
Glu Thr Gln Glu Asp Lys Asp Cys Pro Ile Lys Glu Glu Lys Gly Ser
        340                 345                 350

Pro Leu Asn Ala Ala Pro Tyr Gly Ile Glu Ser Met Ser Gln Asp Thr
        355                 360                 365

Glu Val Arg Ser Arg Val Val Gly Gly Ser Leu Arg Gly Ala Gln Ala
    370                 375                 380

Ala Ser Pro Ala Lys Gly Glu Pro Ser Leu Pro Glu Lys Asp Glu Asp
385                 390                 395                 400

His Ala Leu Ser Tyr Trp Lys Pro Phe Leu Val Asn Met Cys Val Ala
                405                 410                 415

Thr Val Leu Thr Ala Gly Ala Tyr Leu Cys Tyr Arg Phe Leu Phe Asn
            420                 425                 430

Ser Asn Thr
        435

<210> SEQ ID NO 3
<211> LENGTH: 32
<212> TYPE: DNA
<213> ORGANISM: Artificial Sequence
<220> FEATURE:
<223> OTHER INFORMATION: Synthetic Construct

<400> SEQUENCE: 3
agctggatcc atatggagat ggaaaaggag tt                                    32

<210> SEQ ID NO 4
<211> LENGTH: 34
<212> TYPE: DNA
<213> ORGANISM: Artificial Sequence
<220> FEATURE:
<223> OTHER INFORMATION: Synthetic Construct

<400> SEQUENCE: 4
acgcgaattc ttaattgtgt ggctccagga ttcg                                  34

<210> SEQ ID NO 5
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: PEPTIDE
<222> LOCATION: 5
<223> OTHER INFORMATION: Xaa represents Phosphorylated Tyrosine
<220> FEATURE:
<221> NAME/KEY: PEPTIDE
<222> LOCATION: 9
<223> OTHER INFORMATION: Xaa represents Phosphorylated Tyrosine
<220> FEATURE:
<221> NAME/KEY: PEPTIDE
<222> LOCATION: 10
<223> OTHER INFORMATION: Xaa represents Phosphorylated Tyrosine

<400> SEQUENCE: 5

Thr Arg Asp Ile Xaa Glu Thr Asp Xaa Xaa Arg Lys
  1               5                  10

<210> SEQ ID NO 6
<211> LENGTH: 1766
<212> TYPE: DNA
<213> ORGANISM: Homo sapiens

<400> SEQUENCE: 6
```

-continued

```
cgcgcactcg gagcccgagc ccgagccgca gctgccgcct ggggcgcttg ggtcggcctc     60
gaggacaccg gagaggggcg ccacgccgcc gtggccgcag aaatgaccat ggttgacaca   120
gagatgccat tctggcccac caactttggg atcagctccg tggatctctc cgtaatggaa   180
gaccactccc actcctttga tatcaagccc ttcactactg ttgacttctc cagcatttct   240
actccacatt acgaagacat tccattcaca gaacagatc cagtggttgc agattacaag    300
tatgacctga aacttcaaga gtaccaaagt gcaatcaaag tggagcctgc atctccacct   360
tattattctg agaagactca gctctacaat aagcctcatg aagagccttc caactcccct   420
atggcaattg aatgtcgtgt ctgtggagat aaagcttctg gatttcacta tggagttcat   480
gcttgtgaag gatgcaaggg tttcttccgg agaacaatca gattgaagct tatctatgac   540
agatgtgatc ttaactgtcg gatccacaaa aaaagtagaa ataaatgtca gtactgtcgg   600
tttcagaaat gccttgcagt ggggatgtct cataatgcca tcaggtttgg gcggatgcca   660
caggccgaga aggagaagct gttggcgag atctccagtg atatcgacca gctgaatcca    720
gagtccgctg acctccgggc cctggcaaaa catttgtatg actcatacat aaagtccttc   780
ccgctgacca agcaaaggc gagggcgatc ttgacaggaa agacaacaga caatcacca     840
ttcgttatct atgacatgaa ttccttaatg atgggagaag ataaaatcaa gttcaaacac   900
atcacccccc tgcaggagca gagcaaagag gtggccatcc gcatcttca gggctgccag    960
tttcgctccg tggaggctgt gcaggagatc acagagtatg ccaaaagcat tcctggtttt  1020
gtaaatcttg acttgaacga ccaagtaact ctcctcaaat atggagtcca cgagatcatt  1080
tacacaatgc tggcctcctt gatgaataaa gatgggttc tcatatccga gggccaaggc   1140
ttcatgacaa gggagtttct aaagagcctg cgaaagcctt ttggtgactt tatggagccc  1200
aagtttgagt ttgctgtgaa gttcaatgca ctggaattag atgacagcga cttggcaata  1260
tttattgctg tcattattct cagtggagac cgcccaggtt tgctgaatgt gaagcccatt  1320
gaagacattc aagacaacct gctacaagcc ctggagctcc agctgaagct gaaccaccct  1380
gagtcctcac agctgtttgc caagctgctc cagaaaatga cagacctcag acagattgtc  1440
acggaacacg tgcagctact gcaggtgatc aagaagacgg acagacat gagtcttcac    1500
ccgctcctgc aggagatcta caaggacttg tactagcaga gagtcctgag ccactgccaa  1560
catttcccctt cttccagttg cactattctg agggaaaatc tgacacctaa gaaatttact  1620
gtgaaaaagc attttaaaaa gaaaggttt tagaatatga tctatttat gcatattgtt    1680
tataaagaca catttacaat ttactttta tattaaaaat taccatatta tgaaaaaaaa   1740
aaaaaaaaaa aaaaaaaaa aaaaaa                                       1766
```

<210> SEQ ID NO 7
<211> LENGTH: 29
<212> TYPE: DNA
<213> ORGANISM: Artificial Sequence
<220> FEATURE:
<223> OTHER INFORMATION: Synthetic Construct

<400> SEQUENCE: 7
ggatccataa tgccatcagg tttgggcgg                                     29

<210> SEQ ID NO 8
<211> LENGTH: 30
<212> TYPE: DNA
<213> ORGANISM: Artificial Sequence
<220> FEATURE:
<223> OTHER INFORMATION: Synthetic Construct

<400> SEQUENCE: 8
aagcttctag tacaagtcct tgtagatctc                                           30

<210> SEQ ID NO 9
<211> LENGTH: 917
<212> TYPE: DNA
<213> ORGANISM: Artificial Sequence
<220> FEATURE:
<223> OTHER INFORMATION: Synthetic Construct

<400> SEQUENCE: 9
ggatccataa tgccatcagg tttgggcgga tgccacaggc cgagaaggag aagctgttgg          60
cggagatctc cagtgatatc gaccagctga atccagagtc cgctgacctc cgggccctgg         120
caaaacattt gtatgactca tacataaagt ccttcccgct gaccaaagca aaggcgaggg         180
cgatcttgac aggaaagaca acagacaaat caccattcgt tatctatgac atgaattcct         240
taatgatggg agaagataaa atcaagttca aacacatcac cccctgcag gagcagagca          300 aagaggtggc catccgcatc tttcagggct gccagtttcg ctccgtggag ctgtgcagg          360 agatcacaga gtatgccaaa gcattcctg gttttgtaaa tcttgacttg aacgaccaag          420
taactctcct caaatatgga gtccacgaga tcatttacac aatgctggcc tccttgatga        480
ataaagatgg ggttctcata tccgagggcc aaggcttcat gacaagggag tttctaaaga        540
gcctgcgaaa gccttttggt gactttatgg agcccaagtt tgagtttgct gtgaagttca        600
atgcactgga attagatgac agcgacttgg caatatttat tgctgtcatt attctcagtg        660
gagaccgccc aggtttgctg aatgtgaagc ccattgaaga cattcaagac aacctgctac        720
aagccctgga gctccagctg aagctgaacc accctgagtc ctcacagctg tttgccaagc        780
tgctccagaa aatgacagac ctcagacaga ttgtcacgga acacgtgcag ctactgcagg        840
tgatcaagaa gacggagaca gacatgagtc ttcacccgct cctgcaggag atctacaagg        900
acttgtacta gaagctt                                                       917

<210> SEQ ID NO 10
<211> LENGTH: 1365
<212> TYPE: DNA
<213> ORGANISM: Artificial Sequence
<220> FEATURE:
<223> OTHER INFORMATION: Synthetic Construct

<400> SEQUENCE: 10
atgaagctac tgtcttctat cgaacaagca tgcgatattt gccgacttaa aaagctcaag         60
tgctccaaag aaaaaccgaa gtgcgccaag tgtctgaaga caactgggag tgtcgctac         120 tctcccaaaa ccaaaaggtc tccgctgact agggcacatc tgacagaagt ggaatcaagg        180 ctagaaaagac tggaacagct atttctactg attttcctc gagaagacct tgacatgatt       240
ttgaaaatgg attctttaca ggatataaaa gcattgttaa caggattatt tgtacaagat       300
aatgtgaata agatgccgt cacagataga ttggcttcag tggagactga tatgcctcta        360
acattgagac agcatagaat aagtgcgaca tcatcatcgg aagagagtag taacaaaggt       420
caaagacagt tgactgtatc gccgaattc ccggggatcc ataatgccat caggtttggg        480
cggatgccac aggccgagaa ggagaagctg ttggcggaga tctccagtga tatcgaccag       540
ctgaatccag agtccgctga cctccgggcc ctggcaaaac attttgtatga ctcatacata       600 aagtccttcc cgctgaccaa agcaaaggcg agggcgatct tgacaggaaa gacaacagac       660

```
aaatcaccat tcgttatcta tgacatgaat tccttaatga tgggagaaga taaaatcaag    720
ttcaaacaca tcacccccct gcaggagcag agcaaagagg tggccatccg catctttcag    780
ggctgccagt ttcgctccgt ggaggctgtg caggagatca cagagtatgc caaaagcatt    840
cctggttttg taaatcttga cttgaacgac caagtaactc tcctcaaata tggagtccac    900
gagatcattt acacaatgct ggcctccttg atgaataaag atggggttct catatccgag    960
ggccaaggct tcatgacaag ggagtttcta aagagcctgc gaaagccttt tggtgacttt   1020
atggagccca gtttgagtt tgctgtgaag ttcaatgcac tggaattaga tgacagcgac   1080
ttggcaatat ttattgctgt cattattctc agtggagacc gcccaggttt gctgaatgtg   1140
aagcccattg aagacattca agacaacctg ctacaagccc tggagctcca gctgaagctg   1200
aaccaccctg agtcctcaca gctgtttgcc aagctgctcc agaaaatgac agacctcaga   1260
cagattgtca cggaacacgt gcagctactg caggtgatca agaagacgga cacagacatg   1320
agtcttcacc cgctcctgca ggagatctac aaggacttgt actag                   1365
```

<210> SEQ ID NO 11
<211> LENGTH: 454
<212> TYPE: PRT
<213> ORGANISM: Artificial Sequence
<220> FEATURE:
<223> OTHER INFORMATION: Synthetic Construct

<400> SEQUENCE: 11

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Ile His Asn Ala Ile Arg Phe Gly
145                 150                 155                 160

Arg Met Pro Gln Ala Glu Lys Glu Lys Leu Leu Ala Glu Ile Ser Ser
                165                 170                 175

Asp Ile Asp Gln Leu Asn Pro Glu Ser Ala Asp Leu Arg Ala Leu Ala
            180                 185                 190

Lys His Leu Tyr Asp Ser Tyr Ile Lys Ser Phe Pro Leu Thr Lys Ala
        195                 200                 205

Lys Ala Arg Ala Ile Leu Thr Gly Lys Thr Thr Asp Lys Ser Pro Phe
    210                 215                 220

Val Ile Tyr Asp Met Asn Ser Leu Met Met Gly Glu Asp Lys Ile Lys
225                 230                 235                 240
```

```
Phe Lys His Ile Thr Pro Leu Gln Glu Gln Ser Lys Glu Val Ala Ile
                245                 250                 255

Arg Ile Phe Gln Gly Cys Gln Phe Arg Ser Val Glu Ala Val Gln Glu
                260                 265                 270

Ile Thr Glu Tyr Ala Lys Ser Ile Pro Gly Phe Val Asn Leu Asp Leu
                275                 280                 285

Asn Asp Gln Val Thr Leu Leu Lys Tyr Gly Val His Glu Ile Ile Tyr
    290                 295                 300

Thr Met Leu Ala Ser Leu Met Asn Lys Asp Gly Val Leu Ile Ser Glu
305                 310                 315                 320

Gly Gln Gly Phe Met Thr Arg Glu Phe Leu Lys Ser Leu Arg Lys Pro
                325                 330                 335

Phe Gly Asp Phe Met Glu Pro Lys Phe Glu Phe Ala Val Lys Phe Asn
                340                 345                 350

Ala Leu Glu Leu Asp Asp Ser Asp Leu Ala Ile Phe Ile Ala Val Ile
                355                 360                 365

Ile Leu Ser Gly Asp Arg Pro Gly Leu Leu Asn Val Lys Pro Ile Glu
    370                 375                 380

Asp Ile Gln Asp Asn Leu Leu Gln Ala Leu Glu Leu Gln Leu Lys Leu
385                 390                 395                 400

Asn His Pro Glu Ser Ser Gln Leu Phe Ala Lys Leu Leu Gln Lys Met
                405                 410                 415

Thr Asp Leu Arg Gln Ile Val Thr Glu His Val Gln Leu Leu Gln Val
                420                 425                 430

Ile Lys Lys Thr Glu Thr Asp Met Ser Leu His Pro Leu Leu Gln Glu
                435                 440                 445

Ile Tyr Lys Asp Leu Tyr
    450
```